United States Patent
Wu et al.

(10) Patent No.: US 11,427,597 B2
(45) Date of Patent: *Aug. 30, 2022

(54) HETEROARYL AMIDE COMPOUNDS AS STING ACTIVATORS

(71) Applicant: Incyte Corporation, Wilmington, DE (US)

(72) Inventors: Liangxing Wu, Wilmington, DE (US); Neil Lajkiewicz, Garnet Valley, PA (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 27 days.

This patent is subject to a terminal disclaimer.

(21) Appl. No.: 17/079,094

(22) Filed: Oct. 23, 2020

(65) Prior Publication Data

US 2021/0163493 A1    Jun. 3, 2021

Related U.S. Application Data

(63) Continuation of application No. 16/528,062, filed on Jul. 31, 2019, now Pat. No. 10,875,872.

(60) Provisional application No. 62/712,360, filed on Jul. 31, 2018.

(51) Int. Cl.
| | | |
|---|---|---|
| *A61K 31/4188* | (2006.01) | |
| *C07D 491/048* | (2006.01) | |
| *C07D 491/056* | (2006.01) | |
| *A61K 45/06* | (2006.01) | |

(52) U.S. Cl.
CPC ..... *C07D 491/048* (2013.01); *C07D 491/056* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,521,184 A | 5/1996 | Zimmermann | |
| 10,875,872 B2 | 12/2020 | Wu et al. | |
| 10,947,227 B2 | 3/2021 | Wu et al. | |
| 11,008,344 B2 | 5/2021 | Wu et al. | |
| 2017/0146519 A1 | 5/2017 | DeFillipis et al. | |
| 2018/0105514 A1 | 4/2018 | Mehlmann et al. | |
| 2018/0177784 A1 | 6/2018 | Wu et al. | |
| 2018/0177870 A1 | 6/2018 | Liu et al. | |
| 2018/0179179 A1 | 6/2018 | Wu et al. | |
| 2018/0179197 A1 | 6/2018 | Wu et al. | |
| 2018/0179201 A1 | 6/2018 | Wu et al. | |
| 2018/0179202 A1 | 6/2018 | Wu et al. | |
| 2019/0300524 A1 | 10/2019 | Wu et al. | |
| 2019/0359608 A1 | 11/2019 | Wu et al. | |
| 2020/0039994 A1 | 2/2020 | Wu et al. | |
| 2020/0040009 A1 | 2/2020 | Wu et al. | |
| 2021/0332067 A1 | 10/2021 | Wu et al. | |
| 2022/0056049 A1 | 2/2022 | Wu et al. | |
| 2022/0073509 A1 | 3/2022 | Wu et al. | |

FOREIGN PATENT DOCUMENTS

| | | |
|---|---|---|
| CN | 105367617 | 3/2016 |
| CN | 107335049 | 11/2017 |
| WO | WO 2000/009495 | 2/2000 |
| WO | WO 2000/053595 | 9/2000 |
| WO | WO 2001/014402 | 3/2001 |
| WO | WO 2001/064655 | 9/2001 |
| WO | WO 2002/000196 | 1/2002 |
| WO | WO 2003/024967 | 3/2003 |
| WO | WO 2003/037347 | 5/2003 |
| WO | WO 2003/099771 | 12/2003 |
| WO | WO 2004/005281 | 1/2004 |
| WO | WO 2004/046120 | 6/2004 |
| WO | WO 2004/056786 | 7/2004 |
| WO | WO 2004/080980 | 9/2004 |
| WO | WO 2005/028444 | 3/2005 |
| WO | WO 2006/056399 | 6/2006 |
| WO | WO 2014/093936 | 6/2014 |
| WO | WO 2015/061294 | 4/2015 |
| WO | WO 2015/077354 | 5/2015 |
| WO | WO 2015/143161 | 9/2015 |
| WO | WO 2015/185565 | 12/2015 |
| WO | WO 2016/096577 | 6/2016 |
| WO | WO 2016/120305 | 8/2016 |
| WO | WO 2017/011444 | 1/2017 |
| WO | WO 2017/011622 | 1/2017 |
| WO | WO 2017/011920 | 1/2017 |
| WO | WO 2017/027645 | 2/2017 |
| WO | WO 2017/027646 | 2/2017 |
| WO | WO 2017/053537 | 3/2017 |
| WO | WO 2017/093933 | 6/2017 |
| WO | WO 2017/100305 | 6/2017 |
| WO | WO 2017/106740 | 6/2017 |
| WO | WO 2017/123657 | 7/2017 |
| WO | WO 2017/123669 | 7/2017 |

(Continued)

OTHER PUBLICATIONS

Atzrodt et al., "The Renaissance of H/D Exchange," Angew. Chem. Int. Ed., Oct. 4, 2007, 7744-7765.
Azzoni et al., "Pegylated Interferon Alfa-2a Monotherapy Results in Suppression of HIV Type 1 Replication and Decreased Cell-Associated HIV DNA Integration," J. Infect. Dis., Oct. 2012, 207:213-222.
Barber et al., "STING: infection, inflammation and cancer," Nat Rev Immunol., Dec. 2015, 15(12):760-770.
Beutler, "TLRs and innate immunity," Blood, Feb. 12, 2009, 113:1399-1407.
Blom et al., "Preparative LC-MS Purification: Improved Compound Specific Method Optimization," J. Combi. Chem., Sep. 11, 2014, 6:874-883.

(Continued)

*Primary Examiner* — Samantha L Shterengarts
(74) *Attorney, Agent, or Firm* — Fish & Richardson P.C.

(57) ABSTRACT

The present application provides heteroaryl amide compounds that activate the STING pathway to produce interferons, which are useful in the treatment of various diseases including infectious diseases and cancer.

41 Claims, No Drawings

(56) References Cited

FOREIGN PATENT DOCUMENTS

| | | |
|---|---|---|
| WO | WO 2017/151922 | 9/2017 |
| WO | WO 2017/161349 | 9/2017 |
| WO | WO 2017/175147 | 10/2017 |
| WO | WO 2017/175156 | 10/2017 |
| WO | WO 2017/186711 | 11/2017 |
| WO | WO 2018/060323 | 4/2018 |
| WO | WO 2018/067423 | 4/2018 |
| WO | WO 2018/234805 | 12/2018 |
| WO | WO 2018/234807 | 12/2018 |
| WO | WO 2018/234808 | 12/2018 |
| WO | WO 2019/027857 | 2/2019 |
| WO | WO 2019/027858 | 2/2019 |
| WO | WO 2019/069269 | 4/2019 |
| WO | WO 2019/069270 | 4/2019 |
| WO | WO 2019/069275 | 4/2019 |
| WO | WO 2019/134705 | 7/2019 |
| WO | WO 2019/137707 | 7/2019 |
| WO | WO 2019/219820 | 11/2019 |
| WO | WO 2020/006432 | 1/2020 |
| WO | WO 2020/132549 | 6/2020 |

OTHER PUBLICATIONS

Blom et al., "Optimizing Preparative LC-MS Configurations and Methods for Parallel Synthesis Purification," J. Combi. Chem., Jul. 29, 2003, 5:670-683.

Blom et al., "Two-Pump At col. Dilution Configuration for Preparative LC-MS," Journal of Combinatorial Chemistry, Apr. 12, 2002, 4:295-301.

Burdette et al., " STING and the innate immune response to nucleic acids in the cytosol," Nat. Immunol. Jan. 2013, 14:19-26.

Cai et al., "The cGAS-cGAMP-STING Pathway of Cytosolic DNA Sensing and Signaling," Mol. Cell Review, Apr. 24, 2014, 54:289-296.

Caviar et al., "Species-specific detection of the antiviral small-molecule compound CMA by Sting," EMBO J. May 15, 2013, 32:1440-1450.

Chen et al., "Regulation and function of the cGAS-STING pathway of cytosolic DNA sensing," Nature Immunol., Oct. 2016, 17(10):1142-1149.

Cheng et al., "Pharmacologic Activation of the Innate Immune System to Prevent Respiratory Viral Infections," Am. J. Respir. Cell. Mol. Biol., Sep. 2011, 45:480-488.

Conlon et al., "Mouse, but not Human STING, Binds and Signals in Response to the Vascular Disrupting Agent 5,6-Dimethylxanthenone-4-Acetic Acid," J Immunol., 2013, 190:5216-5225.

Corrales et al., "Direct Activation of STING in the Tumor Microenvironment Leads to Potent and Systemic Tumor Regression and Immunity," Cell Reports, May 19, 2015, 11:1018-1030.

Crosse et al., "Interferon-Stimulated Genes as Enhancers of Antiviral Innate Immune Signaling," J. Innate Immun., Nov. 30, 2017, 10:85-93.

Diprivan, Reference ID No. 4089428, retrieved from https://www.accessdata.fda.gov/drugsatfda_docs/label/2017/019627s066lbl.pdf, Apr. 2017, 54 pages.

Enomoto et al., "Factors associated with the response to interferon-based antiviral therapies for chronic hepatitis C," World J. Hepatol, Nov. 18, 2015, 7:2681-2687.

Gao et al., "Structure-Function Analysis of STING Activation by c[G(20,50)pA(30,50)p]and Targeting by Antiviral DMXAA," Cell, Aug. 13, 2013, 154(4):748-762.

Garbe et al., "Diagnosis and treatment of cutaneous melanoma: state of the art 2006*," Melanoma Res. Apr. 2007, 17:117-127.

Guo et al., "STING agonists induce an innate antiviral immune response against hepatitis B virus," Antimicrobial Agents and Chemotherapy, Dec. 15, 2014, 59:1273-1281.

Hervas-Stubbs et al., "Direct Effects of Type I Interferons on Cells of the Immune System," Clin. Cancer Res., May 1, 2011, 17:2619-2627.

International Search Report and Written Opinion in International Application No. PCT/US2019/033944, dated Sep. 19, 2019, 13 pages.

International Search Report and Written Opinion in International Application No. PCT/US2019/044499, dated Nov. 20, 2019, 13 pages.

International Search Report and Written Opinion in International Application No. PCT/US2019/044500, dated Nov. 20, 2019, 13 pages.

Ishikawa et al., "STING is an endoplasmic reticulum adaptor that facilitates innate immune signalling," Nature, Oct. 2, 2018, 455:674-678.

Kerekes et al., "Aurora Kinase Inhibitors Based on the Imidazo[1,2-a]pyrazine Core: Fluorine and Deuterium Incorporation Improve Oral Absorption and Exposure," J. Med. Chem., Dec. 3, 2010, 54:201-210.

Khiar et al., "Identification of a small molecule that primes the type I interferon response to cytosolic DNA," Scientific Reports, May 31, 2017, 7:2561.

Kim et al., "Anticancer Flavonoids Are Mouse-Selective STING Agonists," ACS Chem. Biol., May 17, 2013, 8:1396-1401.

Kirkwood, "Cancer Immunotherapy: The Interferon—Experience," Semin. Oncol., Jun. 1, 2002, 29:18-26.

Kramer et al., "Antiviral Activity of 10-Carboxymethyl-9-Acridanone," Antimicrobial Agents and Chemotherapy, Feb. 1, 1976, 9:233-238.

Lane et al., "Interferon-α in Patients with Asymptomatic Human Immunodeficiency Virus (HIV) Infection: A Randomized, Placebo-Controlled Trial," Ann. Intern. Med., Jun. 1, 1990, 112:805-811.

Larkin et al., "Cutting Edge: Activation of STING in T Cells Induces Type I IFN Responses and Cell Death," J Immunol., 2017, 199:397-402.

Liu et al., "A cell-based high throughput screening assay for the discovery of cGASSTING pathway agonists," Antiviral Research, 2017, 147:37-46.

McNab et al., "Type I interferons in infectious disease. Nature Reviews Immunology," Nat Rev Immunol, Feb. 2015, 15:87-103.

Palm et al., "Pattern recognition receptors and control of adaptive immunity," Immunol Rev. Jan. 2009, 227:221-233.

Perera et al., "Activation of LPS-inducible genes by the antitumor agent 5,6-dimethylxanthenone-4-acetic acid in primary murine macrophages. Dissection of signaling pathways leading to gene induction and tyrosine phosphorylation," J. Immunol., Nov. 15, 1994, 153:4684-4697.

Pizzocaro et al, "Interferon Adjuvant to Radical Nephrectomy in Robson Stages II and III Renal Cell Carcinoma: A Multicentric Randomized Study," J. Clin. Oncol., Jan. 15, 2001, 19:425-431.

Quesada et al., "Alpha Interferon for Induction of Remission in Hairy-Cell Leukemia," N. Engl. J. Med. Jan. 5, 1984, 310:15-18.

Ramanjulu et al., "Design of amidobenzimidazole STING receptor agonists with systemic activity," Nature, 2018, 564:439-443.

Ramanjulu et al., "Design of amidobenzimidazole STING receptor agonists with systemic activity," Nature, 2018, Supplementary Information, 66 pages.

Remington et al., "Remington's Pharmaceutical Sciences," 17th ed., 1985, p. 1418.

Sali et al., "Characterization of a Novel Human-Specific STING Agonist that Elicits Antiviral Activity Against Emerging Alphaviruses," PLoS Pathog., Dec. 8, 2015, 11(12):e1005324.

SciFinder Search Results, generated Jun. 27, 2018, 1 page.

SciFinder Search Results, generated Jun. 27, 2018, 22 pages.

Siu et al., "Discovery of a Novel cGAMP Competitive Ligand of the Inactive Form of STING," ACS Med Chem Lett., 2019, 10(1):92-97.

Sokolowska et al., "STING Signaling in Cancer Cells: Important or Not?" Arch Immunol Ther Exp., Jul. 26, 2017, 66:125-132.

Takeuchi et al., "Innate immunity to virus infection," Immunol Rev., Jan. 2009, 227:75-86.

Tang et al., "Benefits of Therapeutic Drug Monitoring of Vancomycin: A Systematic Review and Meta-Analysis," Pios One, Oct. 2013, 8:1-10.

Tarhini et al., "IFN-α in the Treatment of Melanoma," J. Immunol., Oct. 2012, 189:3789-3793.

(56) References Cited

OTHER PUBLICATIONS

Vannucchi et al., "Perspectives in Biomolecular Therapeutic Intervention in Cancer: From the Early to the New Strategies With Type I Interferons," Curr. Med. Chem., Mar. 1, 2007, 14:667-679.
Wallace et al., "The Vascular Disrupting Agent, DMXAA, Directly Activates Dendritic Cells through a MyD88-Independent Mechanism and Generates Antitumor Cytotoxic T Lymphocytes," Cancer Research, Jul. 2007, 67:7011-7019.
Xu et al., "Design, synthesis and biological evaluation of deuterated nintedanib for improving pharmacokinetic properties," J. Label Compd. Radiopharm. May 26, 2015, 58:308-312.
International Preliminary Report on Patentability in International Application No. PCT/US2019/044499, dated Feb. 11, 2021, 7 pages.
International Preliminary Report on Patentability in International Application No. PCT/US2019/044500, dated Feb. 11, 2021, 7 pages.
International Search Report and Written Opinion in International Application No. PCT/US2020/012324, dated Mar. 30, 2020, 13 pages.
International Preliminary Report on Patentability in International Application No. PCT/US2020/012324, dated Jun. 16, 2021, 8 pages.

HETEROARYL AMIDE COMPOUNDS AS STING ACTIVATORS

CROSS-REFERENCE TO RELATED APPLICATIONS

This application is a continuation of U.S. patent application Ser. No. 16/528,062, filed Jul. 31, 2019, which claims the benefit of U.S. Provisional Application Ser. No. 62/712,360, filed Jul. 31, 2018, the disclosure of which is incorporated herein by reference in its entirety.

TECHNICAL FIELD

The present application provides heteroaryl amide compounds that activate the STING pathway to produce interferons, which are useful in the treatment of various diseases including infectious diseases and cancer.

BACKGROUND

The innate immunity is the first line of defense against infection from foreign microorganisms including bacteria, viruses, parasites and other infectious threats, but it also responds to certain danger signals associated with cellular or tissue damage. This response is initiated by activation of so-called pattern recognition receptors that can detect different forms of foreign antigens, i.e. nucleic acids, peptides, carbohydrates, and more, which then lead to production of interferons, proinflammatory chemokines and cytokines, and anti-microbial peptides to fight infection (Palm and Medzhitov, *Immunol Rev* (2009) 227:221-233; Takeuchi and Akira, *Immunol Rev* (2009) 227:75-86; Beutler, *Blood* (2009) 113:1399-1407). STING (stimulator of interferon genes), also known as MITA, MPYS, ERIS, and TMEM173, is one of such pattern recognition receptors in the innate immune response that could detect cytosolic nucleic acids (Ishikawa and Barber, *Nature* (2008) 455:674-678). Direct binding of STING to its ligands induces a conformational change of the complex resulting in a downstream signaling cascade involving TBK1 activation, IRF-3 phosphorylation, and production of type I IFNs and other proinflammatory cytokines, such as TNF, IL-6 and IFNγ (Ishikawa and Barber, *Nature* (2008) 455:674-678).

Type I interferons play a central role in orchestrating host anti-viral response through inhibiting viral replication in infected cells, activating and enhancing antigen presentation and triggering the adaptive immune response through direct and indirect action on T and B cells (McNab et al, *Nat Rev Immunol* (2015) 15:87-103; Crosse et al, *J Innate Immun* (2018) 10:85-93). Therefore, this cytokine acts as a master regulator whose induction in the early stages of viral infection modulates downstream signaling cascades that promote both pro-inflammatory and anti-inflammatory responses. Thus type I IFNs have been evaluated as a therapeutic agent for chronic viral infection such as HCV and HIV (Enomoto and Nishiguchi, *World J Hepatol* (2015) 7:2681-2687; Azzoni et al, *J Infect Dis* (2013) 207:213-222; Lane et al, *Ann Intern Med* (1990) 112:805-11).

The use of type I interferons (IFNs) (the IFNα family and IFNβ) as potential antitumor agents has also been investigated (Kirkwood, *Semin Oncol* (2002) 29:18-26; Tarhini et al, *J Immunol* (2012) 189:3789-3793). IFNs have multiple anticancer mechanisms that include: direct inhibition on tumor cell proliferation and angiogenesis; induction of tumor-specific cytotoxic T cells: plus other immunoregulatory effects on antibody production, natural killer (NK) cell activation, macrophage function, delayed-type hypersensitivity, and major histocompatibility complex antigen expression (Hervas-Stubbs et al, *Clin Cancer Res* (2011) 17:2619-2627; Vannucchi et al, *Curr Med Chem* (2007) 14:667-679) Anticancer activity of type I IFNs has been demonstrated in patients with hematological malignancies (e.g., hairy cell leukemia) and solid tumors (e.g., renal cell carcinoma and malignant melanoma) (Quesada et al, *N Engl J Med* (1984) 310:15-18; Pizzocaro et al, *J Clin Oncol* (2001) 19:425-431; Garbe and Eigentler, *Melanoma Res* (2007) 17:117-127), however, the results and overall efficacy have been modest. This may be due to intrinsic resistance to IFN-induced cell death, to the short half-life (~30 minutes) of intravenously or subcutaneously dosed IFN, to dose-limiting systemic toxicities, and/or to the development of neutralizing antibodies against recombinant IFN protein Thus, the development of an agent like a STING agonist to induce production of type I interferons will be of interest to the field. Currently, there are two different classes of STING agonists: cyclic dinucleotide and small molecule.

Cyclic dinucleotides (CDNs) can directly bind and activate STING, and the complex of bacterial CDN and STING has been confirmed by X-ray crystallography recently (Burdette and Vance, *Nat Immunol* (2013) 14:19-26). In mammalian cells, the primary sensor of cyclic double stranded DNA (dsDNA), namely cyclic GMP-AMP synthetase (cGAS), can convert those cyclic dsDNA into a mammalian CDN cGAMP (cyclic guanosine monophosphate-adenosine monophosphate; Gao et al, *Cell* (2013) 154:748-762). The interaction of cGAMP and STING has also been confirmed by X-ray crystallography (Cai et al, *Mol Cell* (2014) 54:289-296). Synthetic derivatives of cGAMP have been synthesized and showed excellent cellular potency to activate both mouse and human STING in vitro, as well as demonstrated good anti-tumor efficacy in preclinical mouse models (Corrales et al, *Cell Rep* (2015) 11:1018-1030).

Small molecules that can activate STING have also been identified, DMXAA (5,6-dimethylxanthenone-4-acetic acid) and CMA (10-carboxymethyl-9-acridanone) (Perera et al, *J Immunol* (1994) 153:4684-4697; Kramer et al, *Antimicrob Agents Chemother* (1976) 9:233-238).

These two chemically-unrelated compounds can activate the STING pathway, and block multiple viruses from replication (Guo et al, *Agents Chemother* (2015) 59:1273-1281; Cheng et al, *Am J Respir Cell Mol Biol* (2011) 45:480-488). Intriguingly, DMXAA demonstrates excellent anti-tumor activity in preclinical mouse models by priming CD8+ T cells responses to promote rejection of established tumors in a STING-dependent manner, inducing tumor necrosis through disruption of tumor vasculature, as well as augmenting cancer vaccine effect (Corrales et al, *Cell Rep* (2015) 11:1018-1030; Wallace et al, *Cancer Res* (2007) 67:7011-7019; Tang et al, *Plos One* (2013) 8:1-6). Unfortunately, both DMXAA and CMA were found to only bind and activate mouse STING, but not human STING (Caviar et al, *EMBO J*(2013) 32:1440-1450; Kim et al, *ACS Chem Biol* (2013) 8:1396-1401).

Hence, there is a need to develop small molecule entities that can activate human STING and induce upregulation of IRF3 and NFκB pathway, which can later lead to production of interferons and other proinflammatory cytokines and chemokines. This type of immunomodulating agents may be useful not only in infectious disease to activate innate immunity, but also in cancer, and as vaccine adjuvants. This application is directed to this need and others.

SUMMARY

The present invention relates to, inter alia, compounds of Formula (I):

(I)

[chemical structure of Formula (I)]

or a pharmaceutically acceptable salt thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of activating STING, comprising contacting the receptor with a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compounds

The present application provides, inter alia, a compound of Formula (I):

(I)

[chemical structure of Formula (I)]

or a pharmaceutically acceptable salt thereof, wherein:

n is 0 or 1;
m is 0 or 1;
s is 0 or 1;
wherein n+m+s=1 or 2;
when n is 1, then $R^1$ and $R^{1'''}$ are each a bond;
when n is 0, then $R^1$ and $R^{1'''}$ are each independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{1A}$ substituents;

each $R^{1A}$ is independently selected from H, D, halo, CN, $NO_2$, $C_{1-6}$ alkyl, $C_{2-6}$ alkenyl, $C_2$-6 alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^1C(=NR^e)NR^{c1}R^{d1}$, $NHOR^{a1}$, $NR^{c1}S(=O)R^{b1}$, $NR^{c1}S(=O)NR^{c1}R^{d1}$, $S(=O)R^{b1}$, $S(=O)NR^{c1}R^{d1}$, $NR^{c1}S(=O)_2R^{b1}$, $NR^{c1}S(=O)_2NR^{c1}R^{d1}$, $S(=O)_2R^{b1}$, and $S(=O)_2NR^{c1}R^{d1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b1}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{1B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$alkyl, phenyl-$C_{1-4}$ alkyl, 4-7 membered heterocycloalkyl-$C_{1-4}$alkyl, 5-6 membered heteroaryl-$C_{1-4}$alkyl, $OR^{a11}$, $SR^{a11}$, $C(=O)R^{b11}$, $C(=O)NR^{c11}R^{d11}$, $C(=O)OR^{a11}$, $OC(=O)R^{b11}$, $OC(=O)NR^{c11}R^{d11}$, $NR^{c11}R^{d11}$, $NR^{c11}C(=O)R^{b1}$, $NR^{c11}C(=O)OR^{b11}$, $NR^{c11}C(=O)NR^{c11}R^{d11}$, $C(=NR^e)R^{b11}$, $C(=NR^e)NR^{c11}R^{d11}$, $NR^{c11}C(=NR^e)NR^{c11}R^{d11}$, $NHOR^{a11}$, $NR^{c11}S(=O)R^{b11}$, $NR^{c11}S(=O)NR^{c11}R^{d11}$, $S(=O)R^{b11}$, $S(=O)NR^{c11}R^{d11}$, $NR^{c11}S(=O)_2R^{b11}$, $NR^{c11}S(=O)_2NR^{c11}R^{d11}$, $S(=O)_2R^{b11}$, and $S(=O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$alkyl, phenyl-$C_{1-4}$alkyl, 4-7 membered heterocycloalkyl-$C_{1-4}$alkyl, and 5-6 membered heteroaryl-$C_{1-4}$alkyl are each optionally substituted with 1, 2, 3, or 4 independently selected $R^S$ substituents;

each $R^{a11}$, $R^{c11}$, and $R^{d11}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$alkyl, phenyl-$C_{1-4}$ alkyl, 4-7 membered heterocycloalkyl-$C_{1-4}$alkyl, and 5-6 membered heteroaryl-$C_{1-4}$alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$alkyl, phenyl-$C_{1-4}$alkyl, 4-7 membered heterocycloalkyl-$C_{1-4}$alkyl, and 5-6 membered heteroaryl-$C_{1-4}$alkyl are each optionally substituted with 1, 2, 3, or 4 independently selected $R^S$ substituents;

each $R^{b11}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$alkyl, phenyl-$C_{1-4}$alkyl, 4-7 membered heterocycloalkyl-$C_{1-4}$alkyl, and 5-6 membered heteroaryl-$C_{1-4}$alkyl, wherein said $C_{1-6}$ alkyl, $C_{2-6}$ alkenyl, $C_{2-6}$ alkynyl, $C_{1-6}$ haloalkyl, C3 cycloalkyl, phenyl, 4-7 membered heterocycloalkyl, 5-6 membered heteroaryl, $C_{3-7}$ cycloalkyl-$C_{1-4}$alkyl, phenyl-$C_{1-4}$alkyl, 4-7 membered heterocycloalkyl-$C_{1-4}$alkyl, and 5-6 membered heteroaryl-$C_{1-4}$alkyl are each optionally substituted with 1, 2, 3, or 4 independently selected $R^S$ substituents;

$R^2$ is selected from H, $C_{1-4}$alkyl, and $C_{1-4}$ haloalkyl;

$R^{2''}$ is selected from H, $C_{1-4}$alkyl, and $C_{1-4}$ haloalkyl;

$R^3$ and $R^4$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)OR^{b3}$, $NR^{c3}C(=O)NR^{c3}R^{d3}$, $C(=NR^e)R^{b3}$, $C(=NR^e)NR^{c3}R^{d3}$, $NR^{c3}C(=NR^e)NR^{c3}R^{d3}$, $NHOR^{a3}$, $NR^{c3}S(=O)R^{b3}$, $NR^{c3}S(=O)NR^{c3}R^{d3}$, $S(=O)R^{b3}$, $S(=O)NR^{c3}R^{d3}$, $NR^{c3}S(=O)_2R^{b3}$, $NR^{c3}S(=O)_2NR^{c3}R^{d3}$, $S(=O)_2R^{b3}$, and $S(=O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{3A}$ substituents;

each $R^{a3}$, $R^{c3}$, and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{3A}$ substituents;

each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$alkyl are each optionally substituted with 1, 2, 3, or 4 independently selected $R^{3A}$ substituents;

each $R^e$ is independently selected from H, CN, OH, $C_{1-4}$ alkyl, and $C_{1-4}$alkoxy;

each $R^{3A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a31}$, $SR^{a31}$, $C(=O)R^{b31}$, $C(=O)NR^{c31}R^{d31}$, $C(=O)OR^{a31}$, $OC(=O)R^{b31}$, $OC(=O)NR^{c31}R^{d31}$, $NR^{c31}R^{d31}$, $NR^{c31}C(=O)R^{b31}$, $NR^{c31}C(=O)OR^{b31}$, $NR^{c31}C(=O)NR^{c31}R^{d31}$, $C(=NR^e)R^{b31}$, $C(=NR^e)NR^{c31}R^{d31}$, $NR^{c31}C(=NR^e)NR^{c31}R^{d31}$, $NHOR^{a31}$, $NR^{c31}S(=O)R^{b31}$, $NR^{c31}S(=O)NR^{c31}R^{d31}$, $S(=O)R^{b31}$, $S(=O)NR^{c31}R^{d31}$, $NR^{c31}S(=O)_2R^{b31}$, $NR^{c31}S(=O)_2NR^{c31}R^{d31}$, $S(=O)_2R^{b31}$, and $S(=O)_2NR^{c31}R^{d31}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{3B}$ substituents;

each $R^{a31}$, $R^{c31}$, and $R^{d31}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{3B}$ substituents;

each $R^{b31}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{3B}$ substituents;

each $R^{3B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a32}$, $SR^{a32}$, $C(=O)R^{b32}$, $C(=O)NR^{c32}R^{d32}$, $C(=O)OR^{a32}$, $OC(=O)R^{b32}$, $OC(=O)NR^{c32}R^{d32}$, $NR^{c32}R^{d32}$, $NR^{c32}C(=O)R^{b32}$, $NR^{c32}C(=O)OR^{b32}$, $NR^{c32}C(=O)NR^{c32}R^{d32}$, $C(=NR^e)R^{b32}$, $C(=NR^e)NR^{c32}R^{d32}$, $NR^{c32}C(=NR^e)NR^{c32}R^{d32}$, $NHOR^{a32}$, $NR^{c32}S(=O)R^{b32}$, $NR^{c32}S(=O)NR^{c32}R^{d32}$, $S(=O)R^{b32}$, $S(=O)NR^{c32}R^{d32}$, $NR^{c32}S(=O)_2R^{b32}$, $NR^{c32}S(=O)_2NR^{c32}R^{d32}$, $S(=O)_2R^{b32}$, and $S(=O)_2NR^{c32}R^{d32}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{a32}$, $R^{c32}$, and $R^{d32}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{b32}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

Ring C is selected from a phenyl ring, a 5-6 membered heteroaryl ring, a $C_{5-7}$ cycloalkyl ring, and a 5-14 membered heterocycloalkyl ring, each of which is optionally substituted with 1, 2, 3, 4, or 5 independently selected $R^C$ substituents;

each $R^C$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aC}$, $SR^{aC}$, $C(=O)R^{bC}$, $C(=O)NR^{cC}R^{dC}$, $C(=O)OR^{aC}$, $OC(=O)R^{bC}$, $OC(=O)NR^{cC}R^{dC}$, $NR^{cC}R^{dC}$, $NR^{cC}C(=O)R^{bC}$, $NR^{cC}C(=O)OR^{bC}$, $NR^{cC}C(=O)NR^{cC}R^{dC}$, $C(=NR^e)R^{bC}$, $C(=NR^e)NR^{cC}R^{dC}$, $NR^{cC}C(=NR^e)NR^{cC}R^{dC}$, $NHOR^{aC}$, $NR^{cC}S(=O)R^{bC}$, $NR^{cC}S(=O)NR^{cC}R^{dC}$, $S(=O)R^{bC}$, $S(=O)NR^{cC}R^{dC}$, $NR^{cC}S(=O)_2R^{bC}$, $NR^{cC}S(=O)_2NR^{cC}R^{dC}$, $S(=O)_2R^{bC}$, and $S(=O)_2NR^{cC}R^{dC}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{C1}$ substituents;

each $R^{aC}$, $R^{cC}$, and $R^{dC}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{C1}$ substituents;

each $R^{bC}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{C1}$ substituents;

each $R^{C1}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aC1}$, $SR^{aC1}$, $C(=O)R^{bC1}$, $C(=O)NR^{cC1}R^{dC1}$, $C(=O)OR^{aC1}$, $OC(=O)R^{bC1}$, $OC(=O)NR^{cC1}R^{dC1}$, $NR^{cC1}R^{dC1}$, $NR^{cC1}C(=O)R^{bC1}$, $NR^{cC1}C(=O)OR^{bC1}$, $NR^{cC1}C(=O)NR^{cC1}R^{dC1}$, $C(=NR^e)R^{bC1}$, $C(=NR^e)NR^{cC1}R^{dC1}$, $NR^{cC1}C(=NR^e)NR^{cC1}R^{dC1}$, $NHOR^{aC1}$, $NR^{cC1}S(=O)R^{bC1}$, $NR^{cC1}S(=O)NR^{cC1}R^{dC1}$, $S(=O)R^{bC1}$, $S(=O)NR^{cC1}R^{dC1}$, $NR^{cC1}S(=O)_2R^{bC1}$, $NR^{cC1}S(=O)_2NR^{cC1}R^{dC1}$, $S(=O)_2R^{bC1}$, and $S(=O)_2NR^{cC1}R^{dC1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C2}$ substituents;

each $R^{aC1}$, $R^{cC1}$, and $R^{dC1}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C2}$ substituents;

each $R^{bC1}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C2}$ substituents;

each $R^{C2}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aC2}$, $SR^{aC2}$, $C(=O)R^{bC2}$, $C(=O)NR^{cC2}R^{dC2}$, $C(=O)OR^{aC2}$, $OC(=O)R^{bC2}$, $OC(=O)NR^{cC2}R^{dC2}$, $NR^{cC2}R^{dC2}$, $NR^{cC2}C(=O)R^{bC2}$, $NR^{cC2}C(=O)OR^{bC2}$, $NR^{cC2}C(=O)NR^{cC2}R^{dC2}$, $C(=NR^e)R^{bC2}$, $C(=NR^e)NR^{cC2}R^{dC2}$, $NR^{cC2}C(=NR^e)NR^{cC2}R^{dC2}$, $NHOR^{aC2}$, $NR^{cC2}S(=O)R^{bC2}$, $NR^{cC2}S(=O)NR^{cC2}R^{dC2}$, $S(=O)R^{bC2}$, $S(=O)NR^{cC2}R^{dC2}$, $NR^{cC2}S(=O)_2R^{bC2}$, $NR^{cC2}S(=O)_2NR^{cC2}R^{dC2}$, $S(=O)_2R^{bC2}$, and $S(=O)_2NR^{cC2}R^{dC2}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{aC2}$, $R^{cC2}$, and $R^{dC2}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{bC2}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

---- is a divalent ring forming moiety formed by $R^5$ and $R^6$, which may be present or absent;

$R^5$, $R^6$, $R^7$, and $R^8$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^e)R^{b5}$, $C(=NR^e)NR^{c5}R^{d5}$, $NR^{c5}C(=NR^e)NR^{c5}R^{d5}$, $NHOR^{a5}$, $NR^{c5}S(=O)R^{b5}$, $NR^{c5}S(=O)NR^{c5}R^{d5}$, $S(=O)R^{b5}$, $S(=O)NR^{c5}R^{d5}$, $NR^{c5}S(=O)_2R^{b5}$, $NR^{c5}S(=O)_2NR^{c5}R^{d5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

or, when ---- is present, then $R^5$ and $R^6$ together with the carbon atoms to which they are attached, form ring D, which is selected from a phenyl ring, 5-6 membered heteroaryl ring, a $C_{5-7}$ cycloalkyl ring, and a 5-14 heterocycloalkyl ring, each of which is optionally substituted with 1, 2, 3, 4, or 5 independently selected $R^D$ substituents;

or, when ---- is absent and s is 1, then $R^5$ and one of $R^C$ taken together form a linking group $L^3$;

each $R^{a5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

each $R^{b5}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

each $R^{5A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a51}$, $SR^{a51}$, $C(=O)R^{b51}$, $C(=O)NR^{c51}R^{d51}$, $C(=O)OR^{a51}$, $OC(=O)R^{b51}$, $OC(=O)NR^{c51}R^{d51}$, $NR^{c51}R^{d51}$, $NR^{c51}C(=O)R^{b51}$, $NR^{c51}C(=O)OR^{b51}$, $NR^{c51}C(=O)NR^{c51}R^{d51}$, $C(=NR^e)R^{b51}$, $C(=NR^e)NR^{c51}R^{d51}$, $NR^{c51}C(=NR^e)NR^{c51}R^{d51}$, $NHOR^{a51}$, $NR^{c51}S(=O)R^{b51}$, $NR^{c51}S(=O)NR^{c51}R^{d51}$, $S(=O)R^{b51}$, $S(=O)NR^{c51}R^{d51}$, $NR^{c51}S(=O)_2R^{b51}$, $NR^{c51}S(=O)_2NR^{c51}R^{d51}$, $S(=O)_2R^{b51}$, and $S(=O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{b51}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{5B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a52}$, $SR^{a52}$, $C(=O)R^{b52}$, $C(=O)NR^{c52}R^{d52}$, $C(=O)OR^{a52}$, $OC(=O)R^{b52}$, $OC(=O)NR^{c52}R^{d52}$, $NR^{c52}R^{d52}$, $NR^{c52}C(=O)R^{b52}$, $NR^{c52}C(=O)OR^{b52}$, $NR^{c52}C(=O)NR^{c52}R^{d52}$, $C(=NR^e)R^{b52}$, $C(=NR^e)NR^{c52}R^{d52}$, $NR^{c52}C(=NR^e)NR^{c52}R^{d52}$, $NHOR^{a52}$, $NR^{c52}S(=O)R^{b52}$, $NR^{c52}S(=O)NR^{c52}R^{d52}$, $S(=O)R^{b52}$, $S(=O)NR^{c52}R^{d52}$, $NR^{c52}S(=O)_2R^{b52}$, $NR^{c52}S(=O)_2NR^{c52}R^{d52}$, $S(=O)_2R^{b52}$, and $S(=O)_2NR^{c52}R^{d52}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{a52}$, $R^{c52}$, and $R^{d52}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{b52}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^D$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aD}$, $SR^{aD}$, $C(=O)R^{bD}$, $C(=O)NR^{cD}R^{dD}$, $C(=O)OR^{aD}$, $OC(=O)R^{bD}$, $OC(=O)NR^{cD}R^{dD}$, $NR^{cD}R^{dD}$, $NR^{cD}C(=O)R^{bD}$, $NR^{cD}C(=O)OR^{aD}$, $NR^{cD}C(=O)NR^{cD}R^{dD}$, $C(=NR^e)R^{bD}$, $C(=NR^e)NR^{cD}R^{dD}$, $NR^{cD}C(=NR^e)NR^{cD}R^{dD}$, $NHOR^{aD}$, $NR^{cD}S(=O)R^{bD}$, $NR^{cD}S(=O)NR^{cD}R^{dD}$, $S(=O)R^{bD}$, $S(=O)NR^{cD}R^{dD}$, $NR^{cD}S(=O)_2R^{bD}$, $NR^{cD}S(=O)_2NR^{cD}R^{dD}$, $S(=O)_2R^{bD}$, and $S(=O)_2NR^{cD}R^{dD}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^m$ substituents;

or, when ---- is present and s is 1, then one of $R^D$ and one of $R^C$ taken together form a linking group $L^3$;

each $R^{aD}$, $R^{cD}$, and $R^{dD}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^m$ substituents;

each $R^{bD}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$alkyl are each optionally substituted with 1, 2, 3, or 4 independently selected $R^m$ substituents;

each $R^{D1}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aD1}$, $SR^{aD1}$, $C(=O)R^{bD1}$, $C(=O)NR^{cD1}R^{dD1}$, $C(=O)OR^{aD1}$, $OC(=O)R^{bD1}$, $OC(=O)NR^{cD1}R^{dD1}$, $NR^{cD1}R^{dD1}$, $NR^{cD1}C(=O)R^{bD1}$, $NR^{cD1}C(=O)OR^{bD1}$, $NR^{cD1}C(=O)NR^{cD1}R^{dD1}$, $C(=NR^e)R^{bD1}$, $C(=NR^e)NR^{cD1}R^{dD1}$, $NR^{cD1}C(=NR^e)NR^{cD1}R^{dD1}$, $NHOR^{aD1}$, $NR^{cD1}S(=O)R^{bD1}$, $NR^{cD1}S(=O)NR^{cD1}R^{dD1}$, $S(=O)R^{bD1}$, $S(=O)NR^{cD1}R^{dD1}$, $NR^{cD1}S(=O)_2R^{bD1}$, $NR^{cD1}S(=O)_2NR^{cD1}R^{dD1}$, $S(=O)_2R^{bD1}$, and $S(=O)_2NR^{cD1}R^{dD1}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{D2}$ substituents;

each $R^{aD1}$, $R^{cD1}$, and $R^{dD1}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{D2}$ substituents;

each $R^{bD1}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{D2}$ substituents;

each $R^{D2}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aD2}$, $SR^{aD2}$, $C(=O)R^{bD2}$, $C(=O)NR^{cD2}R^{dD2}$, $C(=O)OR^{aD2}$, $OC(=O)R^{bD2}$, $OC(=O)NR^{cD2}R^{dD2}$, $NR^{cD2}R^{dD2}$, $NR^{cD2}C(=O)R^{bD2}$, $NR^{cD2}C(=O)OR^{bD2}$, $NR^{cD2}C(=O)NR^{cD2}R^{dD2}$, $C(=NR^e)R^{bD2}$, $C(=NR^e)NR^{cD2}R^{dD2}$, $NR^{cD2}C(=NR^e)NR^{cD2}R^{dD2}$, $NHOR^{aD2}$, $NR^{cD2}S(=O)R^{bD2}$, $NR^{cD2}S(=O)NR^{cD2}R^{dD2}$, $S(=O)R^{bD2}$, $S(=O)NR^{cD2}R^{dD2}$, $NR^{cD2}S(=O)_2R^{bD2}$, $NR^{cD2}S(=O)_2NR^{cD2}R^{dD2}$, $S(=O)_2R^{bD2}$, and $S(=O)_2NR^{cD2}R^{dD2}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{aD2}$, $R^{cD2}$, and $R^{dD2}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{bD2}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

Ring moiety A is selected from $C_{3-10}$ cycloalkyl, $C_{6-10}$ aryl, 4-10 membered heterocycloalkyl, and 5-10 membered heteroaryl, each of which is optionally substituted with 1, 2, 3, 4, or 5 independently selected $R^A$ substituents;

Ring moiety B is selected from $C_{3-10}$ cycloalkyl, $C_{6-10}$ aryl, 4-10 membered heterocycloalkyl, and 5-10 membered heteroaryl, each of which is optionally substituted with 1, 2, 3, 4, or 5 independently selected $R^B$ substituents;

each $R^A$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aA}$, $SR^{aA}$, $C(=O)R^{bA}$, $C(=O)NR^{cA}R^{dA}$, $C(=O)OR^{aA}$, $OC(=O)R^{bA}$, $OC(=O)NR^{cA}R^{dA}$, $NR^{cA}R^{dA}$, $NR^{cA}C(=O)R^{bA}$, $NR^{cA}C(=O)OR^{bA}$, $NR^{cA}C(=O)NR^{cA}R^{dA}$, $C(=NR^e)R^{bA}$, $C(=NR^e)NR^{cA}R^{dA}$, $NR^{cA}C(=NR^e)NR^{cA}R^{dA}$, $NHOR^{aA}$, $NR^{cA}S(=O)R^{bA}$, $NR^{cA}S(=O)NR^{cA}R^{dA}$, $S(=O)R^{bA}$, $S(=O)NR^{cA}R^{dA}$, $NR^{cA}S(=O)_2R^{bA}$, $NR^{cA}S(=O)_2NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9A}$ substituents;

each $R^B$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aB}$, $SR^{aB}$, $C(=O)R^{bB}$, $C(=O)NR^{cB}R^{dB}$, $C(=O)OR^{aB}$, $OC(=O)R^{bB}$, $OC(=O)NR^{cB}R^{dB}$, $NR^{cB}R^{dB}$, $NR^{cB}C(=O)R^{bB}$, $NR^{cB}C(=O)OR^{bB}$, $NR^{cB}C(=O)NR^{cB}R^{dB}$, $C(=NR^e)R^{bB}$, $C(=NR^e)NR^{cB}R^{dB}$, $NR^{cB}C(=NR^e)NR^{cB}R^{dB}$, $NHOR^{aB}$, $NR^{cB}S(=O)R^{bB}$, $NR^{cB}S(=O)NR^{cB}R^{dB}$, $S(=O)R^{bB}$, $S(=O)NR^{cB}R^{dB}$, $NR^{cB}S(=O)_2R^{bB}$, $NR^{cB}S(=O)_2NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9B}$ substituents;

provided that when $R^A$ is attached to a nitrogen atom of the ring moiety A, then $R^A$ is selected from H, CN, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $C(=O)R^{bA}$, $C(=O)NR^{cA}R^{dA}$, $C(=O)OR^{aA}$, $C(=NR^e)R^{bA}$, $C(=NR^e)NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9A}$ substituents;

provided that when $R^B$ is attached to a nitrogen atom of the ring moiety B, then $R^B$ is selected from H, CN, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $C(=O)R^{bB}$, $C(=O)NR^{cB}R^{dB}$, $C(=O)OR^{aB}$, $C(=NR^e)R^{bB}$, $C(=NR^e)NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9B}$ substituents;

provided that when m is 1, then one of $R^A$ and one of $R^B$ taken together form a linking group $L^2$;

each $R^{aA}$, $R^{cA}$, and $R^{dA}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

each $R^{bA}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$alkyl are each optionally substituted with 1, 2, 3, or 4 independently selected $R^{9A}$ substituents;

each $R^{aB}$, $R^{cB}$, and $R^{dB}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9B}$ substituents;

each $R^{bB}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9B}$ substituents;

each $R^{9A}$ and $R^{9B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $C(=NR^e)NR^{c9}R^{d9}$, $NR^{c9}C(=NR^e)NR^{c9}R^{d9}$, $NHOR^{a9}$, $NR^{c9}S(=O)R^{b9}$, $NR^{c9}S(=O)NR^{c9}R^{d9}$, $S(=O)R^{b9}$, $S(=O)NR^{c9}R^{d9}$, $NR^{c9}S(=O)_2R^{b9}$, $NR^{c9}S(=O)_2NR^{c9}R^{d9}$, $S(=O)_2R^{b9}$, and $S(=O)_2NR^{c9}R^{d9}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{a9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{b9}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

$L^1$, $L^2$, and $L^3$ are each independently selected from —R—R—, —R—R—R—, -Cy-, —R-Cy-, -Cy-R—, —R-Cy-R—, —R—R-Cy-, -Cy-R—R—, and -Cy-R-Cy-;

each R is independently selected from M, $C_{1-6}$ alkylene, $C_{2-6}$ alkenylene, $C_{2-6}$ alkynylene, $C_{1-6}$ alkylene-M, M-$C_{1-6}$ alkylene, $C_{1-6}$ alkylene-M-$C_{1-6}$ alkylene, M-$C_{1-6}$ alkylene-M, $C_{2-6}$ alkenylene-M, M-$C_{2-6}$ alkenylene, $C_{2-6}$ alkenylene-M-$C_{2-6}$ alkenylene, M-$C_{2-6}$ alkenylene-M, $C_{2-6}$ alkynylene-M, M-$C_{2-6}$ alkynylene, $C_{2-6}$ alkynylene-M-$C_{2-6}$ alkynylene, and M-$C_{2-6}$ alkynylene-M, wherein each of said $C_{1-6}$ alkylene, $C_{2-6}$ alkenylene, and $C_{2-6}$ alkynylene is optionally substituted with 1, 2, 3, or 4 substituents independently selected $R^S$ substituents;

each Cy is independently selected from $C_{3-14}$ cycloalkyl, phenyl, 4-14 membered heterocycloalkyl, and 5-6 membered heteroaryl, each of which is optionally substituted with 1, 2, 3, or 4 independently selected $R^S$ substituents;

each M is independently selected from —O—, —S—, —C(O)—, —C(O)$NR^L$—, —C(O)O—, —OC(O)—, —OC(O)$NR^L$—, —$NR^L$—, —$NR^L$C(O)—, —$NR^L$C(O)O—, —$NR^L$C(O)$NR^L$—, —$NR^L$S(O)$_2$—, —S(O)$_2$—, —S(O)$_2$$NR^L$—, and —$NR^L$S(O)$_2$$NR^L$—; provided that when M is attached to a nitrogen atom, then M is selected from —C(O)—, —C(O)$NR^L$—, —C(O)O—, —S(O)$_2$—, and —S(O)$_2$$NR^L$—;

each $R^L$ is independently selected from H, $C_{1-3}$ alkyl, $C_{2-3}$ alkenyl, $C_{2-3}$ alkynyl, and $C_{1-3}$ haloalkyl; and each $R^S$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$alkoxy-$C_{1-3}$ alkyl, $C_{3-7}$ cycloalkyl, $C_{1-3}$ alkoxy, $C_{1-3}$ haloalkoxy, amino, $C_{1-3}$alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$alkylcarbamyl, di($C_{1-3}$alkyl) carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$alkylaminocarbonyloxy, $C_{1-3}$alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$alkyl)aminosulfonylamino, aminocarbonylamino, $C_{1-3}$ alkylaminocarbonylamino, and di($C_{1-3}$alkyl)aminocarbonylamino.

In some embodiments, the compound is a compound of Formula (III), as defined infra, wherein:

$R^2$ is selected from H, $C_{1-4}$ alkyl, and $C_{1-4}$ haloalkyl;

$R^{2'}$ is selected from H, $C_{1-4}$ alkyl, and $C_{1-4}$ haloalkyl;

$R^3$ and $R^4$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)OR^{b3}$, $NR^{c3}C(=O)NR^{c3}R^{d3}$, $C(=NR^e)R^{b3}$, $C(=NR^e)NR^{c3}R^{d3}$, $NR^{c3}C(=NR^e)NR^{c3}R^{d3}$, $NHOR^{a3}$, $NR^{c3}S(=O)R^{b3}$, $NR^{c3}S(=O)NR^{c3}R^{d3}$, $S(=O)R^{b3}$, $S(=O)NR^{c3}R^{d3}$, $NR^{c3}S(=O)_2R^{b3}$, $NR^{c3}S(=O)_2NR^{c3}R^{d3}$, $S(=O)_2R^{b3}$, and $S(=O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{3A}$ substituents;

each $R^{a3}$, $R^{c3}$, and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{3A}$ substituents;

each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$alkyl are each optionally substituted with 1, 2, 3, or 4 independently selected $R^{3A}$ substituents;

each $R^e$ is independently selected from H, CN, OH, $C_{1-4}$ alkyl, and $C_{1-4}$alkoxy;

each $R^{3A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a31}$, $SR^{a31}$, $C(=O)R^{b31}$, $C(=O)NR^{c31}R^{d31}$, $C(=O)OR^{a31}$, $OC(=O)R^{b31}$, $OC(=O)NR^{c31}R^{d31}$, $NR^{c31}R^{d31}$, $NR^{c31}C(=O)R^{b31}$, $NR^{c31}C(=O)OR^{b31}$, $NR^{c31}C(=O)NR^{c31}R^{d31}$, $C(=NR^e)R^{b31}$, $C(=NR^e)NR^{c31}R^{d31}$, $NR^{c31}C(=NR^e)NR^{c31}R^{d31}$, $NHOR^{a31}$, $NR^{c31}S(=O)R^{b31}$, $NR^{c31}S(=O)NR^{c31}R^{d31}$, $S(=O)R^{b31}$, $S(=O)NR^{c31}R^{b31}$, $NR^{c31}S(=O)_2R^{b31}$, $NR^{c31}S(=O)_2NR^{c31}R^{d31}$, $S(=O)_2R^{b31}$, and $S(=O)_2NR^{c31}R^{d31}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{3B}$ substituents;

each $R^{a31}$, $R^{c31}$, and $R^{d31}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{3B}$ substituents;

each $R^{b31}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{3B}$ substituents;

each $R^{3B}$ is independently selected from H, halo, CN, OH, $NO_2$, COOH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$haloalkoxy, amino, $C_{1-6}$alkylamino, di($C_{1-6}$ alkyl)amino, $C_{1-6}$alkylsulfonyl, carbamyl, $C_{1-6}$alkylcarbamyl, di($C_{1-6}$alkyl)carbamyl, $C_{1-6}$ alkylcarbonyl, and $C_{1-6}$alkoxycarbonyl;

Ring C is selected from a phenyl ring, a 5-6 membered heteroaryl ring, a $C_{5-7}$ cycloalkyl ring, and a 5-14 membered heterocycloalkyl ring, which is optionally substituted with 1, 2, 3, 4, or 5 independently selected $R^C$ substituents;

each $R^C$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aC}$, $SR^{aC}$, $C(=O)R^{bC}$, $C(=O)NR^{cC}R^{dC}$, $C(=O)OR^{aC}$, $OC(=O)R^{bC}$, $OC(=O)NR^{cC}R^{dC}$, $NR^{cC}R^{dC}$, $NR^{cC}C(=O)R^{bC}$, $NR^{cC}C(=O)OR^{bC}$, $NR^{cC}C(=O)NR^{cC}R^{dC}$, $C(=NR^e)R^{bC}$, $C(=NR^e)NR^{cC}R^{dC}$, $NR^{cC}C(=NR^e)NR^{cC}R^{dC}$, $NHOR^{aC}$, $NR^{cC}S(=O)R^{bC}$, $NR^{cC}S(=O)NR^{cC}R^{dC}$, $S(=O)R^{bC}$, $S(=O)NR^{cC}R^{dC}$, $NR^{cC}S(=O)_2R^{bC}$, $NR^{cC}S(=O)_2NR^{cC}R^{dC}$, $S(=O)_2R^{bC}$, and $S(=O)_2NR^{cC}R^{dC}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{C1}$ substituents;

each $R^{aC}$, $R^{cC}$, and $R^{dC}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{C1}$ substituents;

each $R^{bC}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$alkyl are each optionally substituted with 1, 2, 3, or 4 independently selected $R^{C1}$ substituents;

each $R^{C1}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aC1}$, $SR^{aC1}$, $C(=O)R^{bC1}$, $C(=O)NR^{cC1}R^{dC1}$, $C(=O)OR^{aC1}$, $OC(=O)R^{bC1}$, $OC(=O)NR^{cC1}R^{dC1}$, $NR^{cC1}R^{dC1}$, $NR^{cC1}C(=O)R^{bC1}$, $NR^{cC1}C(=O)OR^{bC1}$, $NR^{cC1}C(=O)NR^{cC1}R^{dC1}$, $C(=NR^e)R^{bC1}$, $C(=NR^e)NR^{cC1}R^{dC1}$, $NR^{cC1}C(=NR^e)NR^{cC1}R^{dC1}$, $NHOR^{aC1}$, $NR^{cC1}S(=O)R^{bC1}$, $NR^{cC1}S(=O)NR^{cC1}R^{dC1}$, $S(=O)R^{bC1}$, $S(=O)NR^{cC1}R^{dC1}$, $NR^{cC1}S(=O)_2R^{bC1}$, $NR^{cC1}S(=O)_2NR^{cC1}R^{dC1}$, $S(=O)_2R^{bC1}$, and $S(=O)_2NR^{cC1}R^{dC1}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C2}$ substituents;

each $R^{aC1}$, $R^{cC1}$, and $R^{dC1}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C2}$ substituents;

each $R^{bC1}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C2}$ substituents;

each $R^{C2}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aC2}$, $SR^{aC2}$, $C(=O)R^{bC2}$, $C(=O)NR^{cC2}R^{dC2}$, $C(=O)OR^{aC2}$, $OC(=O)R^{bC2}$, $OC(=O)NR^{cC2}R^{dC2}$, $NR^{cC2}R^{dC2}$, $NR^{cC2}C(=O)R^{bC2}$, $NR^{cC2}C(=O)OR^{bC2}$, $NR^{cC2}C(=O)NR^{cC2}R^{dC2}$, $C(=NR^e)R^{bC2}$, $C(=NR^e)NR^{cC2}R^{dC2}$, $NR^{cC2}C(=NR^e)NR^{cC2}R^{dC2}$, $NHOR^{aC2}$, $NR^{cC2}S(=O)R^{bC2}$, $NR^{cC2}S(=O)NR^{cC2}R^{dC2}$, $S(=O)R^{bC2}$, $S(=O)NR^{cC2}R^{dC2}$, $NR^{cC2}S(=O)_2R^{bC2}$, $NR^{cC2}S(=O)_2NR^{cC2}R^{dC2}$, $S(=O)_2R^{bC2}$, and $S(=O)_2NR^{cC2}R^{dC2}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{aC2}$, $R^{cC2}$, and $R^{dC2}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{bC2}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

$R^5$, $R^6$, $R^7$, and $R^8$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^e)R^{b5}$, $C(=NR^e)NR^{c5}R^{d5}$, $NR^{c5}C(=NR^e)NR^{c5}R^{d5}$, $NHOR^{a5}$, $NR^{c5}S(=O)R^{b5}$, $NR^{c5}S(=O)NR^{c5}R^{d5}$, $S(=O)R^{b5}$, $S(=O)NR^{c5}R^{d5}$, $NR^{c5}S(=O)_2R^{b5}$, $NR^{c5}S(=O)_2NR^{c5}R^{d5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

each $R^{a5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

each $R^{b5}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

each $R^{5A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $C(=O)R^{b51}$, $C(=O)NR^{c51}R^{d51}$, $C(=O)OR^{a51}$, $OC(=O)R^{b51}$, $OC(=O)NR^{c51}R^{d51}$, $NR^{c51}R^{d51}$, $NR^{c51}C(=O)R^{b51}$, $NR^{c51}C(=O)OR^{b51}$, $NR^{c51}C(=O)NR^{c51}R^{d51}$, $C(=NR^e)R^{b51}$, $C(=NR^e)NR^{c51}R^{d51}$, $NR^{c51}C(=NR^e)NR^{c51}R^{d51}$, $NHOR^{a51}$, $NR^{c51}S(=O)R^{b51}$, $NR^{c51}S(=O)NR^{c51}R^{d51}$, $S(=O)R^{b51}$, $S(=O)NR^{c51}R^{d51}$, $NR^{c51}S(=O)_2R^{b51}$, $NR^{c51}S(=O)_2NR^{c51}R^{d51}$, $S(=O)_2R^{b51}$, and $S(=O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{5B}$ is independently selected from H, halo, CN, OH, $NO_2$, COOH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$haloalkoxy, amino, $C_{1-6}$alkylamino, di($C_{1-6}$ alkyl)amino, $C_{1-6}$alkylsulfonyl, carbamyl, $C_{1-6}$alkylcarbamyl, di($C_{1-6}$alkyl)carbamyl, $C_{1-6}$ alkylcarbonyl, and $C_{1-6}$alkoxycarbonyl;

Ring moiety A is selected from $C_{3-10}$ cycloalkyl, $C_{6-10}$ aryl, 4-10 membered heterocycloalkyl, and 5-10 membered heteroaryl, each of which is optionally substituted with 1, 2, 3, 4, or 5 independently selected $R^A$ substituents;

Ring moiety B is selected from $C_{3-10}$ cycloalkyl, $C_{6-10}$ aryl, 4-10 membered heterocycloalkyl, and 5-10 membered heteroaryl, each of which is optionally substituted with 1, 2, 3, 4, or 5 independently selected $R^B$ substituents;

each $R^A$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aA}$, $SR^{aA}$, $C(=O)R^{bA}$, $C(=O)NR^{cA}R^{dA}$, $C(=O)OR^{aA}$, $OC(=O)R^{bA}$, $OC(=O)NR^{cA}R^{dA}$, $NR^{cA}R^{dA}$, $NR^{cA}C(=O)R^{bA}$, $NR^{cA}C(=O)OR^{bA}$, $NR^{cA}C(=O)NR^{cA}R^{dA}$, $C(=NR^e)R^{bA}$, $C(=NR^e)NR^{cA}R^{dA}$, $NR^{cA}C(=NR^e)NR^{cA}R^{dA}$, $NHOR^{aA}$, $NR^{cA}S(=O)R^{bA}$, $NR^{cA}S(=O)NR^{cA}R^{dA}$, $S(=O)R^{bA}$, $S(=O)NR^{cA}R^{dA}$, $NR^{cA}S(=O)_2R^{bA}$, $NR^{cA}S(=O)_2NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9A}$ substituents;

each $R^B$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aB}$, $SR^{aB}$, $C(=O)R^{bB}$, $C(=O)NR^{cB}R^{dB}$, $C(=O)OR^{aB}$, $OC(=O)R^{bB}$, $OC(=O)NR^{cB}R^{dB}$, $NR^{cB}R^{dB}$, $NR^{cB}C(=O)R^{bB}$, $NR^{cB}C(=O)OR^{bB}$, $NR^{cB}C(=O)NR^{cB}R^{dB}$, $C(=NR^e)R^{bB}$, $C(=NR^e)NR^{cB}R^{dB}$, $NR^{cB}C(=NR^e)NR^{cB}R^{dB}$, $NHOR^{aB}$, $NR^{cB}S(=O)R^{bB}$, $NR^{cB}S(=O)NR^{cB}R^{dB}$, $S(=O)R^{bB}$, $S(=O)NR^{cB}R^{dB}$, $NR^{cB}S(=O)_2R^{bB}$, $NR^{cB}S(=O)_2NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9B}$ substituents;

provided that when $R^A$ is attached to a nitrogen atom of the ring moiety A, then $R^A$ is selected from H, CN, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $C(=O)R^{bA}$, $C(=O)NR^{cA}R^{dA}$, $C(=O)OR^{aA}$, $C(=NR^e)R^{bA}$, $C(=NR^e)NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9A}$ substituents;

provided that when $R^B$ is attached to a nitrogen atom of the ring moiety B, then $R^B$ is selected from H, CN, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $C(=O)R^{bB}$, $C(=O)NR^{cB}R^{dB}$, $C(=O)OR^{aB}$, $C(=NR^e)R^{bB}$, $C(=NR^e)NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9B}$ substituents;

each $R^{aA}$, $R^{cA}$, and $R^{dA}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$alkyl, $C_{6-10}$ aryl-$C_{1-4}$alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

each $R^{bA}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

each $R^{aB}$, $R^{cB}$, and $R^{dB}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9B}$ substituents;

each $R^{bB}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$alkyl are each optionally substituted with 1, 2, 3, or 4 independently selected $R^{9B}$ substituents;

each $R^{9A}$ and $R^{9B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C(=O)NR^{c9}R^{d9}$, $C(=NR^e)R^{b9}$, $C(=NR^e)NR^{c9}R^{d9}$, $NR^{c9}C(=NR^e)NR^{c9}R^{d9}$, $NHOR^{a9}$, $NR^{c9}S(=O)R^{b9}$, $NR^{c9}S(=O)NR^{c9}R^{d9}$, $S(=O)R^{b9}$, $S(=O)NR^{c9}R^{d9}$, $NR^{c9}S(=O)_2R^{b9}$, $NR^{c9}S(=O)_2NR^{c9}R^{d9}$, $S(=O)_2 R^{b9}$, and $S(=O)_2NR^{c9}R^{d9}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{a9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{b9}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

$L^1$ is selected from —R—R—, —R—R—R—, -Cy-, —R-Cy-, -Cy-R—, —R-Cy-R—, —R—R-Cy-, -Cy-R—R—, and -Cy-R-Cy-;

each R is independently selected from M, $C_{1-6}$ alkylene, $C_{2-6}$ alkenylene, $C_{2-6}$ alkynylene, $C_{1-6}$ alkylene-M, M-$C_{1-6}$ alkylene, $C_{1-6}$ alkylene-M-$C_{1-6}$ alkylene, M-$C_{1-6}$ alkylene-M, $C_{2-6}$ alkenylene-M, M-$C_{2-6}$ alkenylene, $C_{2-6}$ alkenylene-M-$C_{2-6}$ alkenylene, M-$C_{2-6}$ alkenylene-M, $C_{2-6}$ alkynylene-M, M-$C_{2-6}$ alkynylene, $C_{2-6}$ alkynylene-M-$C_{2-6}$ alkynylene, and M-$C_{2-6}$ alkynylene-M, wherein each of said $C_{1-6}$ alkylene, $C_{2-6}$ alkenylene, and $C_{2-6}$ alkynylene is optionally substituted with 1, 2, 3, or 4 substituents independently selected $R^S$ substituents;

each Cy is independently selected from $C_{3-14}$ cycloalkyl, phenyl, 4-14 membered heterocycloalkyl, and 5-6 membered heteroaryl, each of which is optionally substituted with 1, 2, 3, or 4 independently selected $R^S$ substituents;

each M is independently selected from —O—, —S—, —C(O)—, —C(O)NR$^L$—, —C(O)O—, —OC(O)—, —OC(O)NR$^L$—, —NR$^L$—, —NR$^L$C(O)—, —NR$^L$C(O)O—, —NR$^L$C(O)NR$^L$—, —NR$^L$S(O)$_2$—, —S(O)$_2$—, —S(O)$_2$NR$^L$—, and —NR$^L$S(O)$_2$NR$^L$—; provided that when M is attached to a nitrogen atom, then M is selected from —C(O)—, —C(O)NR$^L$—, —C(O)O—, —S(O)$_2$—, and —S(O)$_2$NR$^L$—;

each R$^L$ is independently selected from H, C$_{1-3}$ alkyl, C$_{2-3}$ alkenyl, C$_{2-3}$ alkynyl, and C$_{1-3}$ haloalkyl; and each R$^S$ is independently selected from OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$alkoxy-C$_{1-3}$ alkyl, C$_{3-7}$ cycloalkyl, C$_{1-3}$ alkoxy, C$_{1-3}$ haloalkoxy, amino, C$_{1-3}$alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$alkylcarbamyl, di(C$_{1-3}$alkyl)carbamyl, carboxy, C$_{1-3}$ alkylcarbonyl, C$_{1-3}$ alkoxycarbonyl, C$_{1-3}$ alkylcarbonyloxy, C$_{1-3}$ alkylcarbonylamino, C$_{1-3}$ alkoxycarbonylamino, C$_{1-3}$alkylaminocarbonyloxy, C$_{1-3}$alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$alkyl)aminosulfonylamino, aminocarbonylamino, C$_{1-3}$ alkylaminocarbonylamino, and di(C$_{1-3}$alkyl)aminocarbonylamino.

In some embodiments, when n is 0, then R$^1$ and R$^{1''}$ are each independently selected from H, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{1A}$ substituents.

In some embodiments, when n is 0, then R$^1$ and R$^{1''}$ are each independently selected from H, C$_{1-6}$ alkyl, C$_{2-6}$ alkenyl, C$_{2-6}$ alkynyl, and C$_{1-6}$ haloalkyl, wherein said C$_{1-6}$ alkyl, C$_{2-6}$ alkenyl, C$_{2-6}$ alkynyl, and C$_{1-6}$ haloalkyl are each optionally substituted with 1, 2, 3, or 4 independently selected R$^{1A}$ substituents.

In some embodiments, when n is 0, then R$^1$ and R$^{1''}$ are each independently selected from H, C$_{1-6}$ alkyl, and C$_{1-6}$ haloalkyl.

In some embodiments, when n is 0, then R$^1$ and R$^{1''}$ are each H.

In some embodiments, each R$^{1A}$ is independently selected from halo, CN, OH, NO$_2$, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$alkoxy-C$_{1-6}$ alkyl, C$_{1-6}$alkoxy, C$_{1-6}$ haloalkoxy, amino, C$_{1-6}$alkylamino, di(C$_{1-6}$alkyl)amino, thio, C$_{1-6}$ alkylthio, C$_{1-6}$ alkylsulfonyl, carbamyl, C$_{1-6}$alkylcarbamyl, di(C$_{1-6}$alkyl)carbamyl, carboxy, C$_{1-6}$ alkylcarbonyl, C$_{1-6}$alkoxycarbonyl, C$_{1-6}$alkylcarbonyloxy, C$_{1-6}$alkylcarbonylamino, C$_{1-6}$alkoxycarbonylamino, C$_{1-6}$ alkylaminocarbonyloxy. C$_{1-6}$alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$alkyl)aminocarbonylamino.

In some embodiments, each R$^{1A}$ is independently selected from H, halo, CN, OH, C$_{1-6}$ alkyl, C$_{2-6}$ alkenyl, C$_{2-6}$ alkynyl, C$_{1-6}$ haloalkyl, C$_{1-6}$alkoxy, C$_{1-6}$haloalkoxy, amino, C$_{1-6}$ alkylamino, and di(C$_{1-6}$alkyl)amino.

In some embodiments, R$^2$ is H or C$_{1-4}$ alkyl.

In some embodiments, R$^2$ is H.

In some embodiments, R$^2$ is H or C$_{1-4}$ alkyl.

In some embodiments, R$^2$ is H.

In some embodiments, R$^3$ and R$^4$ are each independently selected from H, D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, OR$^{a3}$, SR$^{a3}$, C(=O)R$^{b3}$, C(=O)NR$^{c3}$R$^{d3}$, C(=O)OR$^{a3}$, OC(=O)R$^{b3}$, OC(=O)NR$^{c3}$R$^{d3}$, NR$^{c3}$R$^{d3}$, NR$^{c3}$C(=O)R$^{b3}$, NR$^{c3}$C(=O)OR$^{b3}$, NR$^{c3}$C(=O)NR$^{c3}$R$^{d3}$, C(=NR$^e$)R$^{b3}$, C(=NR$^e$)NR$^{c3}$R$^{d3}$, NR$^{c3}$C(=NR$^e$)NR$^{c3}$R$^{d3}$, NR$^{c3}$S(=O)$_2$R$^{b3}$, NR$^{c3}$S(=O)$_2$NR$^{c3}$R$^{d3}$, S(=O)$_2$R$^{b3}$, and S(=O)$_2$NR$^{c3}$R$^{d3}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{3A}$ substituents.

In some embodiments, R$^3$ and R$^4$ are each independently selected from H, D, halo, CN, NO$_2$, C$_{1-6}$ alkyl, C$_{2-6}$ alkenyl, C$_{2-6}$ alkynyl, C$_{1-6}$ haloalkyl, OR$^{a3}$, SR$^{a3}$, C(=O)R$^{b3}$, C(=O)NR$^{c3}$R$^{d3}$, C(=O)OR$^{a3}$, OC(=O)R$^{b3}$, OC(=O)NR$^{c3}$R$^{d3}$, NR$^{c3}$R$^{d3}$, NR$^{c3}$C(=O)R$^{b3}$, NR$^{c3}$C(=O)OR$^{b3}$, NR$^{c3}$C(=O)NR$^{c3}$R$^{d3}$, C(=NR$^e$)R$^{b3}$, C(=NR$^e$)NR$^{c3}$R$^{d3}$, NR$^{c3}$C(=NR$^e$)NR$^{c3}$R$^{d3}$, NR$^{c3}$S(=O)$_2$R$^{b3}$, NR$^{c3}$S(=O)$_2$NR$^{c3}$R$^{d3}$, S(=O)$_2$R$^{b3}$, and S(=O)$_2$NR$^{c3}$R$^{d3}$, wherein said C$_{1-6}$ alkyl, C$_{2-6}$ alkenyl, C$_{2-6}$ alkynyl, and C$_{1-6}$ haloalkyl are each optionally substituted with 1, 2, 3, or 4 independently selected R$^{3A}$ substituents.

In some embodiments, R$^3$ and R$^4$ are each independently selected from H, D, halo, CN, NO$_2$, C$_{1-6}$ alkyl, C$_{2-6}$ alkenyl, C$_{2-6}$ alkynyl, C$_{1-6}$ haloalkyl, OR$^{a3}$, C(=O)R$^{b3}$, C(=O)NR$^{c3}$R$^{d3}$, C(=O)OR$^{a3}$, NR$^{c3}$R$^{d3}$, NR$^{c3}$C(=O)R$^{b3}$, NR$^{c3}$S(=O)$_2$R$^{b3}$, S(=O)$_2$R$^{b3}$, and S(=O)$_2$NR$^{c3}$R$^{d3}$, wherein said C$_{1-6}$ alkyl, C$_{2-6}$ alkenyl, C$_{2-6}$ alkynyl, and C$_{1-6}$ haloalkyl are each optionally substituted with 1, 2, 3, or 4 independently selected R$^{3A}$ substituents.

In some embodiments, R$^3$ and R$^4$ are each independently selected from H, halo, CN, OH, C$_{1-6}$ alkyl, C$_{1-6}$ haloalkyl, C$_{1-6}$alkoxy, C$_{1-6}$haloalkoxy, amino, C$_{1-6}$alkylamino, di(C$_{1-6}$ alkyl)amino, carbamyl, C$_{1-6}$alkylcarbamyl, and di(C$_{1-6}$ alkyl)carbamyl.

In some embodiments, R$^3$ and R$^4$ are each independently selected from H, halo, CN, OH, C$_{1-6}$ alkyl, C$_{1-6}$ haloalkyl, C$_{1-6}$alkoxy, C$_{1-6}$haloalkoxy, amino, C$_{1-6}$alkylamino, di(C$_{1-6}$ alkyl)amino, carbamyl, C$_{1-6}$alkylcarbamyl, and di(C$_{1-6}$ alkyl)carbamyl.

In some embodiments, R$^3$ and R$^4$ are each independently selected from H, C$_{1-4}$ alkyl, and carbamyl.

In some embodiments, R$^3$ and R$^4$ are each independently selected from H and carbamyl.

In some embodiments, each R$^{a3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^{3A}$ substituents;

each R$^{b3}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{3A}$ substituents;

each $R^{3A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a31}$, $SR^{a31}$, $C(=O)R^{b31}$, $C(=O)NR^{c31}R^{d31}$, $C(=O)OR^{a31}$, $OC(=O)R^{b31}$, $OC(=O)NR^{c31}R^{d31}$, $NR^{c31}R^{d31}$, $NR^{c31}C(=O)R^{b31}$, $NR^{c31}C(=O)OR^{b31}$, $NR^{c31}C(=O)NR^{c31}R^{d31}$, $C(=NR^e)R^{b31}$, $C(=NR^e)NR^{c31}R^{d31}$, $NR^{c31}C(=NR^e)NR^{c31}R^{d31}$, $NR^{c31}S(=O)_2R^{b31}$, $NR^{c31}S(=O)_2NR^{c31}R^{d31}$, $S(=O)_2R^{b31}$, and $S(=O)_2NR^{c31}R^{d31}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{3B}$ substituents;

each $R^{a31}$, $R^{c31}$, and $R^{d31}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{3B}$ substituents;

each $R^{b31}$ is independently selected from $C_{1-6}$ alkyl and $C_{1-6}$ haloalkyl, each of which are optionally substituted with 1, 2, 3, or 4 independently selected $R^{3B}$ substituents; and each $R^{3B}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino.

In some embodiments, each $R^{a3}$, $R^{c3}$, and $R^{d3}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{3A}$ substituents;

each $R^{b3}$ is independently selected from $C_{1-6}$ alkyl and $C_{1-6}$ haloalkyl, each of which are optionally substituted with 1, 2, 3, or 4 independently selected $R^{3A}$ substituents; and each $R^{3A}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$ alkoxy, $C_{1-6}$ haloalkoxy, amino, $C_{1-6}$alkylamino, di($C_{1-6}$alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxy carbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino.

In some embodiments, each $R^{a3}$, $R^{c3}$, and $R^{d3}$ is independently selected from H, $C_{1-6}$ alkyl, and $C_{1-6}$ haloalkyl;
each $R^{b3}$ is independently selected from $C_{1-6}$ alkyl and $C_{1-6}$ haloalkyl; and each $R^{3A}$ is independently selected from H, halo, CN, OH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$haloalkoxy, amino, $C_{1-6}$alkylamino, and di($C_{1-6}$ alkyl)amino.

In some embodiments, each $R^{a3}$, $R^{c3}$, and $R^{d3}$ is independently selected from H, $C_{1-6}$ alkyl, and $C_{1-6}$ haloalkyl; and each $R^{b3}$ is independently selected from $C_{1-6}$ alkyl and $C_{1-6}$ haloalkyl.

In some embodiments, Ring C is a 5-6 membered heteroaryl ring or a 5-7 membered heterocycloalkyl ring, each of which is optionally substituted with 1, 2, 3, or 4 independently selected $R^C$ substituents.

In some embodiments, Ring C is a 5-membered heteroaryl ring or a 6-membered heterocycloalkyl ring, each of which is optionally substituted with 1, 2, 3, or 4 independently selected $R^C$ substituents.

In some embodiments, Ring C is a 5-7 membered heterocycloalkyl ring, which is optionally substituted with 1, 2, 3, or 4 independently selected $R^C$ substituents.

In some embodiments, Ring C is a 6-membered heterocycloalkyl ring, which is optionally substituted with 1, 2, 3, or 4 independently selected $R^C$ substituents.

In some embodiments, Ring C is a 5-membered heteroaryl ring, which is optionally substituted with 1 or 2 independently selected $R^C$ substituents.

In some embodiments, Ring C is a 5-membered heteroaryl ring or a 6-membered heterocycloalkyl ring, wherein the heteroaryl ring or heterocycloalkyl ring contains 1 or 2 oxygen ring members and wherein said 5-membered heteroaryl ring or 6-membered heterocycloalkyl ring are each optionally substituted with 1 or 2 independently selected $R^C$ substituents.

In some embodiments, Ring C is a moiety selected from:

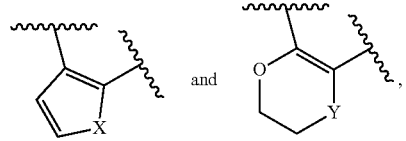

wherein:
X is S or O;
Y is $CH_2$, S or O; and
Ring C is optionally substituted with 1 or 2 independently selected $R^C$ substituents.

In some embodiments, Ring C is a moiety selected from:

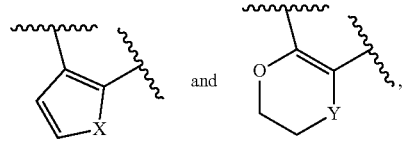

each which is optionally substituted with 1 or 2 independently selected $R^C$ substituents. In some embodiments, Ring C is

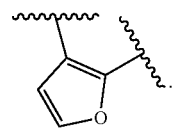 [SMILES: *c1ccoc1*]

In some embodiments, Ring C is

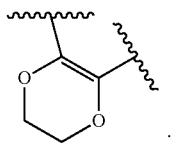 [SMILES: *C1=C(*)OCCO1]

In some embodiments, each $R^C$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aC}$, $SR^{aC}$, $C(=O)R^{bC}$, $C(=O)NR^{cC}R^{dC}$, $C(=O)OR^{aC}$, $OC(=O)R^{bC}$, $OC(=O)NR^{cC}R^{dC}$, $NR^{cC}R^{dC}$, $NR^{cC}C(=O)R^{bC}$, $NR^{cC}C(=O)OR^{bC}$, $NR^{cC}C(=O)NR^{cC}R^{dC}$, $C(=NR^e)R^{bC}$, $C(=NR^e)NR^{cC}R^{dC}$, $NR^{cC}C(=NR^e)NR^{cC}R^{dC}$, $NR^{cC}S(=O)_2R^{bC}$, $NR^{cC}S(=O)_2NR^{cC}R^{dC}$, $S(=O)_2R^{bC}$, and $S(=O)_2NR^{cC}R^{dC}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C1}$ substituents.

In some embodiments, each $R^C$ is independently selected from H, D, halo, CN, $C_{1-6}$ alkyl, $C_{2-6}$ alkenyl, $C_{2-6}$ alkynyl, $C_{1-6}$ haloalkyl, $OR^{aC}$, $SR^{aC}$, $C(=O)R^{bC}$, $C(=O)NR^{cC}R^{dC}$, $C(=O)OR^{aC}$, $OC(=O)R^{bC}$, $OC(=O)NR^{cC}R^{dC}$, $NR^{cC}R^{dC}$, $NR^{cC}C(=O)R^{bC}$, $NR^{cC}C(=O)OR^{bC}$, $NR^{cC}C(=O)NR^{cC}R^{dC}$, $C(=NR^e)R^{bC}$, $C(=NR^e)NR^{cC}R^{dC}$, $NR^{cC}C(=NR^e)NR^{cC}R^{dC}$, $NR^{cC}S(=O)_2R^{bC}$, $NR^{cC}S(=O)_2NR^{cC}R^{dC}$, $S(=O)_2R^{bC}$, and $S(=O)_2NR^{cC}R^{dC}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{C1}$ substituents.

In some embodiments, each $R^C$ is independently selected from H, D, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$haloalkoxy, amino, $C_{1-6}$alkylamino, di($C_{1-6}$ alkyl)amino, thio, $C_{1-6}$ alkylthio, $C_{1-6}$ alkylsulfonyl, carbamyl, $C_{1-6}$alkylcarbamyl, di($C_{1-6}$ alkyl)carbamyl, carboxy, $C_{1-6}$ alkylcarbonyl, $C_{1-6}$alkoxycarbonyl, $C_{1-6}$alkylcarbonyloxy, $C_{1-6}$alkylcarbonylamino, $C_{1-6}$ alkoxycarbonylamino, $C_{1-6}$ alkylaminocarbonyloxy. $C_{1-6}$alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$alkyl)aminosulfonylamino, aminocarbonylamino, $C_{1-6}$ alkylaminocarbonylamino, and di($C_{1-6}$alkyl)aminocarbonylamino.

In some embodiments, each $R^C$ is independently selected from H, halo, CN, OH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$haloalkoxy, amino, $C_{1-6}$ alkylamino, and di($C_{1-6}$alkyl)amino.

In some embodiments, each $R^C$ is independently selected from H and $C_{1-6}$ alkyl.

In some embodiments, each $R^{aC}$, $R^{cC}$, and $R^{dC}$ is independently selected from H, $C_{1-6}$ alkyl, $C_{1-6}$ haloalkyl, $C_{2-6}$ alkenyl, $C_{2-6}$ alkynyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C1}$ substituents; and each $R^{bC}$ is independently selected from $C_{1-6}$ alkyl, $C_{1-6}$ haloalkyl, $C_{2-6}$ alkenyl, $C_{2-6}$ alkynyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{C1}$ substituents;

each $R^{C1}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-6}$ cycloalkyl, $OR^{aC1}$, $SR^{aC1}$, $C(=O)R^{bC1}$, $C(=O)NR^{cC1}R^{dC1}$, $C(=O)OR^{aC1}$, $OC(=O)R^{bC1}$, $OC(=O)NR^{cC1}R^{dC1}$, $NR^{cC1}R^{dC1}$, $NR^{cC1}C(=O)R^{bC1}$, $NR^{cC1}C(=O)OR^{bC1}$, $NR^{cC1}C(=O)NR^{cC1}R^{dC1}$, $C(=NR^e)R^{bC1}$, $C(=NR^e)NR^{cC1}R^{dC1}$, $NR^{cC1}C(=NR^e)NR^{cC1}R^{dC1}$, $NR^{cC1}S(=O)_2R^{bC1}$, $NR^{cC1}S(=O)_2NR^{cC1}R^{dC1}$, $S(=O)_2R^{bC1}$, and $S(=O)_2NR^{cC1}R^{dC1}$, wherein said $C_{1-6}$ alkyl, $C_{2-6}$ alkenyl, $C_{2-6}$ alkynyl, $C_{1-6}$ haloalkyl, and $C_{3-6}$ cycloalkyl are each optionally substituted with 1, 2, 3, or 4 independently selected $R^{C2}$ substituents;

each $R^{aC1}$, $R^{cC1}$, and $R^{dC1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{C2}$ substituents;

each $R^{bC1}$ is independently selected from $C_{1-6}$ alkyl and $C_{1-6}$ haloalkyl, each of which are optionally substituted with 1, 2, 3, or 4 independently selected $R^{C2}$ substituents; and each $R^{C2}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino.

In some embodiments, each $R^{aC}$, $R^{cC}$, and $R^{dC}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{C1}$ substituents;

each $R^{bC}$ is independently selected from $C_{1-6}$ alkyl and $C_{1-6}$ haloalkyl, each of which are optionally substituted with 1, 2, 3, or 4 independently selected $R^{C1}$ substituents; and each $R^{C1}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino.

In some embodiments, each $R^{aC}$, $R^{cC}$, and $R^{dC}$ is independently selected from H, $C_{1-6}$ alkyl, and $C_{1-6}$ haloalkyl;

each $R^{bC}$ is independently selected from $C_{1-6}$ alkyl and $C_{1-6}$ haloalkyl; and each $R^{C1}$ is independently selected from H, halo, CN, OH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$haloalkoxy, amino, $C_{1-6}$alkylamino, and di($C_{1-6}$ alkyl)amino.

In some embodiments, each $R^{aC}$, $R^{cC}$, and $R^{dC}$ is independently selected from H, $C_{1-6}$ alkyl, and $C_{1-6}$ haloalkyl; and each $R^{bC}$ is independently selected from $C_{1-6}$ alkyl and $C_{1-6}$ haloalkyl.

In some embodiments, $R^5$, $R^6$, $R^7$, and $R^8$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^e)R^{b5}$, $C(=NR^e)NR^{c5}R^{d5}$, $NR^{c5}C(=NR^e)NR^{c5}R^{d5}$, $NR^{c5}S(=O)_2R^{b5}$, $NR^{c5}S(=O)_2NR^{c5}R^{d5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl are each optionally substituted with 1, 2, 3, or 4 independently selected $R^{5A}$ substituents.

In some embodiments, $R^5$, $R^6$, $R^7$, and $R^8$ are each independently selected from H, D, halo, CN, $NO_2$, Cue alkyl, $C_{2-6}$ alkenyl, $C_{2-6}$ alkynyl, $C_{1-6}$ haloalkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^e)R^{b5}$, $C(=NR^e)NR^{c5}R^{d5}$, $NR^{c5}C(=NR^e)NR^{c5}R^{d5}$, $NR^{c5}S(=O)_2R^{b5}$, $NR^{c5}S(=O)_2NR^{c5}R^{d5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{5A}$ substituents.

In some embodiments, $R^5$, $R^6$, $R^7$, and $R^8$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a5}$, $C(=O)R^{b5}$, $C(=O)NR^{c5}R^{d5}$, $C(=O)OR^{a5}$, $NR^{c5}R^{d5}$, $NR^{c5}C(=O)R^{b5}$, $NR^{c5}S(=O)_2R^{b5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{5A}$ substituents.

In some embodiments, $R^5$, $R^6$, $R^7$, and $R^8$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a5}$, $C(=O)R^{b5}$, $C(=O)NR^{c5}R^{d5}$, $C(=O)OR^{a5}$, $NR^{c5}R^{d5}$, $NR^{c5}C(=O)R^{b5}$, $NR^{c5}S(=O)_2R^{b5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{5A}$ substituents;

each $R^{a5}$, $R^{c5}$, and $R^{d5}$ is independently selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, $C_{2-6}$ alkynyl, and $C_{1-6}$ haloalkyl are each optionally substituted with 1 or 2 $R^{5A}$ substituents;

each $R^{b5}$ is independently selected from $C_{1-6}$ alkyl and $C_{1-6}$ haloalkyl; and each $R^{5A}$ is selected from $C(=O)NR^{c51}R^{d51}$, $C(=O)OR^{a51}$, $OC(=O)R^{b51}$, and $OC(=O)NR^{c51}R^{d51}$; and each $R^{a51}$, $R^{c51}$, and $R^{c51}$ is independently selected from H and $C_{1-6}$ alkyl, wherein each $C_{1-6}$ alkyl is optionally substituted with COOH.

In some embodiments, $R^5$, $R^6$, $R^7$, and $R^8$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a5}$, $C(=O)R^{b5}$, $C(=O)NR^{c5}R^{d5}$, $C(=O)OR^{a5}$, $NR^{c5}R^{d5}$, $NR^{c5}C(=O)R^{b5}$, $NR^{c5}S(=O)_2R^{b5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, and $C_{1-6}$ haloalkyl are each optionally substituted with 1 or 2 independently selected $R^{5A}$ substituents;

each $R^{a5}$, $R^{c5}$, and $R^{d5}$ is independently selected from H and $C_{1-6}$ alkyl, wherein the $C_{1-6}$ alkyl is optionally substituted with $OC(=O)NR^{c51}R^{d51}$;

each $R^{b5}$ is independently selected from $C_{1-6}$ alkyl and $C_{1-6}$ haloalkyl; and each $R^{c51}$ and $R^{c51}$ is independently selected from H and $C_{1-6}$ alkyl, wherein each $C_{1-6}$ alkyl is optionally substituted with COOH.

In some embodiments, $R^5$ is selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a5}$, $C(=O)R^{b5}$, $C(=O)NR^{c5}R^{d5}$, $C(=O)OR^{a5}$, $NR^{c5}R^{d5}$, $NR^{c5}C(=O)R^{b5}$, $NR^{c5}S(=O)_2R^{b5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{5A}$ substituents;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, $C_{2-6}$ alkynyl, and $C_{1-6}$ haloalkyl are each optionally substituted with 1 or 2 $R^{5A}$ substituents;

each $R^{5A}$ is selected from $C(=O)NR^{c51}R^{d51}$, $C(=O)OR^{a51}$, $OC(=O)R^{b51}$, and $OC(=O)NR^{c51}R^{d51}$;

each $R^{a51}$, $R^{c51}$, and $R^{c51}$ is independently selected from H and $C_{1-6}$ alkyl, wherein each $C_{1-6}$ alkyl is optionally substituted with COOH; and $R^6$, $R^7$, and $R^8$ are each independently selected H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino.

In some embodiments, $R^5$ is selected from H, D, $C_{1-6}$ alkyl, $C_{1-6}$ haloalkyl, and $OR^{a5}$;

$R^{a5}$ selected from H and $C_{1-6}$ alkyl, wherein the $C_{1-6}$ alkyl is optionally substituted with $OC(=O)NR^{c51}R^{d51}$; and each $R^{c51}$ and $R^{c51}$ is independently selected from H and $C_{1-6}$ alkyl, wherein each $C_{1-6}$ alkyl is optionally substituted with COOH.

In some embodiments $R^5$ is selected from H, $C_{1-4}$ alkyl, $O(C_{1-6}$ alkyl)-$OC(O)NH(C_{1-6}$ alkyl)COOH.

In some embodiments, $R^6$, $R^7$, and $R^8$ are each independently selected H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$haloalkoxy, amino, $C_{1-6}$alkylamino, di($C_{1-6}$alkyl)amino, thio, $C_{1-6}$ alkylthio, $C_{1-6}$ alkylsulfonyl, carbamyl, $C_{1-6}$alkylcarbamyl, di($C_{1-6}$alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$alkyl)aminosulfonylamino, aminocarbonylamino, $C_{1-6}$ alkylaminocarbonylamino, and di($C_{1-6}$alkyl)aminocarbonylamino.

In some embodiments, $R^5$, $R^6$, $R^7$, and $R^8$ are each independently selected from H, halo, CN, OH, $C_{1-6}$ alkyl, $C_{1-6}$ haloalkyl, $C_{1-6}$ alkoxy, $C_{1-6}$haloalkoxy, amino, $C_{1-6}$alkylamino, di($C_{1-6}$ alkyl)amino, carbamyl, $C_{1-6}$alkylcarbamyl, and di($C_{1-6}$ alkyl)carbamyl.

In some embodiments, $R^6$, $R^7$, and $R^8$ are each independently selected from H, halo, CN, OH, $C_{1-6}$ alkyl, $C_{1-6}$ haloalkyl, $C_{1-6}$ alkoxy, $C_{1-6}$haloalkoxy, amino, $C_{1-6}$alkylamino, di($C_{1-6}$ alkyl)amino, carbamyl, $C_{1-6}$alkylcarbamyl, and di($C_{1-6}$ alkyl)carbamyl.

In some embodiments:

$R^5$ is selected from H, $C_{1-4}$ alkyl, and $OR^{a5}$;

$R^{a5}$ is selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, $C_{2-6}$ alkynyl, and $C_{1-6}$ haloalkyl are each optionally substituted with 1 or 2 $R^{5A}$ substituents;

each $R^{5A}$ is selected from $C(=O)NR^{c51}R^{d51}$, $C(=O)OR^{a51}$, $OC(=O)R^{b51}$, and $OC(=O)NR^{c51}R^{d51}$;

each $R^{a51}$, $R^{c51}$, and $R^{c51}$ is independently selected from H and $C_{1-6}$ alkyl, wherein each (% 6 alkyl is optionally substituted with COOH.

In some embodiments $R^5$ is selected from H, $C_{1-4}$ alkyl, and —O($C_{1-6}$ alkyl)-OC(O)NH($C_{1-6}$ alkyl)COOH.

In some embodiments, $R^5$ is selected from H and $C_{1-4}$ alkyl.

In some embodiments $R^5$ is methyl or —OCH$_2$CH$_2$CH$_2$OC(O)NHCH$_2$CH$_2$COOH.

In some embodiments, $R^5$ is methyl.

In some embodiments, $R^5$ and $R^C$ are taken together to form linking group $L^2$.

In some embodiments, $R^6$ is H.

In some embodiments, $R^7$ and $R^8$ are each independently selected from H, carbamyl, and $C_{1-4}$ alkyl.

In some embodiments, $R^7$ and $R^8$ are each independently selected from H and carbamyl.

In some embodiments, each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{5-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{5A}$ substituents.

In some embodiments, each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5A}$ substituents;

each $R^{b5}$ is independently selected from $C_{1-6}$ alkyl, $C_{1-6}$ haloalkyl, $C_{2-6}$ alkenyl, $C_{2-6}$ alkynyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{5A}$ substituents;

each $R^{5A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a51}$, $SR^{a51}$, $C(=O)R^{b51}$, $C(=O)NR^{c51}R^{d51}$, $C(=O)OR^{a51}$, $OC(=O)R^{b51}$, $OC(=O)NR^{c51}R^{d51}$, $NR^{c51}R^{d51}$, $NR^{c51}C(=O)R^{b51}$, $NR^{c51}C(=O)OR^{b51}$, $NR^{c51}C(=O)NR^{c51}R^{d51}$, $C(=NR^e)R^{b51}$, $C(=NR^e)NR^{c51}R^{d51}$, $NR^{c51}C(=NR^e)NR^{c51}R^{d51}$, $NR^{c51}S(=O)_2R^{b51}$, $NR^{c51}S(=O)_2NR^{c51}R^{d51}$, $S(=O)_2R^{b51}$, and $S(=O)_2NR^{c51}R^{d51}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{5B}$ substituents;

each $R^{b51}$ is independently selected from $C_{1-6}$ alkyl and $C_{1-6}$ haloalkyl, each of which are optionally substituted with 1, 2, 3, or 4 independently selected $R^{5B}$ substituents; and each $R^{5B}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino.

In some embodiments, each $R^{a5}$, $R^{c5}$, and $R^{d5}$ is independently selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, $C_{2-6}$ alkynyl, and $C_{1-6}$ haloalkyl are each optionally substituted with 1 or 2 $R^{5A}$ substituents;

each $R^{b5}$ is selected from $C_{1-6}$ alkyl and $C_{1-6}$ haloalkyl;

each $R^{5A}$ is selected from $C(=O)NR^{c51}R^{d51}$, $C(=O)OR^{a51}$, $OC(=O)R^{b51}$, $OC(=O)NR^{c51}R^{d51}$; and each $R^{a51}$, $R^{c51}$, and $R^{c51}$ is independently selected from H and $C_{1-6}$ alkyl, wherein each $C_{1-6}$ alkyl is optionally substituted with COOH.

In some embodiments, each $R^{a5}$, $R^{c5}$, and $R^{d5}$ is independently selected from H and $C_{1-6}$ alkyl, wherein the $C_{1-6}$ alkyl is optionally substituted with $OC(=O)NR^{c51}R^{d51}$;

each $R^{c51}$ and $R^{c51}$ is independently selected from H and $C_{1-6}$ alkyl, wherein each $C_{1-6}$ alkyl is optionally substituted with COOH.

In some embodiments, $R^{a5}$ is selected from H and $C_{1-6}$ alkyl, wherein the $C_{1-6}$ alkyl is optionally substituted with $OC(=O)NR^{c51}R^{d51}$; and each $R^{c51}$ and $R^{c51}$ is independently selected from H and $C_{1-6}$ alkyl, wherein each $C_{1-6}$ alkyl is optionally substituted with COOH.

In some embodiments, each $R^{a5}$, $R^{c5}$, and $R^{d5}$ is independently selected from H, $C_{1-6}$ alkyl, and $C_{1-6}$ haloalkyl;

each $R^{b5}$ is independently selected from $C_{1-6}$ alkyl and $C_{1-6}$ haloalkyl; and each $R^{5A}$ is independently selected from H, halo, CN, OH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$haloalkoxy, amino, $C_{1-6}$alkylamino, and di($C_{1-6}$ alkyl)amino.

In some embodiments, each $R^{a5}$, $R^{c5}$, and $R^{d5}$ is independently selected from H, $C_{1-6}$ alkyl, and $C_{1-6}$ haloalkyl; and each $R^{b5}$ is independently selected from $C_{1-6}$ alkyl and $C_{1-6}$ haloalkyl.

In some embodiments, each Ring moiety A is selected from monocyclic $C_{3-7}$ cycloalkyl, phenyl, monocyclic 4-7 membered heterocycloalkyl, and monocyclic 5-6 membered heteroaryl, each of which is optionally substituted with 1, 2, 3, 4, or 5 independently selected $R^A$ substituents.

In some embodiments, each Ring moiety A is 5-6 membered heteroaryl, which is optionally substituted with 1, 2, 3, or 4 independently selected $R^A$ substituents.

In some embodiments, each Ring moiety A is 5-membered heteroaryl, which is optionally substituted with 1, 2, 3, or 4 independently selected $R^A$ substituents.

In some embodiments, each Ring moiety A is a pyrazole ring, which is optionally substituted with 1, 2, or 3 independently selected $R^A$ substituents.

In some embodiments, each $R^A$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aA}$, $SR^{aA}$, $C(=O)R^{bA}$, $C(=O)NR^{cA}R^{dA}$, $C(=O)OR^{aA}$, $OC(=O)R^{bA}$, $OC(=O)NR^{cA}R^{dA}$, $NR^{cA}R^{dA}$, $NR^{cA}C(=O)R^{bA}$, $NR^{cA}C(=O)OR^{bA}$, $NR^{cA}C(=O)NR^{cA}R^{dA}$, $NR^{cA}S(=O)_2R^{bA}$, $NR^{cA}S(=O)_2NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9A}$ substituents;

provided that when $R^A$ is attached to a nitrogen atom, then each $R^A$ is independently selected from H, CN, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $C(=O)R^{bA}$, $C(=O)NR^{cA}R^{dA}$, $C(=O)OR^{aA}$, $C(=NR^e)R^{bA}$, $C(=NR^e)NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9A}$ substituents.

In some embodiments, each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, $OR^{aA}$ $C(=O)R^{bA}$, $C(=O)NR^{cA}R^{dA}$, $C(=O)OR^{aA}$, $OC(=O)R^{bA}$, $OC(=O)NR^{cA}R^{dA}$, $NR^{cA}R^{dA}$, $NR^{cA}C(=O)R^{bA}$, $NR^{cA}C(=O)OR^{bA}$, $NR^{cA}C(=O)NR^{cA}R^{dA}$, $NR^{cA}S(=O)_2R^{bA}$, $NR^{cA}S(=O)_2NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9A}$ substituents;

provided that when $R^A$ is attached to a nitrogen atom, then each $R^A$ is independently selected from H, CN, $C_{1-6}$ alkyl, $C_{2-6}$ alkenyl, $C_{2-6}$ alkynyl, $C_{1-6}$ haloalkyl, $C(=O)R^{bA}$, $C(=O)NR^{cA}R^{dA}$, $C(=O)OR^{aA}$, $C(=NR^e)R^{bA}$, $C(=NR^e)NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9A}$ substituents.

In some embodiments, each $R^{aA}$, $R^{cA}$, and $R^{dA}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9A}$ substituents;

each $R^{bA}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9A}$ substituents; and each $R^{9A}$ is independently selected from H, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino.

In some embodiments, each $R^{aA}$, $R^{cA}$, and $R^{dA}$ is independently selected from H, $C_{1-6}$ alkyl, and $C_{1-6}$ haloalkyl; wherein said $C_{1-6}$ alkyl and $C_{1-6}$ haloalkyl are each optionally substituted with 1, 2, 3, or 4 independently selected $R^{9A}$ substituents;

each $R^{bA}$ is independently selected from $C_{1-6}$ alkyl and $C_{1-6}$ haloalkyl; wherein said $C_{1-6}$ alkyl and $C_{1-6}$ haloalkyl are each optionally substituted with 1, 2, 3, or 4 independently selected $R^{9A}$ substituents; and each $R^{9A}$ is independently selected from OH, CN, halo, $C_{1-6}$ alkyl, $C_{1-6}$ haloalkyl, $C_{1-6}$ alkoxy, $C_{1-6}$haloalkoxy, amino, $C_{1-6}$alkylamino, and di($C_{1-6}$ alkyl)amino.

In some embodiments, each $R^{aA}$, $R^{cA}$, and $R^{dA}$ is independently selected from H, $C_{1-6}$ alkyl, and $C_{1-6}$ haloalkyl; and each $R^{bA}$ is independently selected from $C_{1-6}$ alkyl and $C_{1-6}$ haloalkyl.

In some embodiments, each $R^A$ is independently selected from H, $C_{1-6}$ alkyl, $C_{2-6}$ alkenyl, $C_{2-6}$ alkynyl, CN, and $C_{1-6}$ haloalkyl.

In some embodiments, each $R^A$ is independently selected from H and $C_{1-6}$ alkyl.

In some embodiments, each $R^A$ is independently selected from H, methyl, and ethyl.

In some embodiments, Ring moiety B is selected from monocyclic $C_{3-7}$ cycloalkyl, phenyl, monocyclic 4-7 membered heterocycloalkyl, and monocyclic 5-6 membered heteroaryl, each of which is optionally substituted with 1, 2, 3, 4, or 5 independently selected $R^B$ substituents.

In some embodiments, Ring moiety B is a 5-6 membered heteroaryl ring, which is optionally substituted with 1, 2, 3, or 4 independently selected $R^B$ substituents.

In some embodiments, Ring moiety B is a 5-membered heteroaryl ring, which is optionally substituted with 1, 2, 3, or 4 independently selected $R^B$ substituents.

In some embodiments, Ring moiety B is a pyrazole ring, which is optionally substituted with 1, 2, or 3 independently selected $R^B$ substituents.

In some embodiments, each $R^B$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aB}$, $SR^{aB}$, $C(=O)R^{bB}$, $C(=O)NR^{cB}R^{dB}$, $C(=O)OR^{aB}$, $OC(=O)R^{bB}$, $OC(=O)NR^{cB}R^{dB}$, $NR^{cB}R^{dB}$, $NR^{cB}C(=O)R^{bB}$, $NR^{cB}C(=O)OR^{bB}$, $NR^{cB}C(=O)NR^{cB}R^{dB}$, $NR^{cB}S(=O)_2R^{bB}$, $NR^{cB}S(=O)_2NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

provided that when $R^B$ is attached to a nitrogen atom, then each $R^B$ is independently selected from H, CN, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $C(=O)R^{bB}$, $C(=O)NR^{cB}R^{dB}$, $C(=O)OR^{aB}$, $C(=NR^e)R^{bB}$, $C(=NR^e)NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents.

In some embodiments, each $R^B$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{aB}$, $C(=O)R^{bB}$, $C(=O)NR^{cB}R^{dB}$, $C(=O)OR^{aB}$, $OC(=O)R^{bB}$, $OC(=O)NR^{cB}R^{dB}$, $NR^{cB}R^{dB}$, $NR^{cB}C(=O)R^{bB}$, $NR^{cB}C(=O)OR^{bB}$, $NR^{cB}C(=O)NR^{cB}R^{dB}$, $NR^{cB}S(=O)_2R^{bB}$, $NR^{cB}S(=O)_2NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9B}$ substituents;

provided that when $R^B$ is attached to a nitrogen atom, then each $R^B$ is independently selected from H, CN, $C_{1-6}$ alkyl, $C_{2-6}$ alkenyl, $C_{2-6}$ alkynyl, $C_{1-6}$ haloalkyl, $C(=O)R^{bB}$, $C(=O)NR^{cB}R^{dB}$, $C(=O)OR^{aB}$, $C(=NR^e)R^{bB}$, $C(=NR^e)NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9B}$ substituents.

In some embodiments, each $R^{aB}$, $R^{cB}$, and $R^{dB}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{9B}$ substituents;

each $R^{bB}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{9B}$ substituents; and each $R^{9B}$ is independently selected from H, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino.

In some embodiments, each $R^{aB}$, $R^{cB}$, and $R^{dB}$ is independently selected from H, $C_{1-6}$ alkyl and $C_{1-6}$ haloalkyl; wherein said $C_{1-6}$ alkyl and $C_{1-6}$ haloalkyl are each optionally substituted with 1, 2, 3, or 4 independently selected $R^{9B}$ substituents;

each $R^{bB}$ is independently selected from $C_{1-6}$ alkyl and $C_{1-6}$ haloalkyl; wherein said $C_{1-6}$ alkyl and $C_{1-6}$ haloalkyl are each optionally substituted with 1, 2, 3, or 4 independently selected $R^{9B}$ substituents; and each $R^{9B}$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$alkylamino, and di($C_{1-6}$alkyl)amino.

In some embodiments, each $R^{aB}$, $R^{cB}$, and $R^{dB}$ is independently selected from H, $C_{1-6}$ alkyl, and $C_{1-6}$ haloalkyl; and each $R^{bB}$ is independently selected from $C_{1-6}$ alkyl and $C_{1-6}$ haloalkyl.

In some embodiments, each $R^B$ is independently selected from H, $C_{1-6}$ alkyl, $C_{2-6}$ alkenyl, $C_{2-6}$ alkynyl, CN, and $C_{1-6}$ haloalkyl.

In some embodiments, each $R^B$ is independently selected from H and $C_{1-6}$ alkyl.

In some embodiments, each $R^B$ is independently selected from H, methyl, and ethyl.

In some embodiments, $L^1$, $L^2$, and $L^3$ are each independently selected from —R—R—, —R—R—R—, -Cy-, —R-Cy-, -Cy-R—, and —R-Cy-R—.

In some embodiments, $L^1$, $L^2$, and $L^3$ are each independently selected from —R—R—, —R—R—R—, -Cy-, —R-Cy-, and -Cy-R—.

In some embodiments, $L^1$, $L^2$, and $L^3$ are each independently selected from —R—R— and —R—R—R—.

In some embodiments, $L^1$ is —R—R—R—.

In some embodiments, $L^1$ is —R—R—.

In some embodiments, $L^2$ is —R—R—R—.

In some embodiments, $L^2$ is —R—R—.

In some embodiments, $L^3$ is —R—R—R—.

In some embodiments, $L^3$ is —R—R—.

In some embodiments, each R is independently selected from M, $C_{1-6}$ alkylene, $C_{2-6}$ alkenylene, $C_{2-6}$ alkynylene, $C_{1-6}$ alkylene-M, and M-$C_{1-6}$ alkylene.

In some embodiments, each R is independently selected from M, $C_{1-6}$ alkylene, $C_{2-6}$ alkenylene, and $C_{2-6}$ alkynylene.

In some embodiments, each R is independently selected from M, $C_{1-3}$ alkylene, $C_{2-3}$ alkenylene, and $C_{2-3}$ alkynylene.

In some embodiments, each R is independently selected from $C_{1-6}$ alkylene and $C_{2-6}$ alkenylene.

In some embodiments, each R is independently selected from $C_{1-3}$ alkylene and $C_{2-3}$ alkenylene.

In some embodiments, each M is independently selected from —O—, —C(O)—, —C(O)NR$^L$—, —OC(O)NR$^L$—, —NR$^L$—, —NR$^L$C(O)—, —NR$^L$C(O)O—, —NR$^L$S(O)$_2$—, —S(O)$_2$—, and —S(O)$_2$NR$^L$—, provided that when M is attached to a nitrogen atom, then M is selected from —C(O)—, —C(O)NR$^L$—, —C(O)O—, —S(O)$_2$—, and —S(O)$_2$NR$^L$—; and each R$^L$ is independently selected from H and $C_{1-3}$ alkyl.

In some embodiments, each M is independently selected from —O—, —C(O)—, —C(O)NR$^L$—, —NR$^L$—, —NR$^L$C(O)—, —NR$^L$C(O)O—, —NR$^L$S(O)$_2$—, —S(O)$_2$—, and —S(O)$_2$NR$^L$—, provided that when M is attached to a nitrogen atom, then M is selected from —C(O)—, —C(O)NR$^L$—, —S(O)$_2$—, and —S(O)$_2$NR$^L$—; and each R$^L$ is independently selected from H and $C_{1-3}$ alkyl.

In some embodiments, $L^1$ is —CH$_2$—CH=CH—CH$_2$—.

In some embodiments, $L^2$ is —CH$_2$—CH=CH—CH$_2$—.

In some embodiments, $L^3$ is —CH$_2$—CH=CH—CH$_2$—.

In some embodiments, ---- is absent.

In some embodiments, ---- is present.

In some embodiments, ---- is present and $R^5$ and $R^6$ together with the carbon atoms to which they are attached, form Ring D, which is selected from a phenyl ring, 5-6 membered heteroaryl ring, and a 5-7 heterocycloalkyl ring, each of which is optionally substituted with 1, 2, 3, 4, or 5 independently selected $R^D$ substituents.

In some embodiments, Ring D is a 5-6 membered heteroaryl ring or a 5-7 membered heterocycloalkyl ring, each of which is optionally substituted with 1, 2, 3, or 4 independently selected $R^D$ substituents.

In some embodiments, Ring D is a 5-membered heteroaryl ring or a 6-membered heterocycloalkyl ring, each of which is optionally substituted with 1, 2, 3, or 4 independently selected $R^D$ substituents.

In some embodiments, Ring D is a moiety selected from

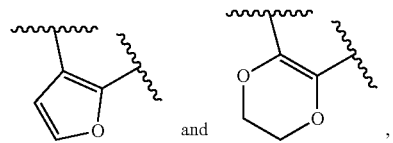 [SMILES: *c1ccoc1* ; *C1=C(*)OCCO1]

and each of which is optionally substituted with 1 or 2 independently selected $R^D$ substituents.

In some embodiments, each $R^D$ is independently selected from H, D, halo, CN, $C_{1-6}$ alkyl, $C_{2-6}$ alkenyl, $C_{2-6}$ alkynyl, $C_{1-6}$ haloalkyl, OR$^{aD}$, SRN C(=O)R$^{bD}$, C(=O)NR$^{cD}$R$^{dD}$, C(=O)OR$^{aD}$, OC(=O)R$^{bD}$, OC(=O)NR$^{cD}$R$^{dD}$, NR$^{cD}$R$^{dD}$, NR$^{cD}$C(=O)R$^{bD}$, NR$^{cD}$C(=O)OR$^{bD}$, NR$^{cD}$C(=O)NR$^{cD}$R$^{dD}$, C(=NR$^e$)R$^{bD}$, C(=NR$^e$)NR$^{cD}$R$^{dD}$, NR$^{cD}$C(=NR$^e$)NR$^{cD}$R$^{dD}$, NR$^{cD}$S(=O)$_2$R$^{bD}$, NR$^{cC}$S(=O)$_2$NR$^{cD}$R$^{dD}$, S(=O)$_2$R$^{bD}$, and S(=O)$_2$NR$^{cD}$R$^{dD}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^m$ substituents.

In some embodiments, each $R^D$ is independently selected from H, halo, CN, OH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$haloalkoxy, amino, $C_{1-6}$ alkylamino, and di($C_{1-6}$alkyl)amino.

In some embodiments, each $R^D$ is independently selected from H and $C_{1-6}$ alkyl.

In some embodiments:

each $R^{aD}$, $R^{cD}$, and $R^{dD}$ is independently selected from H, $C_{1-6}$ alkyl, $C_{1-6}$ haloalkyl, $C_{2-6}$ alkenyl, $C_{2-6}$ alkynyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^m$ substituents; and each $R^{bD}$ is independently selected from $C_{1-6}$ alkyl, $C_{1-6}$ haloalkyl, $C_{2-6}$ alkenyl, $C_{2-6}$ alkynyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, or 3 independently selected $R^{C1}$ substituents.

each $R^{D1}$ is independently selected from H, D, halo, CN, NO$_2$, $C_{1-6}$ alkyl, $C_{2-6}$ alkenyl, $C_{2-6}$ alkynyl, $C_{1-6}$ haloalkyl, $C_{3-6}$ cycloalkyl, OR$^{aD1}$, SR$^{aD1}$, C(=O)R$^{bD1}$, C(=O)

$NR^{cD1}R^{dD1}$, $C(=O)OR^{aD1}$, $OC(=O)R^{bD1}$, $OC(=O)NR^{cD1}R^{dD1}$, $NR^{cD1}R^{dD1}$, $NR^{cD1}C(=O)R^{bD1}$, $NR^{cD1}C(=O)OR^{bD1}$, $NR^{cD1}C(=O)NR^{cD1}R^{dD1}$, $C(=NR^e)R^{bD1}$, $C(=NR^e)NR^{cD1}R^{dD1}$, $NR^{cD1}C(=NR^e)NR^{cD1}R^{dD1}$, $NR^{cD1}S(=O)_2R^{bD1}$, $NR^{cD1}S(=O)_2NR^{cD1}R^{dD1}$, $S(=O)_2R^{bD1}$, and $S(=O)_2NR^{cD1}R^{dD1}$, wherein said $C_{1-6}$ alkyl, $C_{2-6}$ alkenyl, $C_{2-6}$ alkynyl, $C_{1-6}$ haloalkyl, and $C_{3-6}$ cycloalkyl are each optionally substituted with 1, 2, 3, or 4 independently selected $R^{D2}$ substituents;

each $R^{aD1}$, $R^{cD1}$, and $R^{dD1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{C2}$ substituents;

each $R^{bD}$ is independently selected from $C_{1-6}$ alkyl and $C_{1-6}$ haloalkyl, each of which are optionally substituted with 1, 2, 3, or 4 independently selected $R^{D2}$ substituents; and each $R^{D2}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$alkylcarbonyloxy, $C_{1-6}$alkylcarbonylamino, $C_{1-6}$ alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino.

In some embodiments:
each $R^{aD}$, $R^{cD}$, and $R^{dD}$ is independently selected from H, $C_{1-6}$ alkyl, and $C_{1-6}$ haloalkyl;
each $R^{bD}$ is independently selected from $C_{1-6}$ alkyl and $C_{1-6}$ haloalkyl; and
each $R^{D1}$ is independently selected from H, halo, CN, OH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$alkylamino, and di($C_{1-6}$ alkyl)amino.

In some embodiments:
each $R^{aD}$, $R^{cD}$, and $R^{dD}$ is independently selected from H, $C_{1-6}$ alkyl, and $C_{1-6}$ haloalkyl; and
each $R^{bD}$ is independently selected from $C_{1-6}$ alkyl and $C_{1-6}$ haloalkyl.

In some embodiments, n is 1; and m and s are each 0.
In some embodiments, m is 1; and n and s are each 0.
In some embodiments, s is 1; and n and m are each 0.
In some embodiments, n is 1; and m is 1.
In some embodiments, n is 1; and s is 1.
In some embodiments, m is 1; and s is 1.
In some embodiments:
n is 0 or 1;
m is 0 or 1;
s is 0 or 1;
wherein n+m+s=1 or 2;
when n is 1, then $R^1$ and $R^{1''}$ are each a bond;
when n is 0, then $R^1$ and $R^{1''}$ are each independently selected from H, $C_{1-6}$ alkyl, and $C_{1-6}$ haloalkyl; wherein said $C_{1-6}$ alkyl and $C_{1-6}$ haloalkyl are each optionally substituted with 1, 2, 3, or 4 independently selected $R^{1A}$ substituents;
each $R^{1A}$ is independently selected from H, halo, CN, OH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$haloalkoxy, amino, $C_{1-6}$alkylamino, and di($C_{1-6}$ alkyl)amino;
$R^2$ is H;
$R^{2''}$ is H;

$R^3$ and $R^4$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)OR^{b3}$, $NR^{c3}C(=O)NR^{c3}R^{d3}$, $C(=NR^e)R^{b3}$, $C(=NR^e)NR^{c3}R^{d3}$, $NR^{c3}C(=NR^e)NR^{c3}R^{d3}$, $NR^{c3}S(=O)_2R^{b3}$, $NR^{c3}S(=O)_2NR^{c3}R^{d3}$, $S(=O)_2R^{b3}$, and $S(=O)_2NR^{c3}R^{d3}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{3A}$ substituents;

each $R^{a3}$, $R^{c3}$, and $R^{d3}$ is independently selected from H, $C_{1-6}$ alkyl and $C_{1-6}$ haloalkyl, wherein said $C_{1-6}$ alkyl and $C_{1-6}$ haloalkyl are each optionally substituted with 1, 2, 3, or 4 independently selected $R^{3A}$ substituents;

each $R^{b3}$ is independently selected from H, $C_{1-6}$ alkyl and $C_{1-6}$ haloalkyl, each of which is optionally substituted with 1, 2, 3, or 4 independently selected $R^{3A}$ substituents;

each $R^e$ is independently selected from H, CN, OH, $C_{1-4}$ alkyl, and $C_{1-4}$alkoxy;

each $R^{3A}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

Ring C is a 5-membered heteroaryl ring or a 6-membered heterocycloalkyl ring, each of which is optionally substituted with 1, 2, 3, or 4 independently selected $R^C$ substituents;

each $R^C$ is independently selected from H, D, halo, CN, $C_{1-6}$ alkyl, $C_{2-6}$ alkenyl, $C_{2-6}$ alkynyl, $C_{1-6}$ haloalkyl, $OR^{aC}$, $SR^{aC}$, $C(=O)R^{bC}$, $C(=O)NR^{cC}R^{dC}$, $C(=O)OR^{aC}$, $OC(=O)R^{bC}$, $OC(=O)NR^{cC}R^{dC}$, $NR^{cC}R^{dC}$, $NR^{cC}C(=O)R^{bC}$, $NR^{cC}C(=O)OR^{bC}$, $NR^{cC}C(=O)NR^{cC}R^{dC}$, $C(=NR^e)R^{bC}$, $C(=NR^e)NR^{cC}R^{dC}$, $NR^{cC}C(=NR^e)NR^{cC}R^{dC}$, $NR^{cC}S(=O)_2R^{bC}$, $NR^{cC}S(=O)_2NR^{cC}R^{dC}$, $S(=O)_2R^{bC}$, and $S(=O)_2NR^{cC}R^{dC}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{C1}$ substituents;

each $R^{aC}$, $R^{cC}$, and $R^{dC}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{C1}$ substituents;

each $R^{bC}$ is independently selected from $C_{1-6}$ alkyl and $C_{1-6}$ haloalkyl, wherein said $C_{1-6}$ alkyl and $C_{1-6}$ haloalkyl are each optionally substituted with 1, 2, or 3 independently selected $R^{C1}$ substituents;

each $R^{C1}$ is independently selected from H, D, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

---- is absent;

$R^5$, $R^6$, $R^7$ and $R^8$ are each independently selected from $R^5$ and $R^6$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^e)R^{b5}$, $C(=NR^e)NR^{c5}R^{d5}$, $NR^{c5}C(=NR^e)NR^{c5}R^{d5}$, $NR^{c5}S(=O)_2R^{b5}$, $NR^{c5}S(=O)_2NR^{c5}R^{d5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{5A}$ substituents;

or when s is 1, then $R^5$ and one of $R^C$ taken together form a linking group $L^3$;

each $R^{a5}$, $R^{c5}$, and $R^{d5}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{5A}$ substituents;

each $R^{b5}$ is independently selected from $C_{1-6}$ alkyl and $C_{1-6}$ haloalkyl, each of which is optionally substituted with 1, 2, 3, or 4 independently selected $R^{5A}$ substituents;

each $R^{5A}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

Ring moiety A is a 5-6 membered heteroaryl ring, which is optionally substituted with 1, 2, 3, 4, or 5 independently selected $R^A$ substituents;

Ring moiety B is a 5-6 membered heteroaryl ring, which is optionally substituted with 1, 2, 3, 4, or 5 independently selected $R^B$ substituents;

provided that when m is 1, then one of $R^A$ and one of $R^B$ taken together form a linking group $L^2$;

each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, $OR^{aA}$, $C(=O)R^{bA}$, $C(=O)NR^{cA}R^{dA}$, $C(=O)OR^{aA}$, $OC(=O)R^{bA}$, $OC(=O)NR^{cA}R^{dA}$, $NR^{cA}R^{dA}$, $NR^{cA}C(=O)R^{bA}$, $NR^{cA}C(=O)OR^{bA}$, $NR^{cA}C(=O)NR^{cA}R^{dA}$, $NR^{cA}S(=O)_2R^{bA}$, $NR^{cA}S(=O)_2NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9A}$ substituents;

provided that when $R^A$ is attached to a nitrogen atom, then each $R^A$ is independently selected from H, CN, $C_{1-6}$ alkyl, $C_{2-6}$ alkenyl, $C_{2-6}$ alkynyl, $C_{1-6}$ haloalkyl, $C(=O)R^{bA}$, $C(=O)NR^{cA}R^{dA}$, $C(=O)OR^{aA}$, $C(=NR^e)R^{bA}$, $C(=NR^e)NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9A}$ substituents;

each $R^{aA}$, $R^{cA}$, and $R^{dA}$ is independently selected from H, $C_{1-6}$ alkyl, and $C_{1-6}$ haloalkyl;

wherein said $C_{1-6}$ alkyl and $C_{1-6}$ haloalkyl are each optionally substituted with 1, 2, 3, or 4 independently selected $R^{9A}$ substituents;

each $R^{bA}$ is independently selected from $C_{1-6}$ alkyl and $C_{1-6}$ haloalkyl; wherein said $C_{1-6}$ alkyl and $C_{1-6}$ haloalkyl are each optionally substituted with 1, 2, 3, or 4 independently selected $R^{9A}$ substituents;

each $R^{9A}$ is independently selected from OH, CN, halo, $C_{1-6}$ alkyl, $C_{1-6}$ haloalkyl, $C_{1-6}$ alkoxy, $C_{1-6}$haloalkoxy, amino, $C_{1-6}$alkylamino, and di($C_{1-6}$alkyl)amino;

each $R^B$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{aB}$, $C(=O)R^{bB}$, $C(=O)NR^{cB}R^{dB}$, $C(=O)OR^{aB}$, $OC(=O)R^{bB}$, $OC(=O)NR^{cB}R^{dB}$, $NR^{cB}R^{dB}$, $NR^{cB}C(=O)R^{bB}$, $NR^{cB}C(=O)OR^{bB}$, $NR^{cB}C(=O)NR^{cB}R^{dB}$, $NR^{cB}S(=O)_2R^{bB}$, $NR^{cB}S(=O)_2NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9B}$ substituents;

provided that when $R^B$ is attached to a nitrogen atom, then each $R^B$ is independently selected from H, CN, $C_{1-6}$ alkyl, $C_{2-6}$ alkenyl, $C_{2-6}$ alkynyl, $C_{1-6}$ haloalkyl, $C(=O)R^{bB}$, $C(=O)NR^{cB}R^{dB}$, $C(=O)OR^{aB}$, $C(=NR^e)R^{bB}$, $C(=NR^e)NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9B}$ substituents;

each $R^{aB}$, $R^{cB}$, and $R^{dB}$ is independently selected from H, $C_{1-6}$ alkyl, and $C_{1-6}$ haloalkyl;

wherein said $C_{1-6}$ alkyl and $C_{1-6}$ haloalkyl are each optionally substituted with 1, 2, 3, or 4 independently selected $R^{9B}$ substituents;

each $R^{bB}$ is independently selected from $C_{1-6}$ alkyl and $C_{1-6}$ haloalkyl; wherein said $C_{1-6}$ alkyl and $C_{1-6}$ haloalkyl are each optionally substituted with 1, 2, 3, or 4 independently selected $R^{9B}$ substituents;

each $R^{9B}$ is independently selected from OH, CN, halo, $C_{1-6}$ alkyl, $C_{1-6}$ haloalkyl, $C_{1-6}$ alkoxy, $C_{1-6}$haloalkoxy, amino, $C_{1-6}$alkylamino, and di($C_{1-6}$alkyl)amino;

or when m is 1, then one of $R^A$ and one of $R^B$ taken together form a linking group $L^2$;

$L^1$, $L^2$, and $L^3$ are each independently selected from —R—R— and —R—R—R—;

R is independently M, $C_{1-6}$ alkylene, $C_{2-6}$ alkenylene, or $C_{2-6}$ alkynylene; and each M is independently —O—, —C(O)—, —C(O)$NR^L$—, —OC(O)$NR^L$—, —$NR^L$—, —$NR^L$C(O)—, —$NR^L$C(O)O—, —$NR^L$S(O)$_2$—, —S(O)$_2$—, or —S(O)$_2$$NR^L$—, provided that when M is attached to a nitrogen atom, then M is selected from —C(O)—, —C(O)$NR^L$—, —C(O)O—, —S(O)$_2$—, or —S(O)$_2$$NR^L$—; and each $R^L$ is independently selected from H and $C_{1-3}$ alkyl.

In one aspect of the preceding embodiment, the compound is a compound of Formula (HI), as defined infra, or a pharmaceutically acceptable salt thereof.

In some embodiments:

n is 0 or 1;

m is 0 or 1;

s is 0 or 1;

wherein n+m+s=1 or 2;

when n is 1, then $R^1$ and $R^{1'''}$ are each a bond;

when n is 0, then $R^1$ and $R^{1'''}$ are each independently selected from H, $C_{1-6}$ alkyl, and $C_{1-6}$ haloalkyl;

$R^2$ is H;

$R^{2''}$ is H;

$R^3$ and $R^4$ are each independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl) carbamyl, carboxy, $C_{1-6}$alkylcarbonyl, $C_{1-6}$ alkoxy carbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

Ring C is a 5-membered heteroaryl ring or a 6-membered heterocycloalkyl ring, wherein the heteroaryl ring or heterocycloalkyl ring contains 1 or 2 oxygen ring members, wherein said 5-membered heteroaryl ring or a 6-membered heterocycloalkyl ring are each optionally substituted with 1 or 2 independently selected $R^C$ substituents;

each $R^C$ is independently selected from H, D, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$alkylcarbonyloxy, $C_{1-6}$alkylcarbonylamino, $C_{1-6}$alkoxycarbonyla mino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

---- is absent;

$R^5$ is selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a5}$, $C(=O)R^{b5}$, $C(=O)NR^{c5}R^{d5}$, $C(=O)OR^{a5}$, $NR^{c5}R^{d5}$, $NR^{c5}C(=O)R^{b5}$, $NR^{c5}S(=O)_2R^{b5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{5A}$ substituents;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, $C_{2-6}$ alkynyl, and $C_{1-6}$ haloalkyl are each optionally substituted with 1 or 2 $R^{5A}$ substituents;

each $R^{5A}$ is selected from $C(=O)NR^{c51}R^{d51}$, $C(=O)OR^{a51}$, $OC(=O)R^{b51}$, and $OC(=O)NR^{c51}R^{d51}$;

each $R^{a51}$, $R^{c51}$, and $R^{c51}$ is independently selected from H and $C_{1-6}$ alkyl, wherein each $C_{1-6}$ alkyl is optionally substituted with COOH or when s is 1, then $R^5$ and one of $R^C$ taken together form a linking group $L^3$;

$R^6$, $R^7$, and $R^8$ are each independently selected H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl) carbamyl, carboxy, $C_{1-6}$alkylcarbonyl, $C_{1-6}$ alkoxy carbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

Ring moiety A is a 5-membered heteroaryl ring, which is optionally substituted with 1, 2, or 3 independently selected $R^A$ substituents;

Ring moiety B is a 5-membered heteroaryl ring, which is optionally substituted with 1, 2, or 3 independently selected $R^B$ substituents;

or when m is 1, then one of $R^A$ and one of $R^B$ taken together form a linking group $L^2$;

each $R^A$ is independently selected from H, $C_{1-6}$ alkyl, $C_{2-6}$ alkenyl, $C_{2-6}$ alkynyl, CN, and $C_{1-6}$ haloalkyl;

each $R^B$ is independently selected from H, $C_{1-6}$ alkyl, $C_{2-6}$ alkenyl, $C_{2-6}$ alkynyl, CN, and $C_{1-6}$ haloalkyl;

$L^1$, $L^2$, and $L^3$ are each independently selected from —R—R— and —R—R—R—; and R is independently $C_{1-6}$ alkylene, $C_{2-6}$ alkenylene, or $C_{2-6}$ alkynylene.

In one aspect of the preceding embodiment, the compound is a compound of Formula (III), as defined infra, or a pharmaceutically acceptable salt thereof.

In some embodiments:

n is 0 or 1;

m is 0 or 1;

s is 0 or 1;

wherein n+m+s=1 or 2;

when n is 1, then $R^1$ and $R^{1'''}$ are each a bond;

when n is 0, then $R^1$ and $R^{1'''}$ are each independently selected from H, $C_{1-6}$ alkyl, and $C_{1-6}$ haloalkyl;

$R^2$ is H;

$R^{2''}$ is H;

$R^3$ and $R^4$ are each independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl) carbamyl, carboxy, $C_{1-6}$alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

Ring C is a 5-membered heteroaryl ring or a 6-membered heterocycloalkyl ring, wherein the heteroaryl ring or heterocycloalkyl ring contains 1 or 2 oxygen ring members, wherein said 5-membered heteroaryl ring or a 6-membered heterocycloalkyl ring are each optionally substituted with 1 or 2 independently selected $R^C$ substituents;

each $R^C$ is independently selected from H, D, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$alkoxy, $C_{1-6}$ haloalkoxy, amino, $C_{1-6}$alkylamino, di($C_{1-6}$alkyl)amino, thio, $C_{1-6}$alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

---- is absent;

$R^5$, $R^6$, $R^7$, and $R^8$ are each independently selected H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxy carbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

or when s is 1, then $R^5$ and one of $R^C$ taken together form a linking group $L^3$;

Ring moiety A is a 5-membered heteroaryl ring, which is optionally substituted with 1, 2, or 3 independently selected $R^A$ substituents;

Ring moiety B is a 5-membered heteroaryl ring, which is optionally substituted with 1, 2, or 3 independently selected $R^B$ substituents;

or when m is 1, then one of $R^A$ and one of $R^B$ taken together form a linking group $L^2$;

each $R^A$ is independently selected from H, $C_{1-6}$ alkyl, $C_{2-6}$ alkenyl, $C_{2-6}$ alkynyl, CN, and $C_{1-6}$ haloalkyl;

each $R^B$ is independently selected from H, $C_{1-6}$ alkyl, $C_{2-6}$ alkenyl, $C_{2-6}$ alkynyl, CN, and $C_{1-6}$ haloalkyl;

$L^1$, $L^2$, and $L^3$ are each independently selected from —R—R— and —R—R—R—; and R is independently $C_{1-6}$ alkylene, $C_{2-6}$ alkenylene, or $C_{2-6}$ alkynylene.

In one aspect of the preceding embodiment, the compound is a compound of Formula (HI), as defined infra, or a pharmaceutically acceptable salt thereof.

In some embodiments:
n is 0 or 1;
m is 0 or 1;
s is 0 or 1;
wherein n+m+s=1 or 2;
when n is 1, then $R^1$ and $R^{1'''}$ are each a bond;
when n is 0, then $R^1$ and $R^{1'''}$ are each independently selected from H, $C_{1-6}$ alkyl, and $C_{1-6}$ haloalkyl;
$R^2$ is H;
$R^{2''}$ is H;
$R^3$ and $R^4$ are each independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxy carbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

Ring C is a 5-membered heteroaryl ring or a 6-membered heterocycloalkyl ring, wherein the heteroaryl ring or heterocycloalkyl ring contains 1 or 2 oxygen ring members, wherein said 5-membered heteroaryl ring or a 6-membered heterocycloalkyl ring are each optionally substituted with 1 or 2 independently selected $R^C$ substituents;

each $R^C$ is independently selected from H, D, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$ alkoxy, $C_{1-6}$ haloalkoxy, amino, $C_{1-6}$alkylamino, di($C_{1-6}$alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonyl amino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

---- is absent;

$R^5$ is selected from H, D, $C_{1-6}$ alkyl, $C_{1-6}$ haloalkyl, and $OR^{a5}$;

$R^{a5}$ selected from H and $C_{1-6}$ alkyl, wherein the $C_{1-6}$ alkyl is optionally substituted with $OC(=O)NR^{c51}R^{d51}$;

each $R^{c51}$ and $R^{c51}$ is independently selected from H and $C_{1-6}$ alkyl, wherein each $C_{1-6}$ alkyl is optionally substituted with COOH;

$R^6$, $R^7$, and $R^8$ are each independently selected H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl) carbamyl, carboxy, $C_{1-6}$alkylcarbonyl, $C_{1-6}$ alkoxy carbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

or when s is 1, then $R^5$ and one of $R^C$ taken together form a linking group $L^3$;

Ring moiety A is a pyrazole ring, which is optionally substituted with 1, 2, or 3 independently selected $R^A$ substituents;

Ring moiety B is a pyrazole ring, which is optionally substituted with 1, 2, or 3 independently selected $R^B$ substituents;

provided that when m is 1, then one of $R^A$ and one of $R^B$ taken together form a linking group $L^2$;

each $R^A$ is independently selected from H, $C_{1-6}$ alkyl, $C_{2-6}$ alkenyl, $C_{2-6}$ alkynyl, CN, and $C_{1-6}$ haloalkyl;

each $R^B$ is independently selected from H, $C_{1-6}$ alkyl, $C_{2-6}$ alkenyl, $C_{2-6}$ alkynyl, CN, and $C_{1-6}$ haloalkyl;

$L^1$, $L^2$, and $L^3$ are each independently selected from —R—R— and —R—R—R—; and R is independently $C_{1-6}$ alkylene, $C_{2-6}$ alkenylene, or $C_{2-6}$ alkynylene.

In one aspect of the preceding embodiment, the compound is a compound of Formula (HI), as defined infra, or a pharmaceutically acceptable salt thereof.

In some embodiments:
n is 0 or 1;
m is 0 or 1;
s is 0 or 1;
wherein n+m+s=1 or 2;
when n is 1, then $R^1$ and $R^{1'''}$ are each a bond;
when n is 0, then $R^1$ and $R^{1'''}$ are each independently selected from H, $C_{1-6}$ alkyl, and $C_{1-6}$ haloalkyl;
$R^2$ is H;
$R^{2''}$ is H;
$R^3$ and $R^4$ are each independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxy carbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

Ring C is a 5-membered heteroaryl ring or a 6-membered heterocycloalkyl ring, wherein the heteroaryl ring or heterocycloalkyl ring contains 1 or 2 oxygen ring members, wherein said 5-membered heteroaryl ring or a 6-membered heterocycloalkyl ring are each optionally substituted with 1 or 2 independently selected $R^C$ substituents;

each $R^C$ is independently selected from H, D, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$alkoxy-$C_{1-6}$ alkyl, $C_{1-6}$ alkoxy, $C_{1-6}$ haloalkoxy, amino, $C_{1-6}$alkylamino, di($C_{1-6}$alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

---- is absent;

$R^5$, $R^6$, $R^7$, and $R^8$ are each independently selected H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$haloalkoxy, amino, $C_{1-6}$alkylamino, di($C_{1-6}$ alkyl)amino, thio, $C_{1-6}$alkylthio, $C_{1-6}$ alkylsulfonyl, carbamyl, $C_{1-6}$alkylcarbamyl, di($C_{1-6}$ alkyl)carbamyl, carboxy, $C_{1-6}$alkylcarbonyl, $C_{1-6}$ alkoxy carbonyl, $C_{1-6}$alkylcarbonyloxy, $C_{1-6}$alkylcarbonylamino, $C_{1-6}$alkoxycarbonylamino, $C_{1-6}$ alkylaminocarbonyloxy, $C_{1-6}$alkylsulfonylamino, aminosulfonyl, $C_{1-6}$alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$alkylaminocarbonylamino, and di($C_{1-6}$ alkyl)aminocarbonylamino;

or when s is 1, then $R^5$ and one of $R^C$ taken together form a linking group $L^3$;

Ring moiety A is a pyrazole ring, which is optionally substituted with 1, 2, or 3 independently selected $R^A$ substituents;

Ring moiety B is a pyrazole ring, which is optionally substituted with 1, 2, or 3 independently selected $R^B$ substituents;

provided that when m is 1, then one of $R^A$ and one of $R^B$ taken together form a linking group $L^2$;

each $R^A$ is independently selected from H, $C_{1-6}$ alkyl, $C_{2-6}$ alkenyl, $C_{2-6}$ alkynyl, CN, and $C_{1-6}$ haloalkyl;

each $R^B$ is independently selected from H, $C_{1-6}$ alkyl, $C_{2-6}$ alkenyl, $C_{2-6}$ alkynyl, CN, and $C_{1-6}$ haloalkyl;

$L^1$, $L^2$, and $L^3$ are each independently selected from —R—R— and —R—R—R—; and R is independently $C_{1-6}$ alkylene, $C_{2-6}$ alkenylene, or $C_{2-6}$ alkynylene.

In one aspect of the preceding embodiment, the compound is a compound of Formula (HI), as defined infra, or a pharmaceutically acceptable salt thereof.

In some embodiments:
n is 1;
m is 0;
s is 0;
$R^1$ and $R^{1''}$ are each a bond;
$R^2$ is H;
$R^{2''}$ is H;
$R^3$ and $R^4$ are each independently selected from H, halo, CN, OH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$ haloalkoxy, amino, $C_{1-6}$alkylamino, di($C_{1-6}$ alkyl)amino, carbamyl, $C_{1-6}$alkylcarbamyl, and di($C_{1-6}$ alkyl)carbamyl;

Ring C is a moiety selected from:

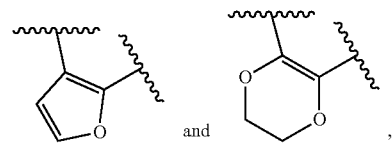 [SMILES: *c1ccoc1* ; *C1=C(*)OCCO1]

each of which are optionally substituted with 1 or 2 independently selected $R^C$ substituents;

each $R^C$ is independently selected from H and $C_{1-6}$ alkyl;

---- is absent;

$R^5$, $R^6$, $R^7$, and $R^8$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a5}$, $C(=O)R^{b5}$, $C(=O)NR^{c5}R^{d5}$, $C(=O)OR^{a5}$, $NR^{c5}R^{d5}$, $NR^{c5}C(=O)R^{b5}$, $NR^{c5}S(=O)_2R^{b5}$, $S(=O)_2 R^{b5}$, and $S(=O)_2NR^{c5}R^{d5}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{5A}$ substituents;

each $R^{a5}$, $R^{b5}$, $R^{c5}$, and $R^{d5}$ is independently selected from H, $C_{1-6}$ alkyl, $C_{2-6}$ alkenyl, $C_{2-6}$ alkynyl, and $C_{1-6}$ haloalkyl, wherein the $C_{1-6}$ alkyl, $C_{2-6}$ alkenyl, $C_{2-6}$ alkynyl, and $C_{1-6}$ haloalkyl are each optionally substituted with 1 or 2 $R^{5A}$ substituents;

each $R^{5A}$ is selected from $C(=O)NR^{c51}R^{d51}$, $C(=O)OR^{a51}$, $OC(=O)R^{b51}$, and $OC(=O)NR^{c51}R^{d51}$;

each $R^{a51}$, $R^{c51}$, and $R^{c51}$ is independently selected from H and $C_{1-6}$ alkyl, wherein each $C_{1-6}$ alkyl is optionally substituted with COOH;

Ring moiety A is a pyrazole ring, which is optionally substituted with 1, 2, or 3 independently selected $R^A$ substituents;

Ring moiety B is a pyrazole ring, which is optionally substituted with 1, 2, or 3 independently selected $R^B$ substituents;

each $R^A$ is independently selected from H and $C_{1-6}$ alkyl;
each $R^B$ is independently selected from H and $C_{1-6}$ alkyl;
$L^1$ is selected from —R—R— and —R—R—R—; and
R is independently $C_{1-3}$ alkylene, $C_{2-3}$ alkenylene, or $C_{2-3}$ alkynylene.

In one aspect of the preceding embodiment, the compound is a compound of Formula (HI), as defined infra, or a pharmaceutically acceptable salt thereof.

In some embodiments:
n is 1;
m is 0;
s is 0;
$R^1$ and $R^{1''}$ are each a bond;
$R^2$ is H;
$R^{2''}$ is H;

$R^3$ and $R^4$ are each independently selected from H, halo, CN, OH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$ haloalkoxy, amino, $C_{1-6}$alkylamino, di($C_{1-6}$ alkyl)amino, carbamyl, $C_{1-6}$alkylcarbamyl, and di($C_{1-6}$ alkyl)carbamyl;

Ring C is a moiety selected from:

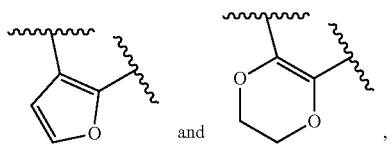 [SMILES: *c1ccoc1* ; *C1=C(*)OCCO1]

and each of which are optionally substituted with 1 or 2 independently selected $R^C$ substituents;

each $R^C$ is independently selected from H and $C_{1-6}$ alkyl;

---- is absent;

$R^5$, $R^6$, $R^7$ and $R^8$ are each independently selected H, halo, CN, OH, $C_{1-6}$ alkyl, $C_{2-6}$ alkenyl, $C_{2-6}$ alkynyl, $C_{1-6}$ haloalkyl, $C_{1-6}$alkoxy, $C_{1-6}$ haloalkoxy, amino, $C_{1-6}$alkylamino, di($C_{1-6}$ alkyl)amino, carbamyl, $C_{1-6}$alkylcarbamyl, and di($C_{1-6}$ alkyl)carbamyl;

Ring moiety A is a pyrazole ring, which is optionally substituted with 1, 2, or 3 independently selected $R^A$ substituents;

Ring moiety B is a pyrazole ring, which is optionally substituted with 1, 2, or 3 independently selected $R^B$ substituents;

each $R^A$ is independently selected from H and $C_{1-6}$ alkyl;

each $R^B$ is independently selected from H and $C_{1-6}$ alkyl;

$L^1$ is selected from —R—R— and —R—R—R—; and

R is independently $C_{1-3}$ alkylene, $C_{2-3}$ alkenylene, or $C_{2-3}$ alkynylene.

In one aspect of the preceding embodiment, the compound is a compound of Formula (III), as defined infra, or a pharmaceutically acceptable salt thereof.

In some embodiments, the compound is a compound of Formula (II):

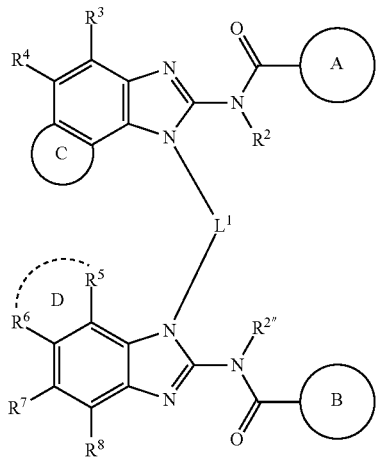

(II)

or a pharmaceutically acceptable salt thereof.

In some embodiments, the compound is a compound of Formula (III):

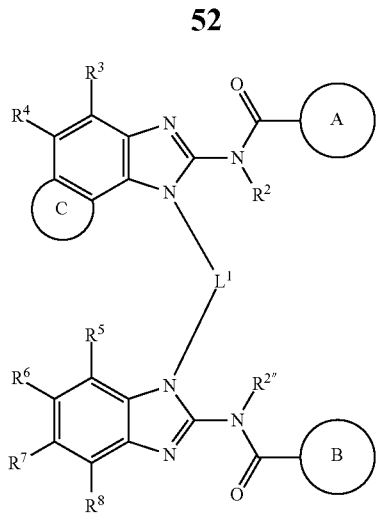

(III)

or a pharmaceutically acceptable salt thereof.

In some embodiments, the compound is a compound of Formula (IV):

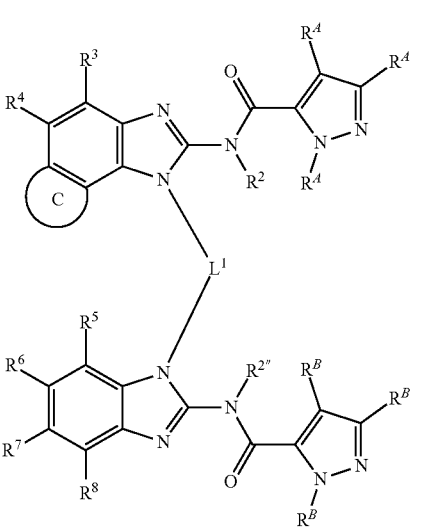

(IV)

or a pharmaceutically acceptable salt thereof.

In some embodiments, the compound is a compound of Formula (V):

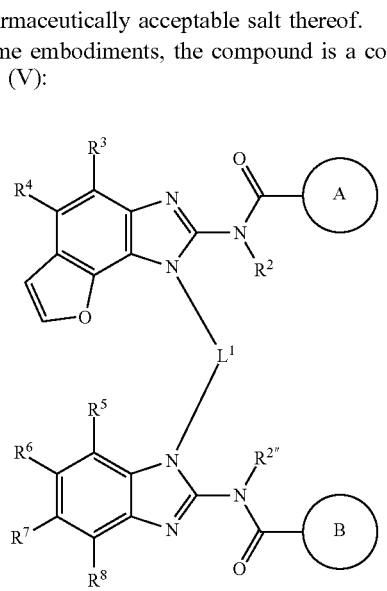

(V)

or a pharmaceutically acceptable salt thereof.

In some embodiments, the compound is a compound of Formula (VI):

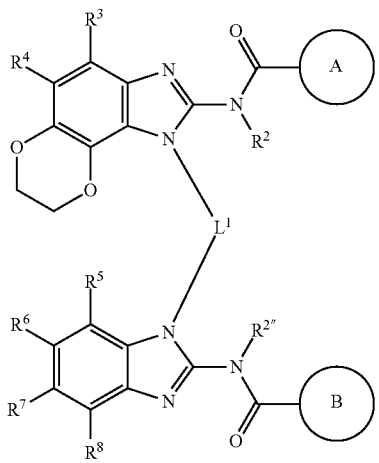

(VI)

or a pharmaceutically acceptable salt thereof.

In some embodiments, the compound is a compound of Formula (VII):

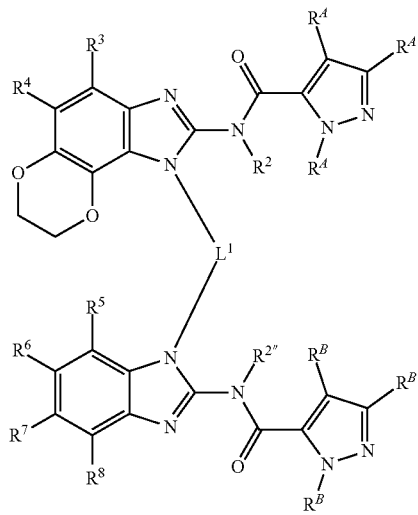

(VII)

or a pharmaceutically acceptable salt thereof.

In some embodiments, the compound is a compound of Formula (VIII):

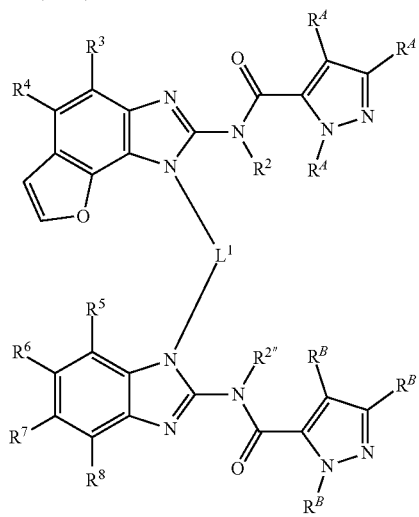

(VIII)

or a pharmaceutically acceptable salt thereof.

In some embodiments, the compound is a compound of Formula (IX):

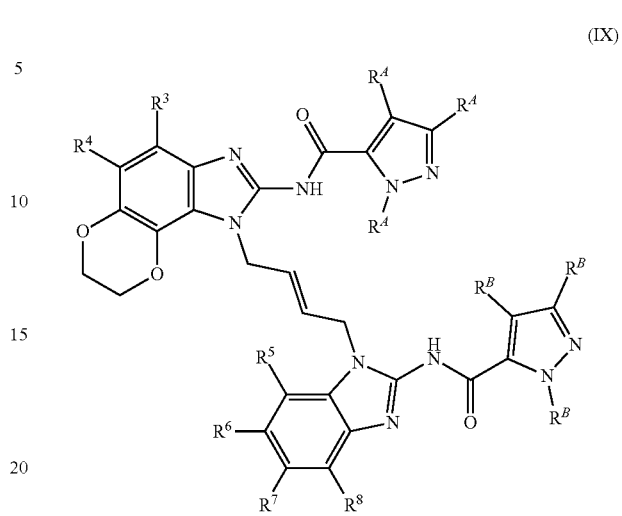

(IX)

or a pharmaceutically acceptable salt thereof.

In some embodiments, the compound is a compound of Formula (X):

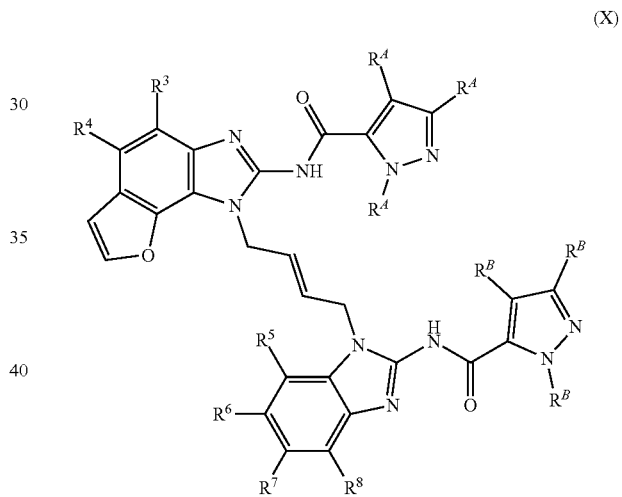

(X)

or a pharmaceutically acceptable salt thereof.

Formulas (II), (III), (IV), (V), (VI), (VII), (VIII), (IX), and (X) can be combined with any of the aforementioned embodiments.

In some embodiments, 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-4}$ alkyl-", "alkylene", "alkenylene" and "alkynylene" linking groups, as described herein, are optionally replaced by deuterium atoms.

It is further appreciated that certain features of the invention, which are, for clarity, described in the context of separate embodiments, can also be provided in combination in a single embodiment (i.e., as if the embodiments are multiply dependent claims). Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency, that the designated atom's normal valency is not exceeded, and that the substitution results in a stable compound.

As used herein, the phrase "each 'variable' is independently selected from" means substantially the same as wherein "at each occurrence 'variable' is selected from."

When any variable (e.g., $R^S$) occurs more than one time in any constituent or formula for a compound, its definition at each occurrence is independent of its definition at every other occurrence. Thus, for example, if a group is shown to be substituted with 1, 2, 3, or 4 $R^S$, then said group may optionally be substituted with up to four $R^S$ groups and $R^S$ at each occurrence is selected independently from the definition of $R^S$. Also, combinations of substituents and/or variables are permissible only if such combinations result in stable compounds; for example the combination of a first M group and second M group in the combination of two R groups are permissible only if such combinations of M-M result in stable compounds (e.g., M-M is not permissible if it will form highly reactive compounds such as peroxides having 0-0 bonds).

Throughout the definitions, the term "C$_n$-m" indicates a range which includes the endpoints, wherein n and m are integers and indicate the number of carbons. Examples include C$_{1-3}$, C$_{1-4}$, C$_{1-6}$, and the like.

As used herein, the term "C$_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, ten-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "C$_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms. As used herein, "C$_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms. As used herein, the term "C$_{n-m}$ alkoxy", employed alone or in combination with other terms, refers to a group of formula-O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2 fused rings). The term "C$_{n-m}$aryl" refers to an aryl group having from n to m ring carbon atoms.

Aryl groups include, e.g., phenyl, naphthyl, anthracenyl, phenanthrenyl, indanyl, indenyl, and the like. In some embodiments, the aryl group has from 6 to 10 carbon atoms. In some embodiments, the aryl group is phenyl or naphthyl. In some embodiments, the aryl is phenyl.

As used herein, "halo" refers to F, Cl, Br, or I. In some embodiments, halo is F, Cl, or Br.

In some embodiments, halo is F or Cl. In some embodiments, halo is F. In some embodiments, halo is Cl.

As used herein, "C$_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "C$_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include CF$_5$, C$_2$F$_5$, CHF$_2$, CH$_2$F, CCl$_5$, CHCl$_2$, C$_2$Cl$_5$ and the like.

As used herein, the term "thio" refers to a group of formula —SH.

As used herein, the term "C$_{n-m}$alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "C$_{n-m}$alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "C$_{n-m}$alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$ alkoxycarbonylamino" refers to a group of formula —NHC(O)O(C$_{n-m}$ alkyl), wherein the alkyl group has n to m carbon atoms. In some embodiments, the alkyl group has 1 to 6, 1 to 4, or 1 to 3 carbon atoms.

As used herein, the term "C$_{n-m}$alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "$C_{n-m}$alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "cyano-$C_{1-6}$ alkyl" refers to a group of formula —($C_{1-6}$alkylene)-CN. As used herein, the term "cyano-$C_{1-3}$ alkyl" refers to a group of formula —($C_{1-3}$ alkylene)-CN.

As used herein, the term "HO—$C_{1-6}$ alkyl" refers to a group of formula —($C_{1-6}$ alkylene)-OH. As used herein, the term "HO—$C_{1-3}$ alkyl" refers to a group of formula —($C_{1-3}$ alkylene)-OH.

As used herein, the term "$C_{1-6}$alkoxy-$C_{1-6}$ alkyl" refers to a group of formula —($C_{1-3}$ alkylene)-O($C_{1-6}$ alkyl). As used herein, the term "$C_{1-3}$ alkoxy-$C_{1-3}$ alkyl" refers to a group of formula —($C_{1-3}$ alkylene)-O($C_{1-3}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkylcarbonyloxy" is a group of formula —OC(O)-alkyl, wherein the alkyl group has n to m carbon atoms. In some embodiments, the alkyl group has 1 to 6, 1 to 4, or 1 to 3 carbon atoms.

As used herein, "aminocarbonyloxy" is a group of formula —OC(O)—NH$_2$.

As used herein, "$C_{n-m}$ alkylaminocarbonyloxy" is a group of formula —OC(O)—NH-alkyl, wherein the alkyl group has n to m carbon atoms. In some embodiments, the alkyl group has 1 to 6, 1 to 4, or 1 to 3 carbon atoms.

As used herein, "di($C_{n-m}$alkyl)aminocarbonyloxy" is a group of formula —OC(O)—N(alkyl)$_2$, wherein each alkyl group has, independently, n to m carbon atoms. In some embodiments, each alkyl group independently has 1 to 6, 1 to 4, or 1 to 3 carbon atoms.

As used herein $C_{n-m}$ alkoxycarbonylamino refers to a group of formula —NHC(O)—O-alkyl, wherein the alkyl group has n to m carbon atoms.

As used herein, the term "carbamyl" to a group of formula —C(O)NH$_2$.

As used herein, the term "carbonyl", employed alone or in combination with other terms, refers to a —C(O)— group.

As used herein, "cycloalkyl" refers to non-aromatic cyclic hydrocarbons including cyclized alkyl and alkenyl groups. Cycloalkyl groups can include mono- or polycyclic (e.g., having 2, 3 or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, 12, 13 or 14 ring-forming carbons (i.e., $C_{3-14}$). In some embodiments, the cycloalkyl is a $C_{3-12}$ monocyclic or bicyclic cycloalkyl which is optionally substituted by CH$_2$F, CHF$_2$, CF$_3$, and CF$_2$CF$_3$. In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-14}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2, 3, or 4 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S and B. In some embodiments, the heteroaryl is a 5-6 monocyclic heteroaryl having 1 or 2 heteroatom ring members independently selected from N, O, and S. In some embodiments, the heteroaryl group contains 3 to 14, 3 to 10, 4 to 14, 4 to 10, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, thieno[3,2-b]pyridine, imidazo[1,2-o]pyridine, 1,5-naphthyridine, 1H-pyrazolo[4,3-b]pyridine, and the like.

A five-membered heteroaryl is a heteroaryl group having five ring-forming atoms wherein one or more (e.g., 1, 2, or 3) of the ring-forming atoms are independently selected from N, O, S or B. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine.

A six-membered heteroaryl ring is a heteroaryl group having six ring-forming atoms wherein one or more (e.g., 1, 2, or 3) of the ring-forming atoms are independently selected from N, O, S and B. Exemplary six-membered ring heteroaryls are pyridyl, pyrazinyl, pyrimidinyl, triazinyl and pyridazinyl.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S and B, and wherein the ring-forming carbon atoms and heteroatoms of the heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2 fused rings) systems. Included in heterocycloalkyl are monocyclic and polycyclic 12, 4-12, 3-10-, 4-10-, 3-7-, 4-7-, and 5-6-membered heterocycloalkyl groups. Heterocycloalkyl groups can also include spirocycles and bridged rings (e.g., a 5-14 membered bridged biheterocycloalkyl ring having one or more of the ring-forming carbon atoms replaced by a heteroatom independently selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 14 ring-forming atoms, 4 to 14 ring-forming atoms, 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, the term "alkylene" refers a divalent straight chain or branched alkyl linking group. Examples of "alkylene groups" include methylene, ethan-1,1-diyl, ethan-1,2-diyl, propan-1,3-diyl, propan-1,2-diyl, propan-1,1-diyl and the like.

As used herein, the term "alkenylene" refers a divalent straight chain or branched alkenyl linking group. Examples of "alkenylene groups" include ethen-1,1-diyl, ethen-1,2- diyl, propen-1,3-diyl, 2-buten-1,4-diyl, 3-penten-1,5-diyl, 3-hexen-1,6-diyl, 3-hexen-1,5-diyl, and the like.

As used herein, the term "alkynylene" refers a divalent straight chain or branched alkynyl linking group. Examples of "alkynylene groups" include propyn-1,3-diyl, 2-butyn-1,4-diyl, 3-pentyn-1,5-diyl, 3-hexyn-1,6-diyl, 3-hexyn-1,5-diyl, and the like.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means that each occurrence of a variable or substituent are independently selected at each occurrence from the applicable list.

As used herein, the term "one of $R^A$ and one of $R^B$ taken together form a linking group $L^2$" means: i) Ring moiety A has been substituted with at least one $R^A$ group ortho to the bond connecting Ring moiety A to the —$NR^2$—C(=O)— moiety, ii) Ring moiety B has been substituted with at least one $R^B$ group ortho to the bond connecting Ring moiety B to the —$NR^{2'}$—C(=O)-moiety, and iii) taken together $R^A$ and $R^B$ form the linking group $L^2$ the definition of which is independent of the definitions of substitutents $R^A$ and $R^B$ before combination.

As used herein, the term "one of $R^D$ and one of $R^C$ taken together form a linking group $L^3$" means: i) Ring C has been substituted with at least one $R^C$ group, ii) Ring D has been substituted with at least one $R^D$ group, and iii) taken together $R^D$ and $R^C$ form the linking group $L^3$ the definition of which is independent of the definitions of substitutents $R^C$ and $R^D$ before combination.

As used herein, the term "$R^5$ and one of $R^C$ taken together form a linking group $L^3$" means: i) Ring C has been substituted with at least one $R^C$ group, ii) taken together $R^5$ and one of $R^C$ form the linking group $L^3$ the definition of which is independent of the definitions of substitutents $R^5$ and $R^C$ before combination.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention, Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art.

An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as (3-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of formula 1-8 can be synthesized using a process shown in Scheme 1. Nucleophilic aromatic substitution of an appropriately functionalized nitro-halo-phenyl compound 1-1 with an amine containing a linker group [L¹]$_n$ 1-2 can afford compound 1-3. Alternatively, transition metal (including, but not limited to, Pd and Cu) catalyzed C—N bond forming reactions may also be used to provide compound 1-3. Reduction of the aromatic nitro group followed by ring closing reaction with cyanogen bromide can provide the aminobenzimidazole 1-5. Amide coupling of compound 1-5 with carboxylic acid 1-6 can generate the aminobenzimidazole 1-7. Removal of the Boc protecting group in 1-7 can then afford the amine 1-8.

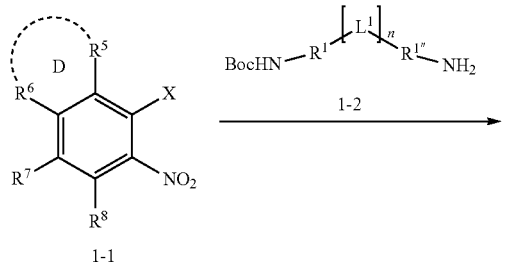

Scheme 1.

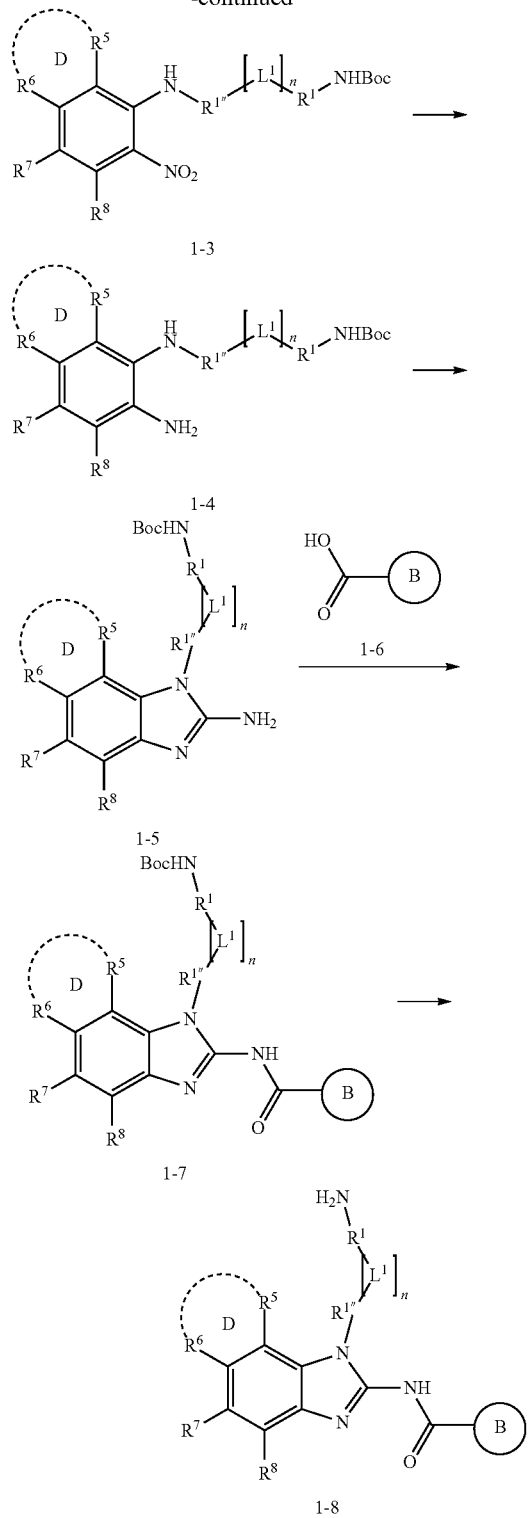

Compounds of formula 2-8 can be synthesized using a process shown in Scheme 2. Cyclization of halo-benzene compound 2-1 in one or more steps provides an appropriately functionalized bicyclic nitro-halo-phenyl compound 2-2. Nucleophilic aromatic substitution of compound 2-2 with amine 2-3 can afford compound 2-4. Alternatively, transition metal (e.g. Pd, Cu, etc.) catalyzed C—N bond forming reactions may also be used to provide compound 2-4. Reduction of the aromatic nitro group followed by ring closing reaction with cyanogen bromide can provide the aminobenzimidazole 2-6. Amide coupling of compound 2-6 with carboxylic acid 2-7 can generate the amide 2-8.

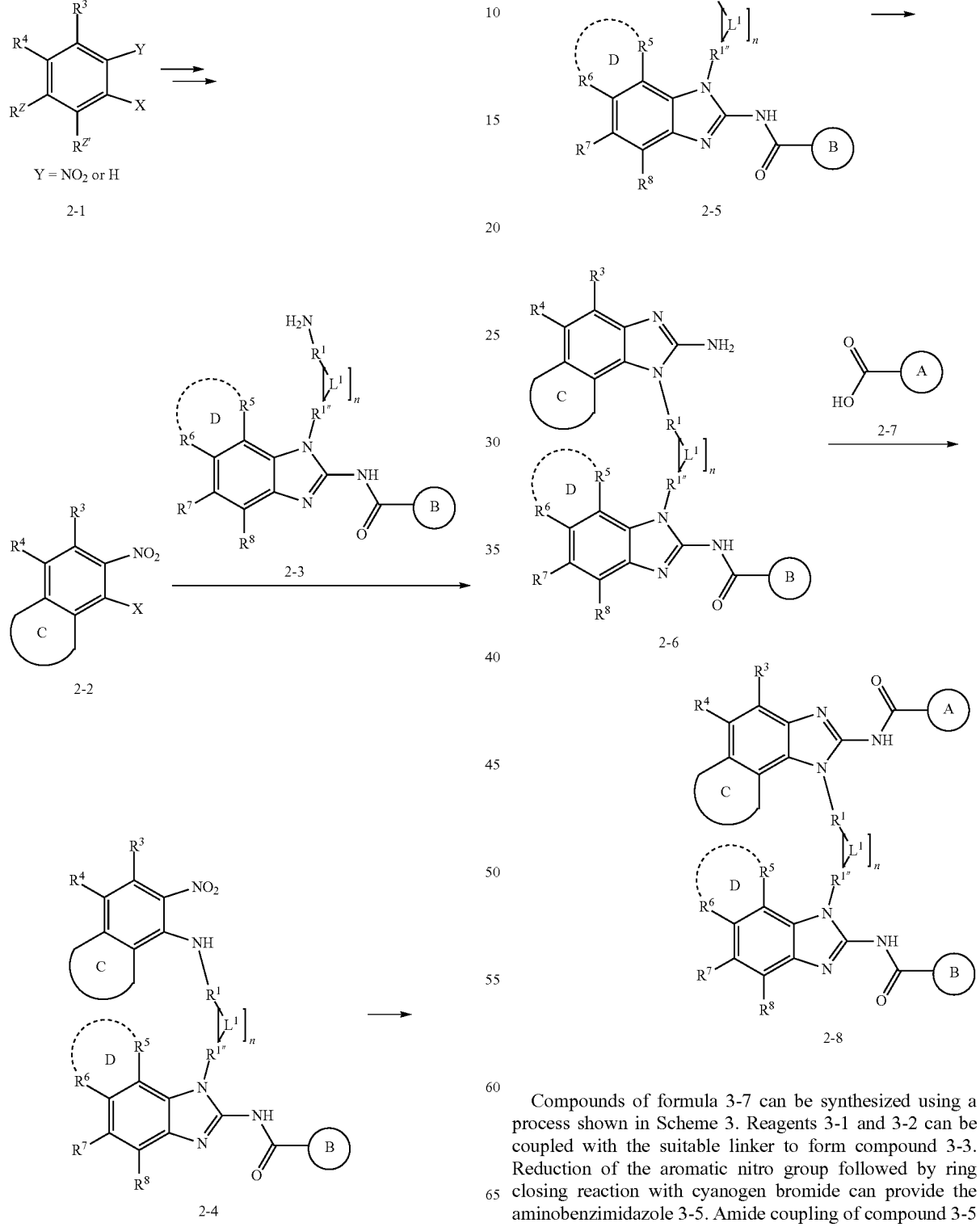

Compounds of formula 3-7 can be synthesized using a process shown in Scheme 3. Reagents 3-1 and 3-2 can be coupled with the suitable linker to form compound 3-3. Reduction of the aromatic nitro group followed by ring closing reaction with cyanogen bromide can provide the aminobenzimidazole 3-5. Amide coupling of compound 3-5 with carboxylic acid 3-6 can generate the amide 3-7.

Scheme 3.

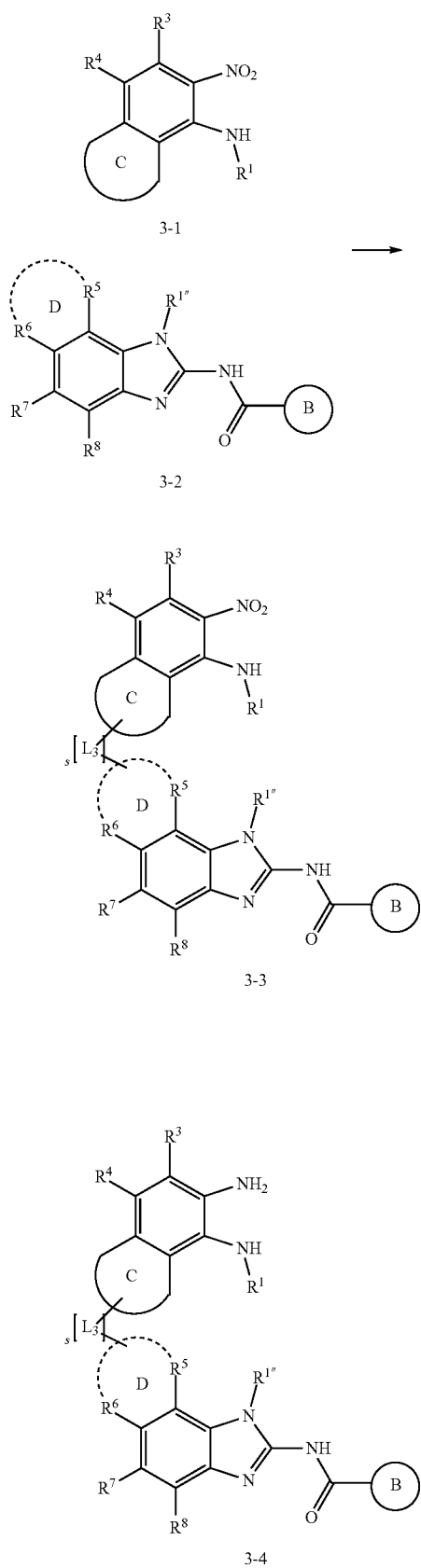

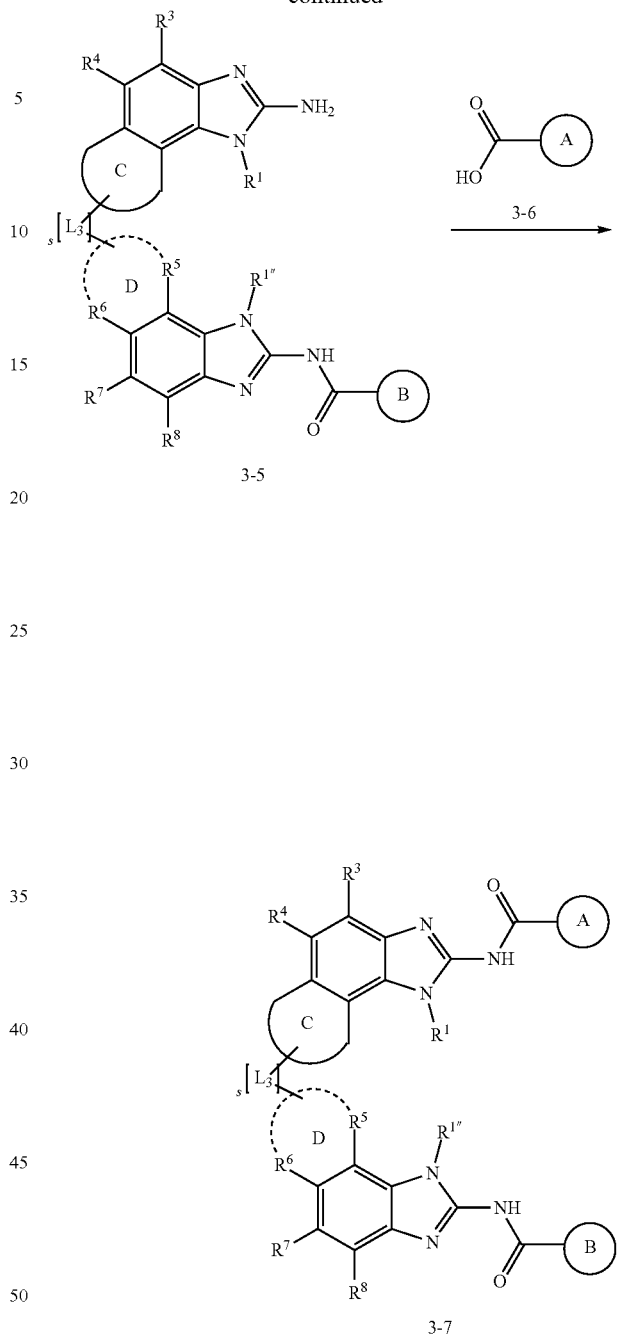

Compounds of formula 4-8 can be synthesized using a process shown in Scheme 4. Reagents 4-1 and 4-2 can be coupled with the suitable linker to form compound 4-3. Removal of the Boc protecting group in 4-3 and sequential intramolecular nucleophilic aromatic substitution can afford compound 4-5. Reduction of the aromatic nitro group followed by ring closing reaction with cyanogen bromide and amide coupling with carboxylic acid 4-7 can generate the target aminobenzimidazole 4-8.

Scheme 4.
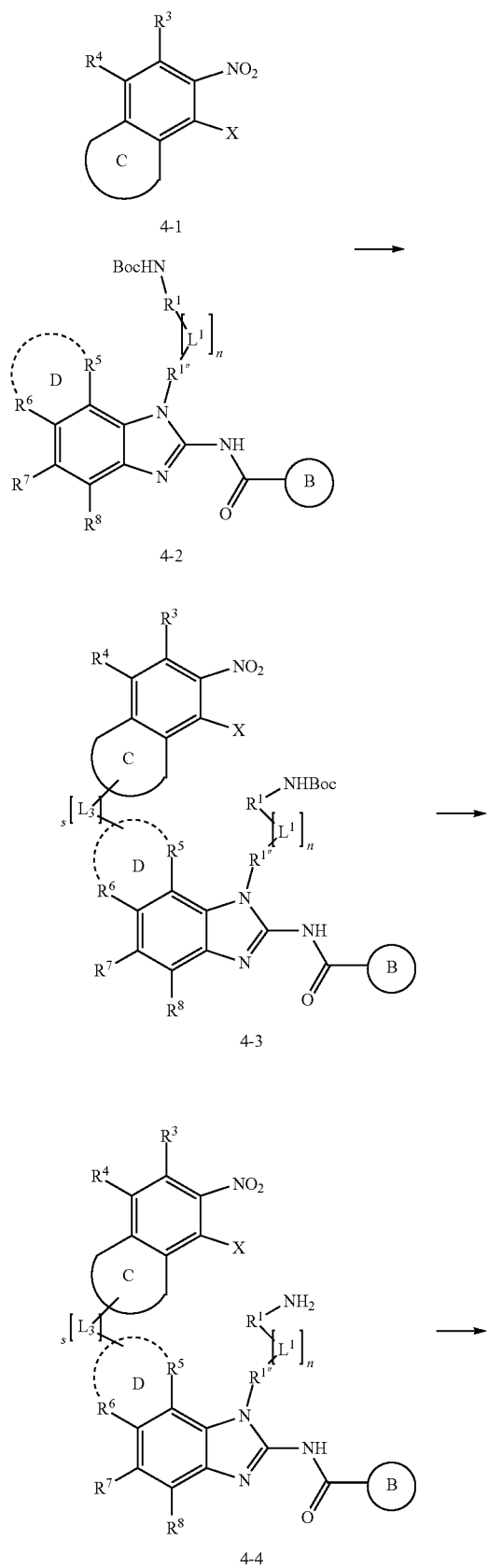
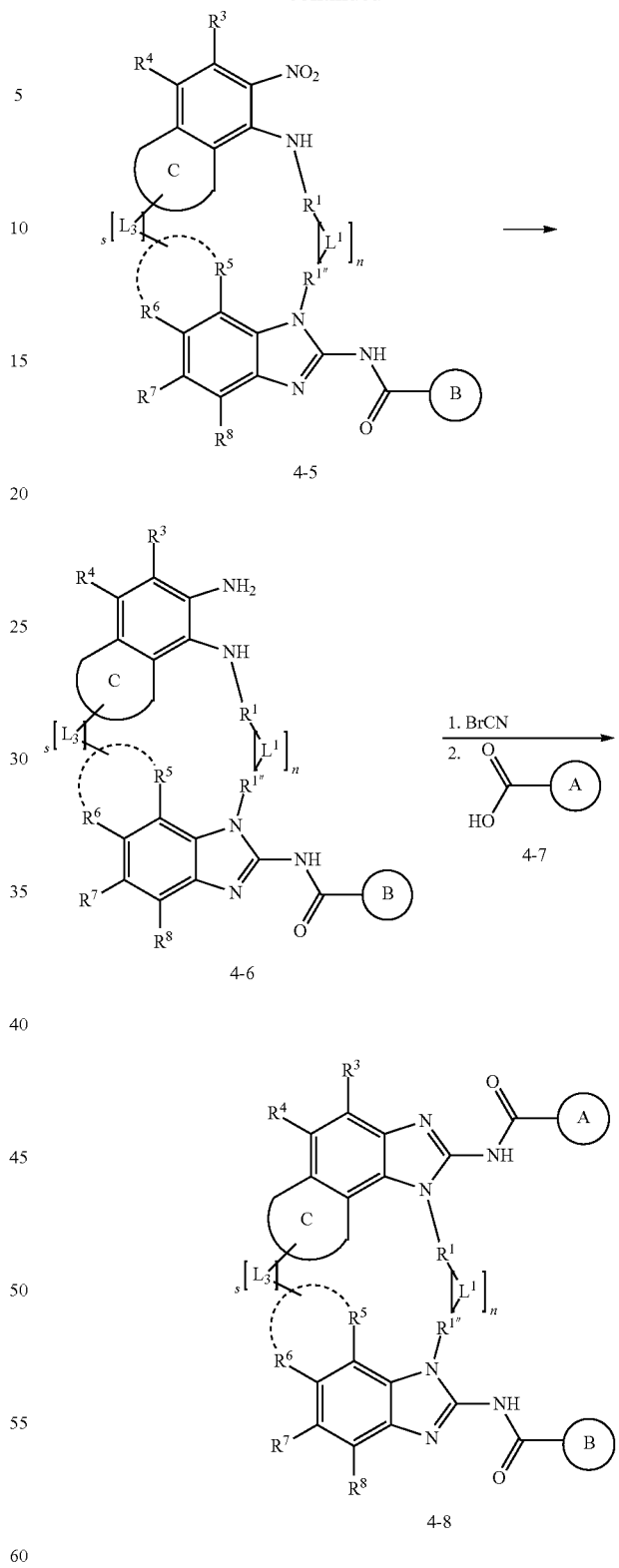
Compounds of formula 5-6 can be synthesized using a process shown in Scheme 5. Reagents 5-1 and 5-2 can be coupled with the suitable linker to form compound 5-3. Saponification of compound 5-3 can afford compound 5-4. Amide coupling of molecule 5-4 with 2-amino-benzimidazole 5-5 can generate the target molecule 5-6.

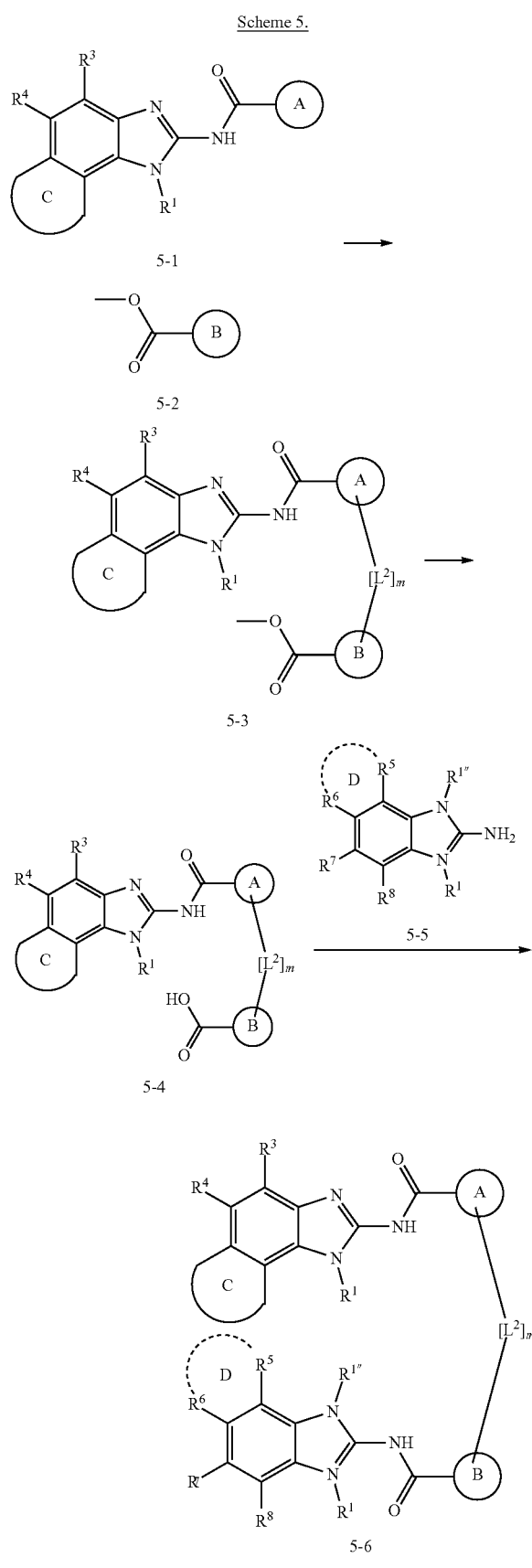

Scheme 5.

Compounds of formula 6-9 can be synthesized using a process shown in Scheme 6. Reagents 6-1 and 6-2 can be coupled with the suitable linker to form compound 6-3. Removal of the Boc protecting group in 6-3 and sequential nucleophilic aromatic substitution with halo-nitrophenyl 6-5 can afford compound 6-6. Alternatively, transition metal (e.g. Pd, Cu, etc.) catalyzed C—N bond forming reactions may also be used to provide compound 6-6. Reduction of the aromatic nitro group, followed by ring closing reaction with cyanogen bromide and intramolecular amide coupling with either the ester 6-8 or acid derivative 6-9 (generated through standard hydrolysis conditions of derivative 6-8) can provide the target aminobenzimidazole 6-10.

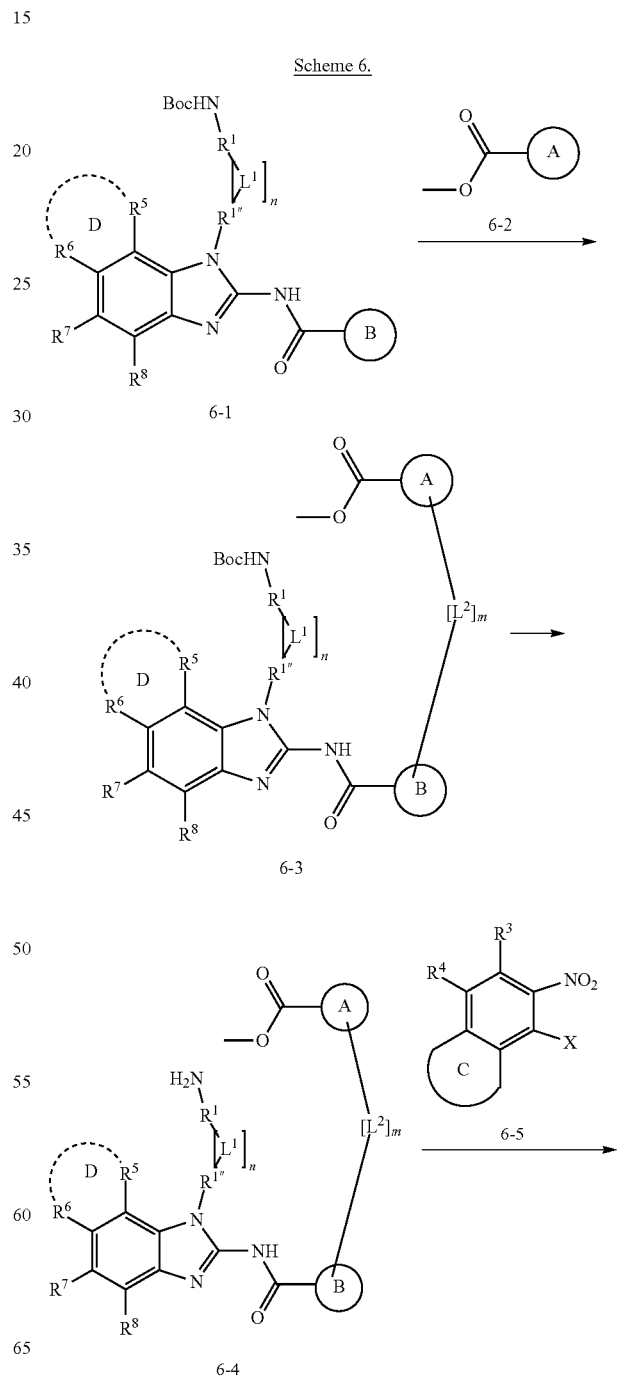

Scheme 6.

73
-continued

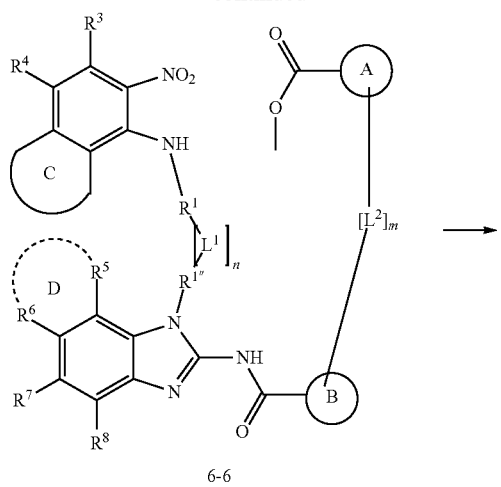
6-6

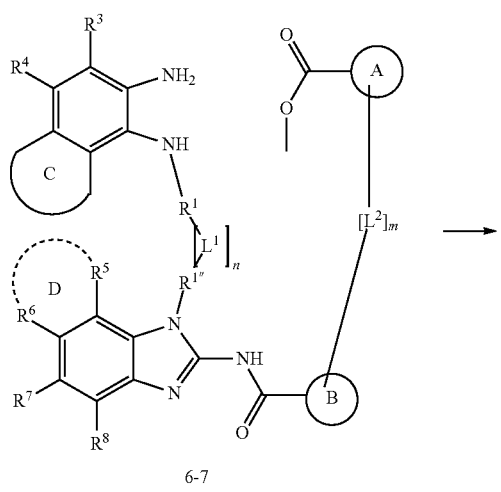
6-7

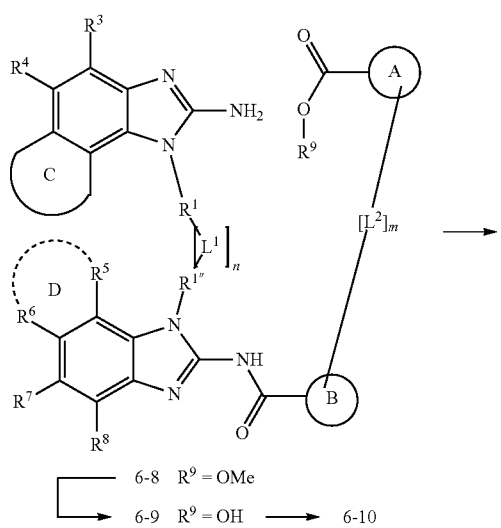
6-8  R⁹ = OMe
6-9  R⁹ = OH  →  6-10

74
-continued

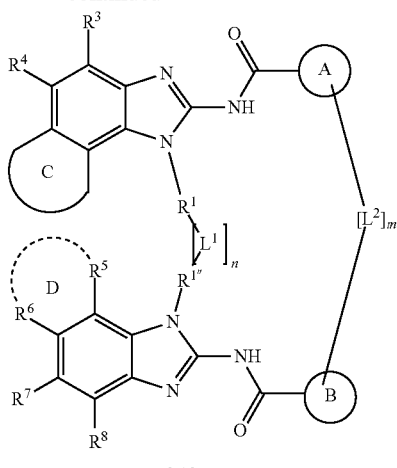
6-10

Compounds of formula 7-7 can be synthesized using a process shown in Scheme 7. Reagents 7-1 and 7-2 can be coupled with the suitable linker to form compound 7-3. Next, reagent 7-3 could be further coupled with compound 7-4 by linker [L³]ₛ to access intermediate 7-5. Finally, target compounds 7-7 can be accessed from an intramolecular amide coupling with either the ester 7-5 or acid derivative 7-6 (generated through standard hydrolysis conditions of derivative 7-5).

Scheme 7.

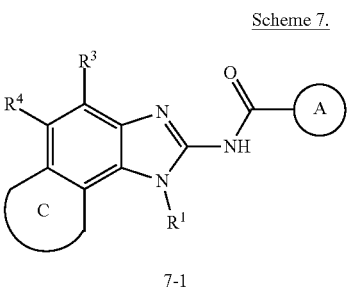
7-1

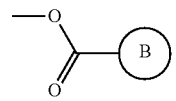
7-2

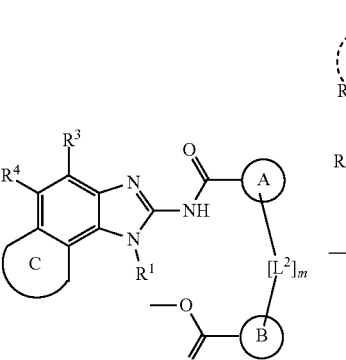
7-3

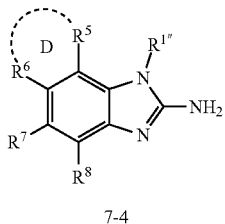
7-4

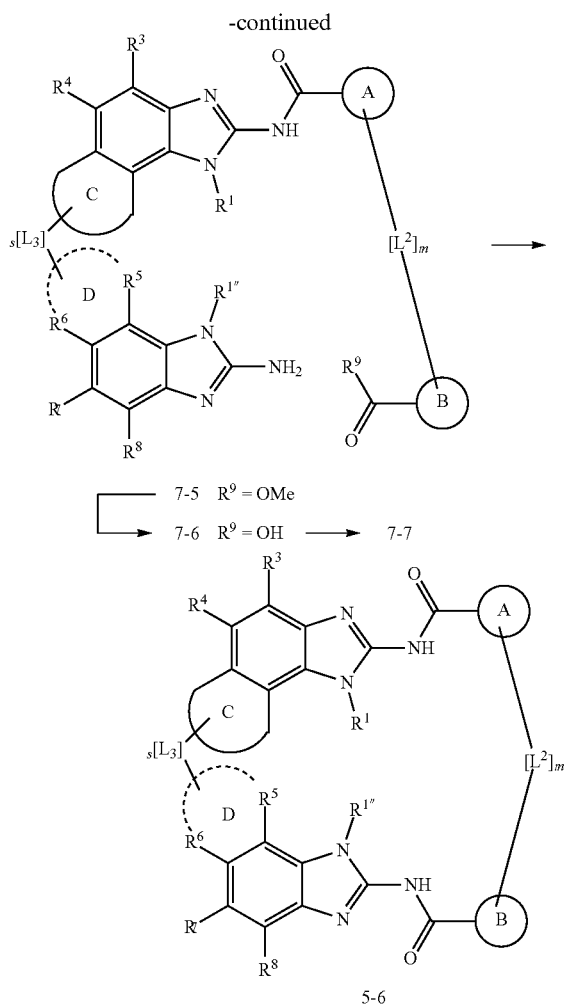

5-6

Methods of Use

Compounds of the present disclosure can activate STING-mediated IRF3 and NFκB signaling pathways to produce type I interferons and proinflammatory chemokines and cytokines and, thus, are useful in treating infectious diseases and cancer. In certain embodiments, the compounds of the present disclosure, or pharmaceutically acceptable salts or stereoisomers thereof, are useful for therapeutic administration to enhance, stimulate and/or increase immunity in cancer, chronic infection or sepsis, including enhancement of response to vaccination. In some embodiments, the present disclosure provides a method for inducing STING-mediated IRF3 and NFκB pathway activation. The method includes administering to an individual or a patient a compound of Formula (I) or of any of the formulas as described herein, or of a compound as recited in any of the claims and described herein, or a pharmaceutically acceptable salt or a stereoisomer thereof. The compounds of the present disclosure can be used alone, in combination with other agents or therapies or as an adjuvant or neoadjuvant for the treatment of diseases or disorders, including cancer or infection diseases. For the uses described herein, any of the compounds of the disclosure, including any of the embodiments thereof, may be used.

The compounds of the present disclosure activate STING, resulting in IRF3 and NFκB upregulation and production of IFNs and other cytokines. The production of those interferons and proinflammatory cytokines can enhance the immune response to cancerous cells and infectious diseases in mammals, including humans. In some embodiments, the present disclosure provides treatment of an individual or a patient in vivo using a compound of Formula (I) or a salt or stereoisomer thereof such that growth of cancerous tumors is inhibited. A compound of Formula (I) or of any of the formulas as described herein, or a compound as recited in any of the claims and described herein, or a salt or stereoisomer thereof, can be used to inhibit the growth of cancerous tumors. Alternatively, a compound of Formula (I) or of any of the formulas as described herein, or a compound as recited in any of the claims and described herein, or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound of Formula (I) or of any of the formulas as described herein, or of a compound as recited in any of the claims and described herein, or of a salt or stereoisomer thereof. In another embodiment, the present disclosure provides a method for inhibiting growth of tumor cells in an individual or a patient. The method includes administering to the individual or patient in need thereof a therapeutically effective amount of a compound of Formula (I) or of any of the formulas as described herein, or of a compound as recited in any of the claims and described herein, or a salt or a stereoisomer thereof.

In some embodiments, provided herein is a method for treating cancer. The method includes administering to a patient in need thereof, a therapeutically effective amount of a compound of Formula (I) or any of the formulas as described herein, a compound as recited in any of the claims and described herein, or a salt thereof. Examples of cancers include those whose growth may be inhibited using compounds of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a compound of Formula (I) or any of the formulas as described herein, a compound or composition as recited in any of the claims and described herein, or a salt thereof.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, colon cancer, lung cancer (e.g. non-small cell lung cancer and small cell lung cancer), squamous cell head and neck cancer, urothelial cancer (e.g. bladder) and cancers with high microsatellite instability (MSI$^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Induction of type I interferons and other proinflammatory cytokines/chemokines with compounds of the present disclosure can also be used for treating infections such as viral, bacteria, fungus and parasite infections. The present disclosure provides a method for treating infections such as viral infections. The method includes administering to a patient in need thereof, a therapeutically effective amount of a compound of Formula (I) or any of the formulas as described herein, a compound as recited in any of the claims and described herein, a salt thereof. Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, comovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus, tuberculosis and arboviral encephalitis virus.

The present disclosure provides a method for treating bacterial infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic bacteria causing infections treatable by methods of the disclosure include *Chlamydia*, rickettsial bacteria, mycobacteria, staphylococci, streptococci, pneumonococci, meningococci and conococci, *Klebsiella, Proteus, Serratia, Pseudomonas, Legionella*, diphtheria, *Salmonella*, bacilli, cholera, tetanus, botulism, anthrax, plague, leptospirosis, and Lyme's disease bacteria. The present disclosure provides a method for treating fungus infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic fungi causing infections treatable by methods of the disclosure include *Candida (albicans, krusei, glabrata, tropicalis*, etc.), *Cryptococcus neoformans, Aspergillus (fumigatus, niger*, etc.), Genus *Mucorales (mucor, absidia, rhizophus), Sporothrix schenkii, Blastomyces dermatitidis, Paracoccidioides brasiliensis, Coccidioides immitis* and *Histoplasma capsulatum*.

The present disclosure provides a method for treating parasite infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic parasites causing infections treatable by methods of the disclosure include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

The present disclosure provides a method for treating neurodegenerative diseases or disorders. The method includes administering to a patient in need thereof, a therapeutically effective amount of a compound of Formula (I) or any of the formulas as described herein, a compound as recited in any of the claims and described herein, or a salt thereof. Non-limiting examples of neurodegenerative diseases or disorders include Alzheimer's disease, Parkinson's disease, Huntington's disease, prion disease, Motor neurone diseases, Spinocerebellar ataxia and Spinal muscular atrophy.

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

Compounds of the present disclosure can be used in combination with one or more inhibitors or agonists of an immune checkpoint molecule for the treatment of diseases, such as cancer or infections. Exemplary immune checkpoint molecules such as CBL-B, CD20, CD27, CD28, CD40, CD122, CD96, CD73, CD47, CD160, KIR, LAIR1, 2B4, TGF beta, GITR, CSF1R, JAK, PI3K delta, PI3K gamma, TAM, arginase, HPK1, CD137 (also known as 4-1BB), ICOS, A2AR, IDO, B7-H3, B7-H4, BTFA, CTFA-4, FAG3, TIM3, TIGIT, CD112R, VISTA, PD-1, PD-L1 and PD-L2. In some embodiments, the compounds of the present disclosure can be used in combination with an inhibitor of an immune checkpoint molecule. In some embodiments, the compounds of the present disclosure can be used in combination with an agonist of an immune checkpoint molecule. In some embodiments, the inhibitor or agonist of the immune checkpoint molecule is an antibody, or antigen-binding fragment thereof. In some embodiments, the inhibitor or agonist of the immune checkpoint molecule is a small molecule, or a pharmaceutically acceptable salt thereof. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more inhibitors of an immune checkpoint molecule selected from KIR inhibitors, TIGIT inhibitors, LAIR1 inhibitors, CD160 inhibitors, 2B4 inhibitors and TGF beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. Antibodies that bind to human PD-1 include nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, and TSR-042. In some embodiments, the anti-PD-1 monoclonal antibody is nivolumab, pembrolizumab (also known as MK-3475), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab.

In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. Antibodies that bind to human PD-L1 include atezolizumab, avelumab, durvalumab, tislelizumab, BMS-935559, MEDI4736, FAZ053, KN035, CS1001, SHR-1316, CBT-502, A167, STI-A101, CK-301, BGB-A333, MSB-2311, HLX20, and LY3300054. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736. In some embodiments, the inhibitor of an immune checkpoint molecule is an inhibitor of PD-1 and PD-L1, e.g., an anti-PD-1/PD-L1 bispecific antibody. In some embodiments, the anti-PD-1/PD-L1 is MCLA-136.

In some embodiments, the inhibitor of an immune checkpoint molecule is an inhibitor of CTLA-4, e.g., an anti-CTLA-4 antibody. In some embodiments, the inhibitor or CTLA-4 is ipilimumab, tremelimumab, AGEN1884, or CP-675,206. In some embodiments, the inhibitor of an immune checkpoint molecule is an inhibitor of PD-L1 and CTLA-4, e.g., an anti-PD-L1/CTLA-4 bispecific antibody. Bispecific antibodies that bind to PD-L1 and CTLA-4 include AK104.

In some embodiments, the inhibitor of an immune checkpoint molecule is an inhibitor of LAG3, e.g., an anti-LAG3 antibody. In some embodiments, the inhibitor of LAG3 is BMS-986016, LAG525, INCAGN2385, or eftilagimod alpha (IMP321).

In some embodiments, the agonist of CD137 is urelumab. In some embodiments, the agonist of CD137 is utomilumab.

In some embodiments, the inhibitor of an immune checkpoint molecule is an inhibitor of CD73. In some embodiments, the inhibitor of CD73 is oleclumab or MEDI9447.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the inhibitor of TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164 (filed May 11, 2019), or a pharmaceutically acceptable salt thereof, each of which is incorporated herein by reference in its entirety.

In some embodiments, the agonist of an immune checkpoint molecule is an agonist of OX40, CD27, CD28, GITR, ICOS, CD40, TUR7/8, and CD137 (also known as 4-1BB).

In some embodiments, the agonist of an immune checkpoint molecule is an agonist of GITR, e.g., an anti-GITR antibody. In some embodiments, the agonist of GITR is TRX518, MK-4166, INCAGN1876, MK-1248, AMG228, BMS-986156, GWN323, MEDI1873, or MEDI6469.

In some embodiments, the agonist of an immune checkpoint molecule is an agonist of OX40, e.g., OX40 agonist antibody or OX40L fusion protein. In some embodiments, the agonist of OX40 is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104. In some embodiments, the bispecific antibody binds to PD-L1 and CD137. In some embodiments, the bispecific antibody that binds to PD-L1 and CD137 is MCLA-145.

In some embodiments, the compounds of the disclosure can be used in combination with one or more metabolic enzyme inhibitors. In some embodiments, the metabolic enzyme inhibitor is an inhibitor of IDO 1, TDO, or arginase. Examples of IDO 1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, and FAK kinase inhibitors such as, for example, those described in WO 2006/056399. Other agents such as therapeutic antibodies can be used in combination with the compounds of the present disclosure for treatment of STING-associated diseases, disorders or conditions. The one or more additional pharmaceutical agents can be administered to a patient simultaneously or sequentially.

The compounds as disclosed herein can be used in combination with one or more other enzyme/protein/receptor inhibitor therapies for the treatment of diseases, such as cancer, infections, and other diseases or disorders described herein. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections.

For example, the compounds of the present disclosure can be combined with one or more inhibitors of the following kinases for the treatment of cancer: Akt1, Akt2, Akt3, BCL2, CDK, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFaR, PDGFpR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCY54828), INCB62079), an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g. olaparib, rucaparib, veliparib or niraparib), a JAK inhibitor (JAK1 and/or JAK2, e.g., ruxobtinib, baricitinib, itacitinib (INCB39110), an IDO inhibitor (e.g., epacadostat, NLG919, or BMS-986205, MK7162), an LSD1 inhibitor (e.g., INCB59872 and INCB60003), a TDO inhibitor, a PI3K-delta inhibitor (e.g., parsaclisib (INCB50465) and INCB50797), a PI3K-gamma inhibitor such as PI3K-gamma selective inhibitor, a Pirn inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a chemokine receptor inhibitor (e.g. CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-I agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfdgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfdzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a compound of the present disclosure with an additional agent.

In some embodiments, the compounds of the disclosure can be used in combination with an inhibitor of JAK or PI3K5. The agents can be combined with the present compound in a single or continuous dosage form, or the agents can be administered simultaneously or sequentially as separate dosage forms.

Other anti-cancer agent(s) include antibody therapeutics such as trastuzumab (Herceptin), antibodies to costimulatory molecules such as CTLA-4 (e.g., ipilimumab), 4-1BB (e.g. urelumab, utomilumab), antibodies to PD-1 and PD-L1, or antibodies to cytokines (IL-10, TGF-β, etc.).

Examples of antibodies to PD-1 and/or PD-L1 that can be combined with compounds of the present disclosure for the treatment of cancer or infections such as viral, bacteria, fungus and parasite infections include, but are not limited to nivolumab, pembrolizumab, atezolizumab, durvalumab, avelumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, TSR-042, tislelizumab, BMS-935559, MEDI4736, FAZ053, KN035, CS1001, SHR-1316, CBT-502, A167, STI-A101, CK-301, BGB-A333, MSB-2311, HLX20, LY3300054, MCLA-136, and SHR-1210.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia*, Malaria, *Leishmania, Staphylococcus aureus, Pseudomonas Aeruginosa.*

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, comovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia*, rickettsial bacteria, mycobacteria, staphylococci, streptococci, pneumonococci, meningococci and conococci, *Klebsiella, Proteus, Serratia, Pseudomonas, Legionella*, diphtheria, *Salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida (albicans, krusei, glabrata, tropicalis,* etc.), *Cryptococcus neoformans, Aspergillus (fumigatus, niger,* etc.), Genus *Mucorales (mucor, absidia, rhizopus), Sporothrix schenkii,*

*Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

When more than one pharmaceutical agent is administered to a patient, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating STING in tissue samples, including human, and for identifying STING activators by inhibition binding of a labeled compound. Substitution of one or more of the atoms of the compounds of the present disclosure can also be useful in generating differentiated ADME (Adsorption, Distribution, Metabolism and Excretion.)

Accordingly, the present disclosure includes STING assays that contain such labeled or substituted compounds.

The present disclosure further includes isotopically-labeled compounds of the disclosure.

An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —CD$_3$ being substituted for —CH$_3$). In some embodiments, alkyl groups of the disclosed Formulas (e.g., Formula (I)) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —CD$_3$ being substituted for —CH$_3$). In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene and alkynylene linking groups, as described herein, are optionally replaced by deuterium atoms.

Synthetic methods for including isotopes into organic compounds are known in the art (Deuterium Fabeling in Organic Chemistry by Alan F. Thomas (New York, N.Y., Appleton-Century-Crofts, 1971; The Renaissance of H/D Exchange by lens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances, (see e.g., A. Kerekes et. al. *J. Med. Chem.* 2011, 54, 201-210; R. Xu et. al. J. *Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro STING labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful. It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind activate STING by monitoring its concentration variation when contacting with STING, through tracking of the labeling. For example, a test compound (labeled) can be evaluated for its ability to reduce binding of another compound which is known to bind to STING (i.e., standard compound). Accordingly, the ability of a test compound to compete with the standard compound for binding to STING directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of STING-associated diseases or disorders (such as, e.g., cancer, an inflammatory disease, a cardiovascular disease, or a neurodegenerative disease) which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi, Chem.,* 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.,* 5, 670 (2003); and "Preparative LC-MS Purification: Improved Compound Specific Method Optimization", K.

Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 30×100 mm or Waters XBridge™ $C_{18}$ 5 μm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ $C_{18}$ 5 μm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

Example 1. (E)-1-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazole-5-carboxamido)-7,8-dihydro-1H-[1,4]dioxino[2',3':3,4]benzo[1,2-d]imidazole-5-carboxamide

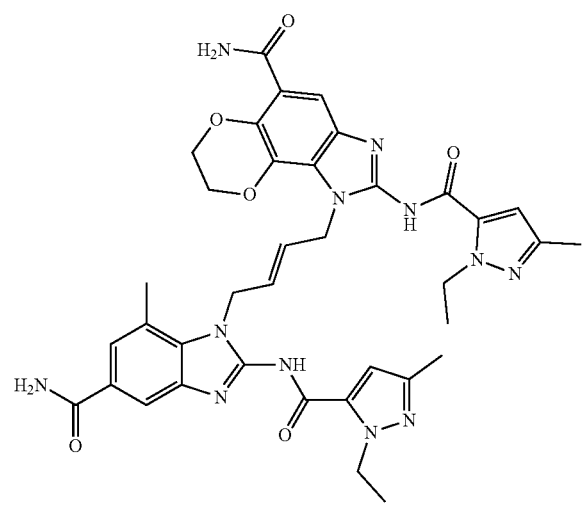 [SMILES: CCn1nc(C)cc1C(=O)Nc1nc2cc(C(N)=O)cc(C)c2n1C/C=C/Cn1c(NC(=O)c2cc(C)nn2CC)nc2cc(C(N)=O)c3c(c21)OCCO3]

Step 1: 4-fluoro-3-methyl-5-nitrobenzamide

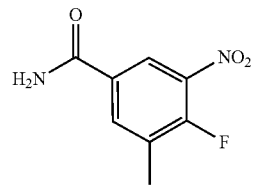

At 0° C., a mixture of nitric acid (2.51 mL, 39.2 mmol) and sulfuric acid (2.173 mL, 40.8 mmol) was added dropwise over 10 min into a solution of 4-fluoro-3-methylbenzamide (4.46 g, 29.1 mmol) in sulfuric acid (13.97 mL, 262 mmol). The mixture was stirred for 1.5 h while slowly warming up to room temperature (rt). The mixture was slowly poured into ice water (50 mL), and the precipitated solid was filtered and then washed with water (50 mL). The resulting solid residue was dried to provide the desired product as a white solid. LC-MS calculated for $C_8H_8FN_2O_3$ $(M+H)^+$: m/z=199.04; found 199.2.

Step 2: (E)-tert-butyl 4-(4-carbamoyl-2-methyl-6-nitrophenylamino)but-2-enylcarbamate

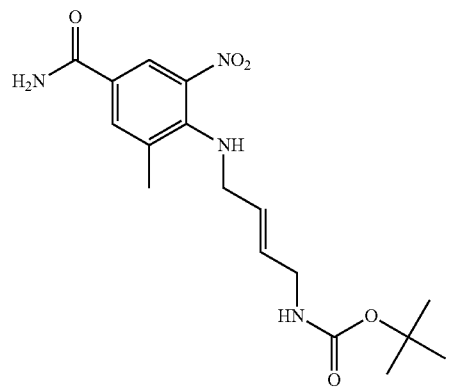 [SMILES: Cc1cc(C(N)=O)cc([N+](=O)[O-])c1NC/C=C/CNC(=O)OC(C)(C)C]

To a solution of 4-fluoro-3-methyl-5-nitrobenzamide (0.400 g, 2.019 mmol) and tert-butyl (E)-(4-aminobut-2-en-1-yl)carbamate (0.376 g, 2.019 mmol) (Ark Pharm, cat #AK308564) in dry DMSO (2.019 mL) was added $K_2CO_3$ (0.614 g, 4.44 mmol). The resulting yellow solution was stirred at room temperature for 1 h. The reaction mixture was diluted with water (15 mL) dropwise. The precipitated solid was filtered and then washed with water (10 mL). The resulting solid residue was dried to provide the desired product as a yellow solid. LC-MS calculated for $C_{17}H_{24}N_4NaO_5$ $(M+Na)^+$: m/z=387.2; found 387.2.

Step 3: (E)-tert-butyl 4-(2-amino-4-carbamoyl-6-methylphenylamino)but-2-enylcarbamate

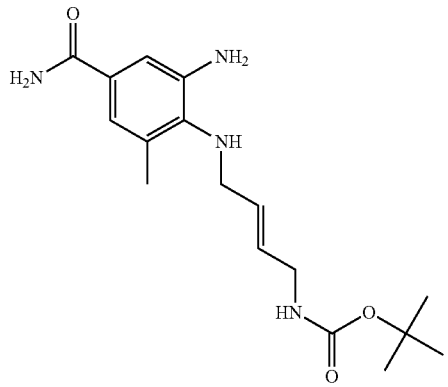

To a solution of tert-butyl (E)-(4-((4-carbamoyl-2-methyl-6-nitrophenyl)amino)but-2-en-1-yl)carbamate (220 mg, 0.604 mmol) in dioxane (1509 μL) and water (503 μL) was added ammonium chloride (226 mg, 4.23 mmol) and zinc (276 mg, 4.23 mmol) at 0° C. The reaction mixture was stirred at room temperature for 1 h, after which time it was filtered through a Celite® bed. The filtrate was partitioned between DCM and water. The organic layer was separated, dried over MgSO$_4$, filtered, and concentrated to provide the product. LC-MS calculated for $C_{17}H_{26}N_4NaO_3$ (M+Na)$^+$: m/z=357.2; found 357.3.

Step 4: (E)-tert-butyl 4-(2-amino-5-carbamoyl-7-methyl-1H-benzo[d]imidazol-1-yl)but-2-enylcarbamate

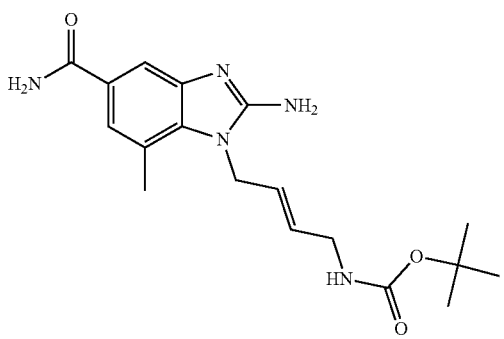 [SMILES: Cc1cc(C(N)=O)cc2nc(N)n(C/C=C/CNC(=O)OC(C)(C)C)c12]

To a solution of tert-butyl (E)-(4-((2-amino-4-carbamoyl-6-methylphenyl)amino)but-2-en-1-yl)carbamate (0.201 g, 0.60 mmol) in MeOH (2.000 mL) was added cyanogen bromide (0.047 mL, 0.900 mmol). The reaction mixture was stirred at room temperature for 1 h. The mixture was diluted with DCM, and washed with water and brine. The organic phase was dried over MgSO$_4$ before filtering. The filtrate was concentrated and purified by flash chromatography on a silica gel column eluting with 0 to 8% MeOH in DCM to afford the desired product. LC-MS calculated for $C_{18}H_{26}N_5O_3$ (M+H)$^+$: m/z=360.2; found 360.3.

Step 5: tert-butyl (E)-4-(5-carbamoyl-2-(1-ethyl-3-methyl-1H-pyrazole-5-carboxamido)-7-methyl-1H-benzo[d]imidazol-1-yl)but-2-enylcarbamate

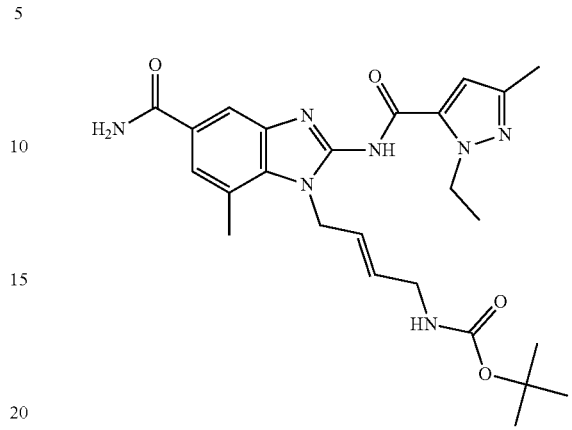

A mixture of 1-ethyl-3-methyl-1H-pyrazole-5-carboxylic acid (Combi-Blocks, cat #QB-0979: 93 mg, 0.60 mmol), tert-butyl (E)-(4-(2-amino-5-carbamoyl-7-methyl-1H-benzo[d]imidazol-1-yl)but-2-en-1-yl)carbamate (216 mg, 0.600 mmol), 2-(3H-[1,2,3]triazolo[4,5-b]pyridin-3-yl)-1,1,3,3-tetramethylisouronium hexafluorophosphate(V) (274 mg, 0.720 mmol), and N,N-diisopropylethylamine (209 μL, 1.200 mmol) in DMF (2000 μL) was stirred at room temperature for 2 h. The mixture was concentrated under reduced pressure. The mixture was then diluted with DCM and water, and the layers were separated. The aqueous layer was further extracted with DCM and the combined organic layers were washed with brine, dried over Na$_2$SO$_4$, filtered, and concentrated in vacuo. The crude residue was purified by flash chromatography on a silica gel column eluting with 0 to 8% MeOH in DCM to afford the desired product. LC-MS calculated for $C_{25}H_{34}N_7O_4$ (M+H)$^+$: m/z=496.3; found 496.3.

Step 6: (E)-1-(4-aminobut-2-enyl)-2-(1-ethyl-3-methyl-1H-pyrazole-5-carboxamido)-7-methyl-1H-benzo[d]imidazole-5-carboxamide

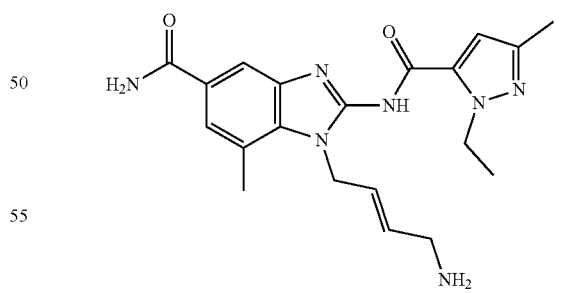

To a solution of tert-butyl (E)-(4-(5-carbamoyl-2-(1-ethyl-3-methyl-1H-pyrazole-5-carboxamido)-7-methyl-1H-benzo[d]imidazol-1-yl)but-2-en-1-yl)carbamate (180.0 mg, 0.363 mmol) in DCM (2.0 mL) was added TFA (0.2 mL). The resulting solution was stirred at room temperature for 0.5 h. The reaction mixture was quenched by NaHCO$_3$ aqueous solution then extracted with DCM. The organic phases were combined and dried over MgSO$_4$, then filtered.

The filtrate was concentrated and used directly in the next step without further purification. For characterization purposes, the crude material was purified by prep HPLC (pH=2, water+TFA) to provide the desired compound as its TFA salt. LC-MS calculated for $C_{20}H_{26}N_7O_2$ (M+H)$^+$: m/z=396.2; found 396.3. $^1$H NMR (400 MHz, DMSO) 7.87 (m, 2H), 7.69 (br s, 2H), 7.57 (s, 1H), 7.30 (s, 1H), 6.64 (s, 1H), 6.10 (dt, J=16.0, 4.8 Hz, 1H), 5.33 (dt, J=16.0, 6.4 Hz, 1H), 5.06 (brs, 2H), 4.59 (q, J=6.8 Hz, 2H), 3.42 (dt, J=6.4 Hz, 4.8 Hz, 2H), 2.63 (s, 3H), 2.16 (s, 3H), 1.34 (t, J=6.8 Hz, 3H).

Step 7: ethyl 8-bromo-2,3-dihydrobenzo[b][1,4]dioxine-5-carboxylate

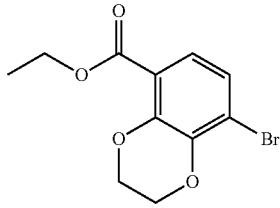 [SMILES: CCOC(=O)c1ccc(Br)c2c1OCCO2]

To a vial was added ethyl 4-bromo-2,3-dihydroxybenzoate (AstaTech, cat #53231: 0.950 g, 3.64 mmol), DMF (36.4 mL), 1,2-dibromoethane (0.408 mL, 4.73 mmol), a stir bar, and potassium carbonate (1.106 g, 8.01 mmol). The mixture was sealed and heated at 50° C. overnight with stirring. After cooling to rt, the mixture was concentrated in vacuo and the resulting residue was diluted with water and CHCl$_3$/IPA (3:1). The layers were separated, and the aqueous layer was further extracted. The combined organic extracts were dried over MgSO$_4$, filtered, and concentrated in vacuo to provide the desired product as a brown oil. LC-MS calculated for $C_{11}H_{12}BrO_4$ (M+H)$^+$: m/z=287.0/289.0; found 287.0/289.0.

Step 8: 8-bromo-2,3-dihydrobenzo[b][1,4]dioxine-5-carboxamide

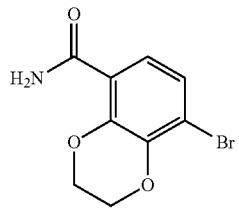 [SMILES: NC(=O)c1ccc(Br)c2c1OCCO2]

To a vial was added ethyl 8-bromo-2,3-dihydrobenzo[b][1,4]dioxine-5-carboxylate (1.08 g, 3.76 mmol) and 30% ammonium hydroxide (9.23 mL, 237 mmol). The reaction was stirred at 50° C. for 2 d. At this time, the solid was filtered and washed with water to provide the desired compound as a yellow solid. LC-MS calculated for $C_9H_9BrNO_3$ (M+H)$^+$: m/z=258.0/260.0; found 258.0/260.0.

Step 9: 8-bromo-7-nitro-2,3-dihydrobenzo[b][1,4]dioxine-5-carboxamide

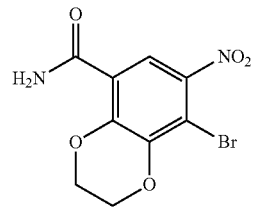 [SMILES: NC(=O)c1cc([N+](=O)[O-])c(Br)c2c1OCCO2]

A flask was charged with 8-bromo-2,3-dihydrobenzo[b][1,4]dioxine-5-carboxamide (0.540 g, 2.092 mmol) and a stir bar, then the flask was cooled to 0° C. Sulfuric acid (13.95 mL) was added dropwise with stirring. To a separate flask containing sulfuric acid (6.97 mL), cooled to 0° C., was added 70% nitric acid (0.181 mL, 2.82 mmol) dropwise. The resulting nitrite solution was transferred to an addition funnel, and added to the sulfuric acid/aryl amide mixture, dropwise, over a period of 10 min. After the addition, the mixture was warmed to rt, and stirred for 5 min. The mixture was poured over ice, and diluted with DCM. The layers were separated and the aqueous layer was further extracted with DCM. The combined organic extracts were dried over MgSO$_4$, filtered, and concentrated under reduced pressure. The resulting solid was a mixture of regioisomers, which was then washed with water, then 1:1 DCM/MeOH. The remaining solid was the desired regioisomer, and the filtrate was a mixture of both isomers. The filtrate was concentrated and purified by column chromatography (60% EtOAc/DCM) with the desired regioisomer eluting second. LC-MS calculated for $C_9H_8BrN_2O_5$ (M+H)$^+$: m/z=303.0/305.0; found 303.0/305.0.

Step 10: (E)-1-(4-(8-carbamoyl-6-nitro-2,3-dihydrobenzo[b][1,4]dioxin-5-ylamino)but-2-enyl)-2-(1-ethyl-3-methyl-1H-pyrazole-5-carboxamido)-7-methyl-1H-benzo[d]imidazole-5-carboxamide

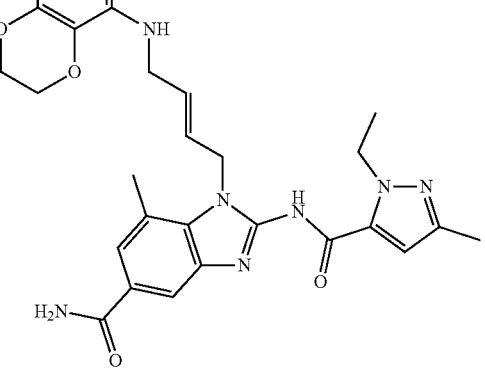

To a vial was added (E)-1-(4-aminobut-2-en-1-yl)-2-(1-ethyl-3-methyl-1H-pyrazole-5-carboxamido)-7-methyl-1H-benzo[d]imidazole-5-carboxamide (0.126 g, 0.269 mmol), 8-bromo-7-nitro-2,3-dihydrobenzo[b][1,4]dioxine-5-carboxamide (0.082 g, 0.269 mmol), BINAP (0.020 g, 0.032 mmol), tris(dibenzylideneacetone)dipalladium(0) (0.025 g, 0.027 mmol), cesium carbonate (0.438 g, 1.345 mmol), and a stir bar. The vial was then evacuated and flushed with nitrogen (3×). Dioxane (5.4 mL) was then added under nitrogen, and the reaction vial was then heated to 90° C. with stirring overnight. After cooling to rt, the mixture was filtered over Celite®, and concentrated under reduced pressure. The crude residue was used directly in the next step without further purification. LC-MS calculated for $C_{29}H_{32}N_9O_7$ (M+H)$^+$: m/z=618.2; found 618.3.

Step 11: (E)-1-(4-(6-amino-8-carbamoyl-2,3-dihydrobenzo[b][1,4]dioxin-5-ylamino)but-2-enyl)-2-(1-ethyl-3-methyl-1H-pyrazole-5-carboxamido)-7-methyl-1H-benzo[d]imidazole-5-carboxamide

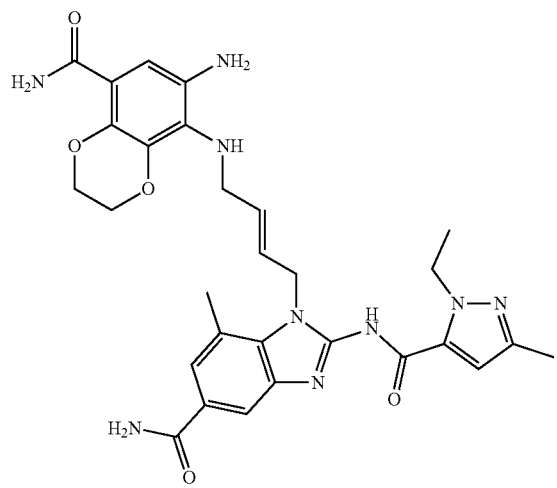 [SMILES: CCn1nc(C)cc1C(=O)Nc1nc2cc(C(N)=O)cc(C)c2n1C/C=C/CNc1c(N)cc(C(N)=O)c2c1OCCO2]

To a solution of (E)-1-(4-(8-carbamoyl-6-nitro-2,3-dihydrobenzo[b][1,4]dioxin-5-ylamino)but-2-enyl)-2-(1-ethyl-3-methyl-1H-pyrazole-5-carboxamido)-7-methyl-1H-benzo[d]imidazole-5-carboxamide (0.165 g, 0.267 mmol) in dioxane (4 mL)/water (1.3 mL) was added ammonium chloride (0.107 g, 2.0 mmol) and zinc (0.131 g, 2.0 mmol) at 0° C. The reaction mixture was stirred at rt for 10 min, then it was filtered. The filtrate was partitioned between $H_2O$ (10 mL) and 3:1 $CHCl_3$/IPA (30 mL). The organic layer was separated, dried over $MgSO_4$, concentrated, and dried under high vacuum to provide the desired product as an orange foam. LC-MS calculated for $C_{29}H_{34}N_9O_5$ (M+H)$^+$: m/z=588.3; found 588.3.

Step 12: (E)-2-amino-1-(4-(5-carbamoyl-2-(1-ethyl-3-methyl-1H-pyrazole-5-carboxamido)-7-methyl-1H-benzo[d]imidazol-1-yl)but-2-en-1-yl)-7,8-dihydro-1H-[1,4]dioxino[2′3′: 3,4]benzo[1,2-d]imidazole-5-carboxamide

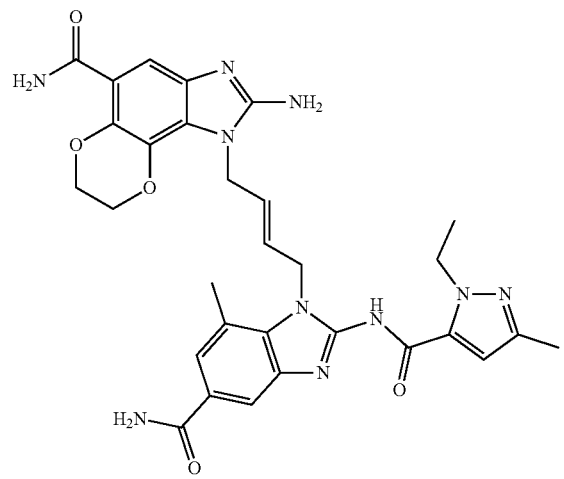 [SMILES: CCn1nc(C)cc1C(=O)Nc1nc2cc(C(N)=O)cc(C)c2n1C/C=C/Cn1c(N)nc2cc(C(N)=O)c3c(c21)OCCO3]

To a vial was added (E)-1-(4-((6-amino-8-carbamoyl-2,3-dihydrobenzo[b][1,4]dioxin-5-yl)amino)but-2-en-1-yl)-2-(1-ethyl-3-methyl-1H-pyrazole-5-carboxamido)-7-methyl-1H-benzo[d]imidazole-5-carboxamide (0.158 g, 0.269 mmol) and MeOH (2.69 mL). Cyanogen bromide (0.085 g, 0.807 mmol) was added and the reaction was stirred for 30 min at rt. The product was then triturated using EtOAc (5 mL), which was then filtered, washed with EtOAc, and dried. LC-MS calculated for $C_{30}H_{33}N_{10}O_5$ (M+H)$^+$: m/z=613.3; found 613.2.

Step 13: (E)-1-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazole-5-carboxamido)-7,8-dihydro-1H-[1,4]dioxino[2′,3′:3,4]benzo[1,2-d]imidazole-5-carboxamide To a solution of 1-Ethyl-3-methyl-1H-pyrazole-5-carboxylic acid (Combi-Blocks, cat #QB-0979: 0.070 g, 0.457 mmol) in DMF (2.285 mL) was added HATU (0.174 g, 0.457 mmol) and triethylamine (0.159 mL, 1.143 mmol). The mixture was stirred for 5 min then (E)-2-amino-1-(4-(5-carbamoyl-2-(1-ethyl-3-methyl-1H-pyrazole-5-carboxamido)-7-methyl-1H-benzo[d]imidazol-1-yl)but-2-en-1-yl)-7,8-dihydro-1H-[1,4]dioxino[2′,3′:3,4]benzo[1,2-d]imidazole-5-carboxamide (0.140 g, 0.229 mmol) was added and stirred overnight. The reaction mixture was diluted with MeCN and was then purified by prep-HPLC (pH=2, acetonitrile/water+TFA) to provide the desired compound as its TFA salt. LC-MS calculated for $C_{37}H_{41}N_{12}O_6$ (M+H)+: m/z=749.3; found 749.3.

Example 2. (E)-1-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide

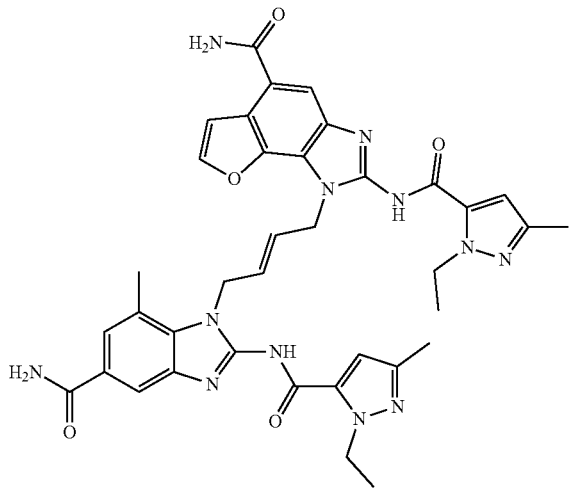 [SMILES: CCn1nc(C)cc1C(=O)Nc1nc2cc(C(N)=O)cc(C)c2n1C/C=C/Cn1c(NC(=O)c2cc(C)nn2CC)nc2cc(C(N)=O)c3ccoc3c21]

Step 1: methyl 2-bromo-4-chloro-3-hydroxy-5-nitrobenzoate

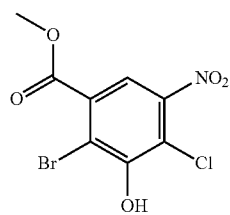 [SMILES: COC(=O)c1cc([N+](=O)[O-])c(Cl)c(O)c1Br]

To a solution of t-butylamine (1.774 mL, 16.88 mmol) in dry toluene (11.25 mL) was added bromine (0.319 mL, 6.19 mmol) dropwise at −30° C. (~10 min) under nitrogen. The mixture was cooled to −78° C., and a solution of methyl 4-chloro-3-hydroxy-5-nitrobenzoate (Combi-Blocks, cat #CA-5786: 1.3030 g, 5.63 mmol) in DCM (45.0 mL) was added dropwise under nitrogen (30 min). The mixture was warmed to rt gradually and stirred overnight. The reaction was diluted with EtOAc and the organic phase washed with 1.0 M HCl (2×) and brine (1×). The organic phase was dried over anhydrous MgSO$_4$, filtered, and the filtrate evaporated under reduced pressure. The residue was purified by flash chromatography (10% EtOAc/hexanes) to give the desired product as a white solid. LC-MS calculated for C$_8$H$_6$BrClNO$_5$ (M+H)$^+$: m/z=309.9/311.9; found 309.8/312.0.

Step 2: methyl 3-acetoxy-2-bromo-4-chloro-5-nitrobenzoate

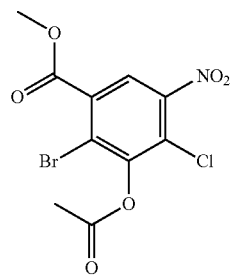 [SMILES: COC(=O)c1cc([N+](=O)[O-])c(Cl)c(OC(C)=O)c1Br]

To a solution of methyl 2-bromo-4-chloro-3-hydroxy-5-nitrobenzoate (1.37 g, 4.41 mmol) and triethylamine (1.845 mL, 13.24 mmol) in CH$_2$Cl$_2$ (12.98 mL) was added Ac$_2$O (0.541 mL, 5.74 mmol) at 0° C. After stirring for 18 h at rt, the mixture was diluted with HCl (1 M, 10 mL). The resulting mixture was extracted with CH$_2$Cl$_2$ (3×10 mL). The combined organic layers were washed with brine, dried over MgSO$_4$ and concentrated in vacuo. The crude residue was then purified by flash chromatography (10% EtOAc/hexanes) to provide the desired product as a white solid. LC-MS calculated for C$_{10}$H$_8$BrClNO$_6$ (M+H)$^+$: m/z=351.9/353.9; found 351.9/353.8. $^1$H NMR (500 MHz, DMSO) δ 8.48 (s, 1H), 3.92 (s, 3H), 2.49 (s, 3H). $^{13}$C NMR (125 MHz, DMSO) δ 167.0, 163.6, 147.0, 146.8, 132.8, 124.4, 124.1, 122.1, 53.4, 20.0.

Step 3: methyl 3-acetoxy-4-chloro-5-nitro-2-((trimethylsilyl)ethynyl)benzoate

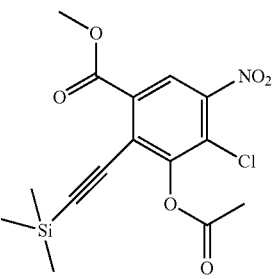 [SMILES: COC(=O)c1cc([N+](=O)[O-])c(Cl)c(OC(C)=O)c1C#C[Si](C)(C)C]

Methyl 3-acetoxy-2-bromo-4-chloro-5-nitrobenzoate (0.503 g, 1.427 mmol), cuprous iodide (0.027 g, 0.143 mmol) and dichlorobis(triphenylphosphine)-palladium(II) (0.050 g, 0.071 mmol) were added in a vial and the vial was sealed, evacuated and flushed with nitrogen (3×). Then DMF (3.57 mL) and DIPEA (1.189 mL) were added under nitrogen. After this ethynyltrimethylsilane (0.605 mL, 4.28 mmol) was added and reaction was stirred at 35° C. overnight. After cooling to rt, the mixture was diluted with DCM and 1 N HCl. The layers were separated, and the aqueous layer was further extracted. The combined organic layers were dried over MgSO$_4$, filtered, and concentrated in vacuo. The crude residue was then purified by flash chromatography (10% EtOAc/hexanes) to provide the desired product as a clear solid. LC-MS calculated for C$_{15}$H$_{17}$ClNO$_6$Si (M+H)$^+$: m/z=370.0; found 370.0.

Step 4: methyl 4-chloro-2-ethynyl-3-hydroxy-5-nitrobenzoate

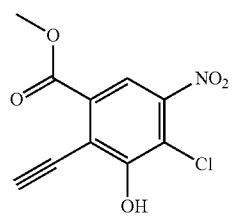 [SMILES: C#Cc1c(C(=O)OC)cc([N+](=O)[O-])c(Cl)c1O]

To a solution of methyl 3-acetoxy-4-chloro-5-nitro-2-((trimethylsilyl)ethynyl)benzoate (0.331 g, 0.895 mmol) in MeOH (8.95 mL) was added potassium carbonate (0.124 g, 0.895 mmol). The reaction was stirred for 15 min, and was then diluted with DCM and 1 N HCl. The layers were separated, and the aqueous layer was further extracted with DCM. The combined organic layers were dried over MgSO$_4$, filtered, and concentrated in vacuo. The resulting residue was then used directly in the next step without further purification. LC-MS calculated for C$_{10}$H$_7$ClNO$_5$ (M+H)$^+$: m/z=256.0; found 256.1.

Step 5: 7-chloro-6-nitrobenzofuran-4-carboxamide

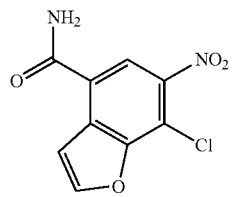 [SMILES: NC(=O)c1cc([N+](=O)[O-])c(Cl)c2occc12]

To a vial was added methyl 4-chloro-2-ethynyl-3-hydroxy-5-nitrobenzoate (201 mg, 0.786 mmol) and ammonium hydroxide (9186 μL, 236 mmol). The mixture was stirred at rt for 20 h, and was then filtered. The resulting solid was washed with water, dried, and used directly in the next step without further purification. LC-MS calculated for C9H$_6$ClN$_2$O$_4$ (M+H)$^+$: m/z=241.0; found 241.0. $^1$H NMR (500 MHz, DMSO) δ 8.53 (s, 1H), 8.51 (d, J=2.25 Hz, 1H), 8.35 (s, 1H), 7.76 (s, 1H), 7.54 (d, J=2.25 Hz, 1H). $^{13}$C NMR (125 MHz, DMSO) δ 165.6, 152.7, 150.6, 142.6, 131.5, 126.0, 120.0, 113.5, 108.8.

Step 6: (E)-1-(4-(4-carbamoyl-6-nitrobenzofuran-7-ylamino)but-2-enyl)-2-(1-ethyl-3-methyl-1H-pyrazole-5-carboxamido)-7-methyl-1H-benzo[d]imidazole-5-carboxamide

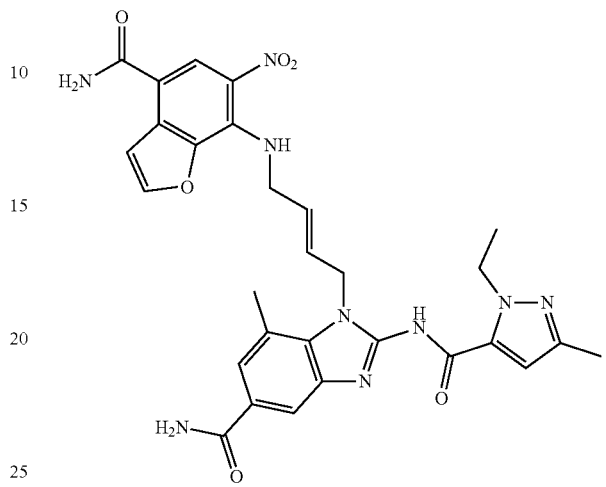

To a vial was added (E)-1-(4-aminobut-2-en-1-yl)-2-(1-ethyl-3-methyl-1H-pyrazole-5-carboxamido)-7-methyl-1H-benzo[d]imidazole-5-carboxamide (Example 1, Step 6: 0.1 g, 0.213 mmol), 7-chloro-6-nitrobenzofuran-4-carboxamide (0.051 g, 0.213 mmol), a stir bar, DMSO (1.067 mL), and DIPEA (0.186 mL, 1.067 mmol). The resulting mixture was sealed and heated at 80° C. overnight, then 100° C. for 8 h. After cooling to rt, the product was triturated with water, filtered, washed with cold water, and dried to provide the desired product as a beige solid. LC-MS calculated for C$_{29}$H$_{30}$N$_9$O$_6$ (M+H)$^+$: m/z=600.2; found 600.2.

Step 7: (E)-1-(4-(6-amino-4-carbamoylbenzofuran-7-ylamino)but-2-enyl)-2-(1-ethyl-3-methyl-1H-pyrazole-5-carboxamido)-7-methyl-1H-benzo[d]imidazole-5-carboxamide

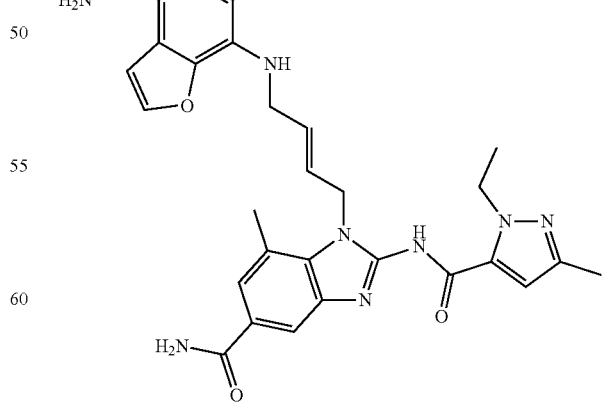

This compound was prepared using similar procedures as described for Example 1, Step 11 with (E)-1-(4-(4-carbamoyl-6-nitrobenzofuran-7-ylamino)but-2-enyl)-2-(1-ethyl-3-methyl-1H-pyrazole-5-carboxamido)-7-methyl-1H-benzo[d]imidazole-5-carboxamide replacing (E)-1-(4-(8-carbamoyl-6-nitro-2,3-dihydrobenzo[b][1,4]dioxin-5-ylamino)but-2-enyl)-2-(1-ethyl-3-methyl-1H-pyrazole-5-carboxamido)-7-methyl-1H-benzo[d]imidazole-5-carboxamide. LC-MS calculated for $C_{29}H_{32}N_9O_4$ (M+H)$^+$: m/z=570.3; found 570.3.

Step 8: (E)-2-amino-1-(4-(5-carbamoyl-2-(1-ethyl-3-methyl-1H-pyrazole-5-carboxamido)-7-methyl-1H-benzo[d]imidazol-1-yl)but-2-enyl)-1H-benzofuro[6,7-d]imidazole-5-carboxamide

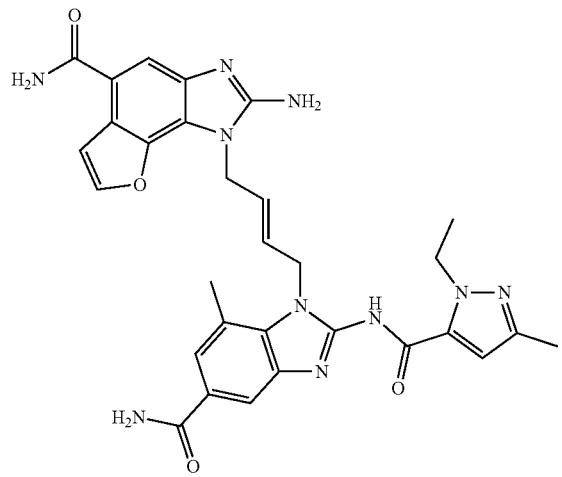 [SMILES: CCn1nc(C)cc1C(=O)Nc1nc2cc(C(N)=O)cc(C)c2n1C/C=C/Cn1c(N)nc2cc(C(N)=O)c3ccoc3c21]

This compound was prepared using similar procedures as described for Example 1, Step 12 with (E)-1-(4-(6-amino-4-carbamoylbenzofuran-7-ylamino)but-2-enyl)-2-(1-ethyl-3-methyl-1H-pyrazole-5-carboxamido)-7-methyl-1H-benzo[d]imidazole-5-carboxamide replacing (E)-1-(4-((6-amino-8-carbamoyl-2,3-dihydrobenzo[b][1,4]dioxin-5-yl)amino)but-2-en-1-yl)-2-(1-ethyl-3-methyl-1H-pyrazole-5-carboxamido)-7-methyl-1H-benzo[d]imidazole-5-carboxamide. LC-MS calculated for $C_{30}H_{33}N_{10}O_4$ (M+H)$^+$: m/z=595.3; found 595.3.

Step 9: (E)-1-(4-(5-carbamoyl-2-(1-ethyl-3-methyl-1H-pyrazole-5-carboxamido)-7-methyl-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide This compound was prepared using similar procedures as described for Example 1, Step 13 with (E)-2-amino-1-(4-(5-carbamoyl-2-(1-ethyl-3-methyl-1H-pyrazole-5-carboxamido)-7-methyl-1H-benzo[d]imidazol-1-yl)but-2-enyl)-1H-benzofuro[6,7-d]imidazole-5-carboxamide replacing (E)-2-amino-1-(4-(5-carbamoyl-2-(1-ethyl-3-methyl-1H-pyrazole-5-carboxamido)-7-methyl-1H-benzo[d]imidazol-1-yl)but-2-en-1-yl)-7,8-dihydro-1H-[1,4]dioxino[2',3':3,4]benzo[1,2-d]imidazole-5-carboxamide. The reaction mixture was diluted with MeCN, acidified with a few drops of TFA, and purified by prep-HPLC (pH=2, acetonitrile/water+TFA) to give the desired product as its TFA salt. LC-MS calculated for $C_{37}H_{39}N_{12}O_5$ (M+H)$^+$: m/z=731.3; found 731.3. $^1$H NMR (500 MHz, DMSO) δ 7.94 (d, J=2.0 Hz, 1H), 7.88 (br s, 1H), 7.85 (s, 1H), 7.84 (s, 1H), 7.45 (s, 1H), 7.39 (br s, 1H), 7.35 (d, J=2.0 Hz, 1H), 7.26 (br s, 1H), 6.55 (s, 1H), 6.47 (s, 1H), 5.81 (m, 1H), 5.65-5.55 (m, 1H), 4.98 (br s, 2H), 4.93 (br s, 2H), 4.54-4.50 (m, 2H), 4.49-4.44 (m, 2H), 2.39 (s, 3H), 2.12 (s, 3H), 2.09 (s, 3H), 1.26 (t, J=7.0 Hz, 3H), 1.22 (t, J=7.0 Hz, 3H).

Example 3. (E)-3-(((3-((5-carbamoyl-1-(4-(5-carbamoyl-2-(1-ethyl-3-methyl-1H-pyrazole-5-carboxamido)-1H-benzofuro[6,7-d]imidazol-1-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid

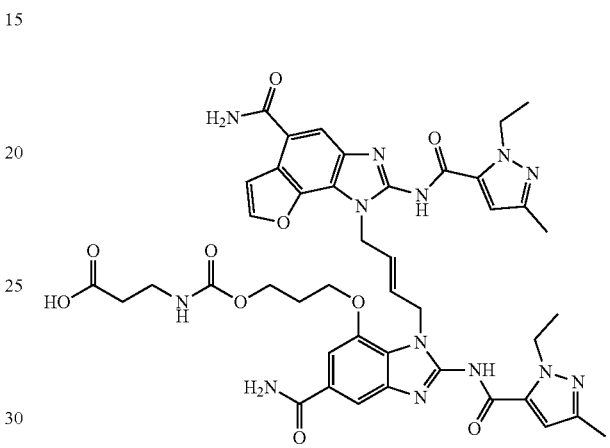

Step 1: tert-butyl (E)-(4-((4-carbamoyl-6-nitrobenzofuran-7-yl)amino)but-2-en-1-yl)carbamate

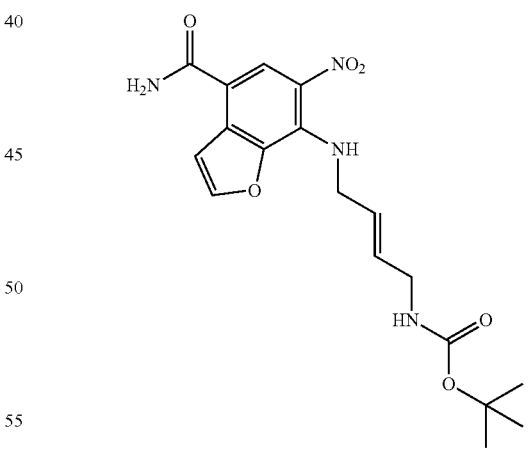

To a vial was added tert-butyl (E)-(4-aminobut-2-en-1-yl)carbamate (Ark Pharm, cat #AK308564: 0.140 g, 0.752 mmol), 7-chloro-6-nitrobenzofuran-4-carboxamide (Example 2, Step 5, 0.181 g, 0.752 mmol), a stir bar, EtOH (3.76 mL), and DIPEA (0.656 mL, 3.76 mmol). The resulting mixture was sealed and heated at 80° C. overnight, then 120° C. for 8 h. After cooling to rt, the mixture was concentrated and used directly in the next step. LC-MS calculated for $C_{18}H_{22}N_4O_6Na$ (M+Na)$^+$: m/z=413.2; found 413.2.

Step 2: tert-butyl (E)-(4-((6-amino-4-carbamoylbenzofuran-7-yl)amino)but-2-en-1-yl)carbamate

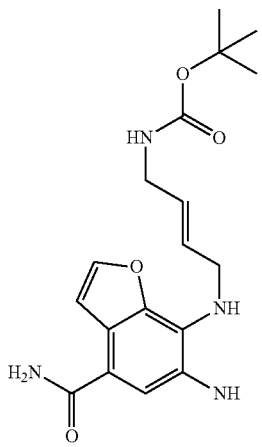 [SMILES: CC(C)(C)OC(=O)NC/C=C/CNc1c(N)cc(C(N)=O)c2ccoc12]

To a solution of tert-butyl (E)-(4-((4-carbamoyl-6-nitrobenzofuran-7-yl)amino)but-2-en-1-yl)carbamate (0.293 g, 0.751 mmol) in MeOH (11.25 mL) was added sodium hydrosulfite (0.653 g, 3.75 mmol) in water (2.364 mL, 131 mmol) and 30% aq. ammonium hydroxide (1.218 mL, 9.38 mmol) at 0° C. The reaction mixture was warmed to room temperature. After 10 min, $H_2O$ was added to the reaction mixture followed by extraction with ethyl acetate. The combined organic layers were dried over $MgSO_4$, filtered and concentrated to provide the desired product. LC-MS calculated for $C_{18}H_{24}N_4O_4Na$ $(M+Na)^+$: m/z=383.2; found 383.1.

Step 3: tert-butyl (E)-(4-(2-amino-5-carbamoyl-1H-benzofuro[6,7-d]imidazol-1-yl)but-2-en-1-yl) carbamate

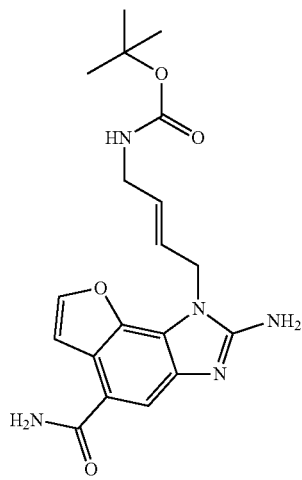 [SMILES: CC(C)(C)OC(=O)NC/C=C/Cn1c(N)nc2cc(C(N)=O)c3ccoc3c21]

To a solution of tert-butyl (E)-(4-((6-amino-4-carbamoylbenzofuran-7-yl)amino)but-2-en-1-yl)carbamate (0.270 g, 0.751 mmol) in MeOH (11.25 mL) was added cyanogen bromide (0.238 g, 2.252 mmol). After 1 hr, the reaction mixture was concentrated to dryness and the crude residue was used directly in the next step. LC-MS calculated for $C_{19}H_{24}N_5O_4$ $(M+H)^+$: m/z=386.2; found 386.2.

Step 4: tert-butyl (E)-(4-(5-carbamoyl-2-(1-ethyl-3-methyl-1H-pyrazole-5-carboxamido)-1H-benzofuro[6,7-d]imidazol-1-yl)but-2-en-1-yl)carbamate

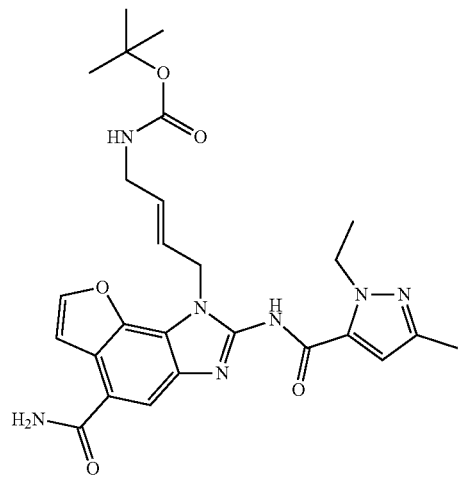 [SMILES: CCn1nc(C)cc1C(=O)Nc1nc2cc(C(N)=O)c3ccoc3c2n1C/C=C/CNC(=O)OC(C)(C)C]

To a solution of tert-butyl (E)-(4-(2-amino-5-carbamoyl-1H-benzofuro[6,7-d]imidazol-1-yl)but-2-en-1-yl)carbamate (289 mg, 0.751 mmol) in DMF (5 mL) was added DIPEA (1.049 mL, 6.00 mmol), 1-Ethyl-3-methyl-1H-pyrazole-5-carboxylic acid (Combi-Blocks, cat #QB-0979: 0.347 g, 2.252 mmol) and BOP (0.996 g, 2.252 mmol). After stirring overnight, $H_2O$ was added to the reaction mixture followed by extraction with $CHCl_3$/IPA (3:1). The combined organic layers were dried over $MgSO_4$, filtered, and concentrated. The crude product was added to a silica gel column and was eluted with methanol/dichloromethane from 0% to 10%. LC-MS calculated for $C_{26}H_{32}N_7O_5$ $(M+H)^+$: m/z=522.2; found 522.2.

Step 5: (E)-1-(4-aminobut-2-en-1-yl)-2-(1-ethyl-3-methyl-1H-pyrazole-5-carboxamido)-1H-benzofuro[6,7-d]imidazole-5-carboxamide

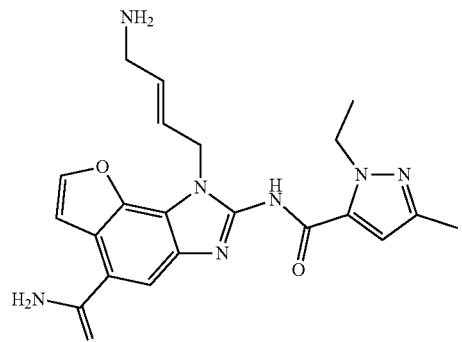

To a solution of tert-butyl (E)-(4-(5-carbamoyl-2-(1-ethyl-3-methyl-1H-pyrazol-5-carboxamido)-1H-benzofuro[6,7-d]imidazol-1-yl)but-2-en-1-yl)carbamate (0.300 g, 0.575 mmol) in 1,4-dioxane (5.75 mL) was added 4 N HCl in dioxane (1.438 mL, 5.75 mmol). The resulting solution was stirred for 1 h, then was triturated with EtOAc and filtered to provide the HCl salt. LC-MS calculated for $C_{21}H_{24}N_7O_3$ (M+H)$^+$: m/z=422.2; found 422.4.

Step 6: 4-chloro-3-hydroxy-5-nitrobenzamide

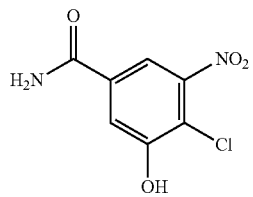 [SMILES: NC(=O)c1cc(O)c(Cl)c([N+](=O)[O-])c1]

In a round-bottomed flask, 4-chloro-3-methoxy-5-nitrobenzamide (Astatech, cat #97780: 1.0 g, 4.34 mmol) was dissolved in DCM. 1M BBr$_3$ in DCM (13.01 mL, 13.01 mmol) was added to the reaction mixture dropwise, then was refluxed for 12 h. The reaction mixture was cooled and then was poured into ice water. After stirring for 30 min, the reaction mixture was filtered and the filter cake was rinsed with water and dried to provide the desired compound as a white solid. LC-MS calculated for $C_7H_6ClN_2O_4$ (M+H)$^+$: m/z=217.0; found 216.9.

Step 7: 3-(3-((tert-butyldimethylsilyl)oxy)propoxy)-4-chloro-5-nitrobenzamide

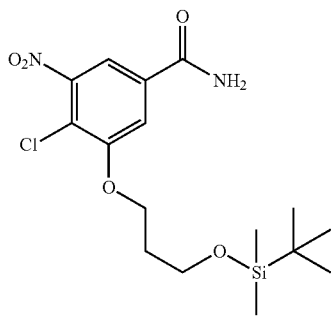 [SMILES: CC(C)(C)[Si](C)(C)OCCCOc1cc(C(N)=O)cc([N+](=O)[O-])c1Cl]

To a suspension of 4-chloro-3-hydroxy-5-nitrobenzamide (211.0 mg, 0.974 mmol), and cesium carbonate (476 mg, 1.461 mmol) in DMF (3247 µL) was added (3-bromopropoxy)(tert-butyl)dimethylsilane (Aldrich, cat #429066: 271 µL, 1.169 mmol). The reaction was then sealed and heated to 50° C. with stirring for 12 h. After cooling with an ice bath, the product was triturated with cold water, filtered, and dried to provide the desired product as a yellow solid. LC-MS calculated for $C_{16}H_{26}ClN_2O_5Si$ (M+H)$^+$: m/z=389.1; found 389.1.

Step 8: (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzofuro[6,7-d]imidazole-5-carboxamide

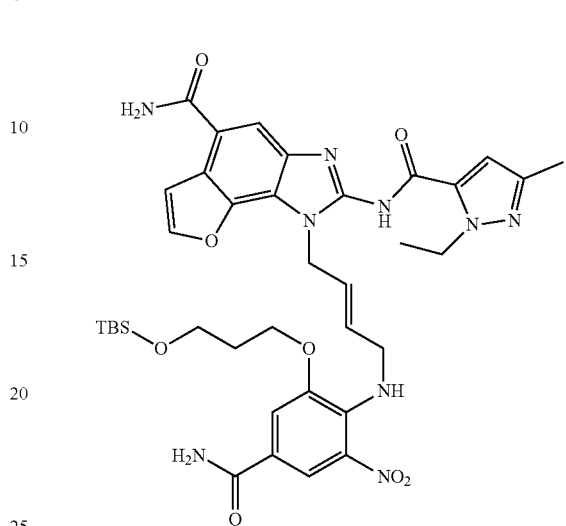

To a solution of 3-(3-((tert-butyldimethylsilyl)oxy)propoxy)-4-chloro-5-nitrobenzamide (0.150 g, 0.386 mmol) in EtOH (1.928 mL) was added DIPEA (0.337 mL, 1.928 mmol) and (E)-1-(4-aminobut-2-en-1-yl)-2-(1-ethyl-3-methyl-1H-pyrazole-5-carboxamido)-1H-benzofuro[6,7-d]imidazole-5-carboxamide, HCl (0.177 g, 0.386 mmol). The mixture was sealed and heated to 120° C. with stirring overnight. Reaction was cooled to rt and concentrated under reduced pressure. The crude product was then purified by column chromatography (15% MeOH/DCM).

LC-MS calculated for $C_{37}H_{48}N_9O_8Si$ (M+H)$^+$: m/z=774.3; found 774.3.

Step 9: (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-1H-benzofuro[6,7-d]imidazole-5-carboxamide

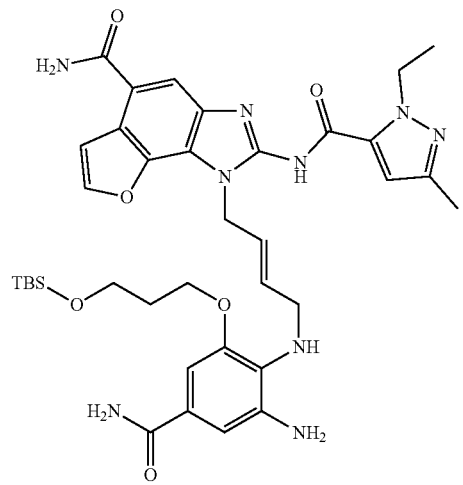

To a solution of (E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzofuro[6,7-d]imidazole-5-carboxamide (0.124 g, 0.160 mmol) in MeOH (3.47 mL) was added sodium hydrosulfite (0.201 g, 1.156 mmol) in water (0.729 mL, 40.5 mmol) and 30% aq. ammonium hydroxide (0.375 mL, 2.89 mmol) at 0° C. The reaction mixture was warmed to room temperature. After 10 min, H₂O was added to the reaction mixture followed by extraction with DCM. The combined organic layers were dried over MgSO₄, filtered, and concentrated under reduced pressure. The resulting crude product was used directly in the next step. LC-MS calculated for $C_{37}H_{50}N_9O_6Si$ (M+H)⁺: m/z=744.4; found 744.6.

Step 10: (E)-1-(4-(2-amino-7-(3-((tert-butyldimethylsilyl)oxy)propoxy)-5-carbamoyl-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide

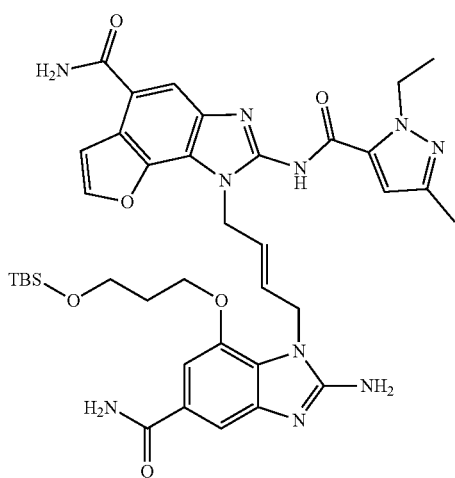

To a solution of (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-1H-benzofuro[6,7-d]imidazole-5-carboxamide (0.124 g, 0.167 mmol) in MeOH (3.47 mL) was added cyanogen bromide (122 mg, 1.156 mmol). The mixture was stirred overnight, then concentrated to dryness. The crude residue was used directly in the next step without further purification. LC-MS calculated for $C_{38}H_{49}N_{10}O_6Si$ (M+H)⁺: m/z=769.4; found 769.6.

Step 11: (E)-1-(4-(7-(3-((tert-butyldimethylsilyl)oxy)propoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide

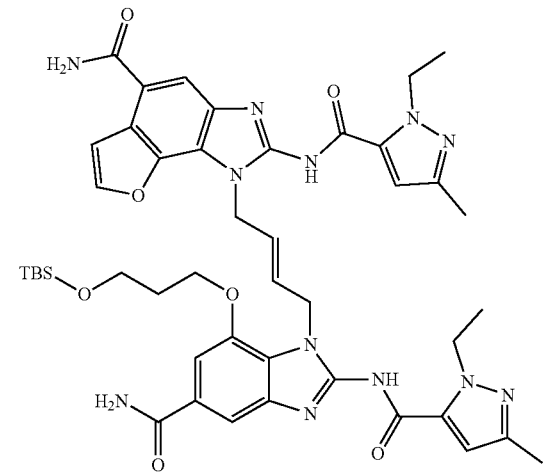

To a solution of (E)-1-(4-(2-amino-7-(3-((tert-butyldimethylsilyl)oxy)propoxy)-5-carbamoyl-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide (0.093 g, 0.121 mmol) in DMF (5 mL) was added DIPEA (0.169 mL, 0.968 mmol), 1-ethyl-3-methyl-1H-pyrazole-5-carboxylic acid (Combi-Blocks, cat #QB-0979: 0.056 g, 0.363 mmol) and BOP (0.160 g, 0.363 mmol). After stirring for 1 h, H₂O was added to the reaction mixture followed by extraction with EtOAc. The combined organic layers were dried over MgSO₄, filtered and concentrated under reduced pressure. The crude product was added to a silica gel column and was eluted with methanol/dichloromethane from 0% to 30%. LC-MS calculated for $C_{45}H_{58}N_{12}O_7Si$ (M+2H)²⁺: m/z=453.2; found 453.4.

Step 12: (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide

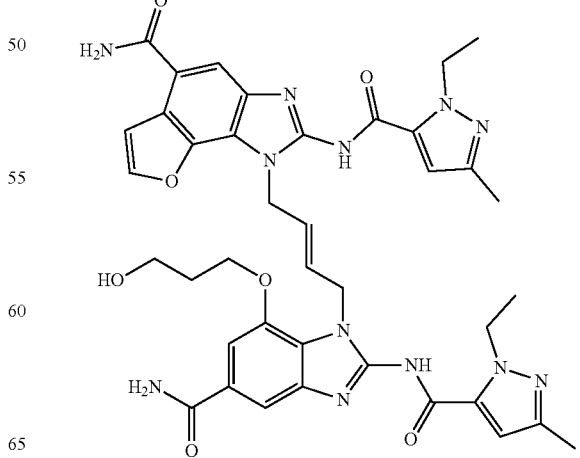

To a solution of (E)-1-(4-(7-(3-((tert-butyldimethylsilyl)oxy)propoxy)-5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide (0.054 g, 0.060 mmol) in THF (0.597 mL) was added 1.0 M TBAF solution in THF (0.239 mF, 0.239 mmol). The mixture was stirred at rt overnight. The reaction was concentrated, then purified by column (MeOH/DCM from 0 to 30%). FC-MS calculated for $C_{39}H_{43}N_{12}O_7$ $(M+H)^+$: m/z=791.3; found 791.3.

Step 13: Ethyl (E)-3-(((3-((5-carbamoyl-1-(4-(5-carbamoyl-2-(1-ethyl-3-methyl-1H-pyrazole-5-carboxamido)-1H-benzofuro[6,7-d]imidazol-1-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoate

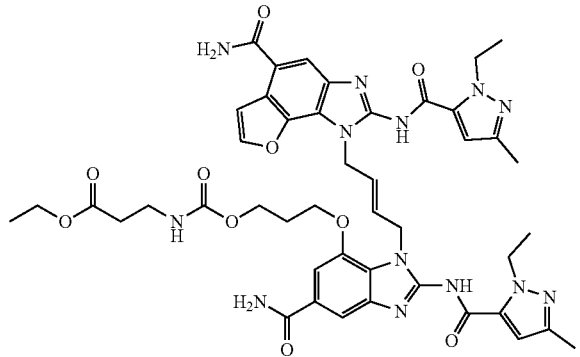 [SMILES: CCOC(=O)CCNC(=O)OCCCOc1cc(C(N)=O)cc2nc(NC(=O)c3cc(C)nn3CC)n(C/C=C/Cn3c(NC(=O)c4cc(C)nn4CC)nc4cc(C(N)=O)c5ccoc5c43)c12]

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-1H-benzofuro[6,7-d]imidazole-5-carboxamide (0.047 g, 0.059 mmol) in THF (0.594 mF) was added DIPEA (0.125 mF, 0.713 mmol) and ethyl 3-isocyanatopropanoate (0.078 mF, 0.594 mmol). The mixture was heated at 70° C. overnight. The reaction was cooled and diluted with water. The reaction was extracted with $CHCl_3/IPA$ (3:1), dried over $MgSO_4$, filtered, and concentrated under reduced pressure. The crude product was purified by column (30% MeOH/DCM). LC-MS calculated for $C_{45}H_{52}N_{13}O_{10}$ $(M+H)^+$: m/z=934.4; found 934.5.

Step 14: (E)-3-(((3-((5-carbamoyl-1-(4-(5-carbamoyl-2-(1-ethyl-3-methyl-1H-pyrazole-5-carboxamido)-1H-benzofuro[6,7-d]imidazol-1-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoic acid Ethyl (E)-3-(((3-((5-carbamoyl-1-(4-(5-carbamoyl-2-(1-ethyl-3-methyl-1H-pyrazole-5-carboxamido)-1H-benzofuro[6,7-d]imidazol-1-yl)but-2-en-1-yl)-2-(1-ethyl-3-methyl-1H-pyrazole-5-carboxamido)-1H-benzo[d]imidazol-7-yl)oxy)propoxy)carbonyl)amino)propanoate (0.040 g, 0.0428 mmol) was dissolved in THF (0.6 mL) and MeOH (0.3 mL). To this was added 2 M LiOH (0.297 mL, 0.594 mmol). The reaction was stirred for 15 min, and was then dissolved in MeOH and purified by prep HPLC (pH=2, MeCN/water+ TFA) to provide the desired compound as the TFA salt. LC-MS calculated for $C_{43}H_{48}N_{13}O_{10}$ $(M+H)^+$: m/z=906.4; found 906.0.

Example A. IRF3 and NF-kB Activation Assays

THP-1 Dual Cells (Invivogen) were maintained in RPMI1640 medium with addition of 10% FBS, 100 μg/mL zeocin, 10 μg/mL blasticidin. Cells were added in a 96-well flat bottom assay plate at 100,000 per well in 100 μL complete RPMI medium. Test compounds were prepared by serial dilution in complete RPMI medium and 100 μL test compounds were transferred to each corresponding well. The assay plate was incubated at 37° C. 5% $CO_2$ for 24 hours. After the overnight incubation, 20 μL of the culture supernatants were collected, followed by addition of 180 μL of QUANTI-Blue (Invivogen) to assess IRF3 activity. The amount of IRF3 activation was assessed by reading the absorbance at 620-655 nm with a microplate reader 2 hours later. The culture supernatant from the untreated THP-1 cells was used as the negative control. To determine the NF-κB activation, another 20 μL of culture supernatant were transferred to a 96-well white plate, followed by addition of 50 μL of Quanti-Luc™ assay solution (Invivogen). The amount of NF-κB activation induced by the test compounds were determined by the luminescence above the untreated control. $EC_{50}$ determination was performed by fitting the curve of percent control activity versus the log of the compound concentration using the GraphPad Prism 6.0 software.

$EC_{50}$ in activating IRF3 for the compounds of the Examples are presented in Table 1.

TABLE 1

| Example No. | THP1 IRF3 $EC_{50}$ (nM) |
| --- | --- |
| 1 | +++ |
| 2 | + |
| 3 | + |

+ means <100 nM

++ means 100 nM to 500 nM

+++ means >500 nM to 1000 nM

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a STING-mediated disease or disorder selected from the group consisting of bladder cancer, head and neck cancer, uterine cancer (UC), prostate cancer, lung cancer, melanoma, colorectal cancer, salivary gland cancer, skin cancer, breast cancer, ovarian cancer, lymphoma, pancreatic cancer, and oral cancer, comprising administering a therapeutically effective amount of a compound of Formula (III):

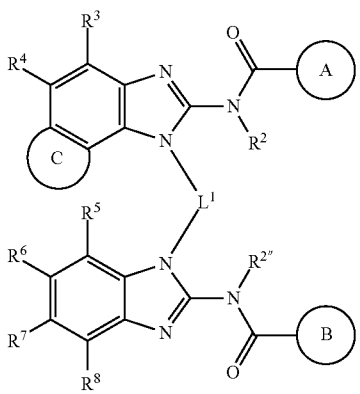

(III)

or a pharmaceutically acceptable salt thereof, wherein:
$R^2$ is selected from H, $C_{1-4}$ alkyl, and $C_{1-4}$ haloalkyl;
$R^{2''}$ is selected from H, $C_{1-4}$ alkyl, and $C_{1-4}$ haloalkyl;
$R^3$ and $R^4$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)OR^{b3}$, $NR^{c3}C(=O)NR^{c3}R^{d3}$, $C(=NR^e)R^{b3}$, $C(=NR^e)NR^{c3}R^{d3}$, $NR^{c3}C(=NR^e)NR^{c3}R^{d3}$, $NHOR^{a3}$, $NR^{c3}S(=O)R^{b3}$, $NR^{c3}S(=O)NR^{c3}R^{d3}$, $S(=O)R^{b3}$, $S(=O)NR^{c3}R^{d3}$, $S(=O)_2R^{b3}$, $NR^{c3}S(=O)_2R^{b3}$, $NR^{c3}S(=O)_2NR^{c3}R^{d3}$, $S(=O)_2R^{b3}$, and $S(=O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{3A}$ substituents;
each $R^{a3}$, $R^{c3}$, and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{3A}$ substituents;
each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{3A}$ substituents;
each $R^e$ is independently selected from H, CN, OH, $C_{1-4}$ alkyl, and $C_{1-4}$ alkoxy;
each $R^{3A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a31}$, $SR^{a31}$, $C(=O)R^{b31}$, $C(=O)NR^{c31}R^{d31}$, $C(=O)OR^{a31}$, $OC(=O)R^{b31}$, $OC(=O)NR^{c31}R^{d31}$, $NR^{c31}R^{d31}$, $NR^{c31}C(=O)R^{b31}$, $NR^{c31}C(=O)OR^{b31}$, $NR^{c31}C(=O)NR^{c31}R^{d31}$, $C(=NR^e)R^{b31}$, $C(=NR^e)NR^{c31}R^{d31}$, $NR^{c31}C(=NR^e)NR^{c31}R^{d31}$, $NHOR^{a31}$, $NR^{c31}S(=O)R^{b31}$, $NR^{c31}S(=O)NR^{c31}R^{d31}$, $S(=O)R^{b31}$, $S(=O)NR^{c31}R^{d31}$, $NR^{c31}S(=O)_2R^{b31}$, $NR^{c31}S(=O)_2NR^{c31}R^{d31}$, $S(=O)_2R^{b31}$, and $S(=O)_2NR^{c31}R^{d31}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{3B}$ substituents;
each $R^{a31}$, $R^{c31}$, and $R^{d31}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{3B}$ substituents;
each $R^{b31}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{3B}$ substituents;
each $R^{3B}$ is independently selected from H, halo, CN, OH, $NO_2$, COOH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, and $C_{1-6}$ alkoxycarbonyl;
Ring C is selected from a phenyl ring, a 5-6 membered heteroaryl ring, a $C_{5-7}$ cycloalkyl ring, and a 5-14 membered heterocycloalkyl ring, which is optionally substituted with 1, 2, 3, 4, or 5 independently selected $R^C$ substituents;
each $R^C$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aC}$, $SR^{aC}$, $C(=O)R^{bC}$, $C(=O)NR^{cC}R^{dC}$, $C(=O)OR^{aC}$, $OC(=O)R^{bC}$, $OC(=O)NR^{cC}R^{dC}$, $NR^{cC}R^{dC}$, $NR^{cC}C(=O)R^{bC}$, $NR^{cC}C(=O)OR^{bC}$, $NR^{cC}C(=O)NR^{cC}R^{dC}$, $C(=NR^e)R^{bC}$, $C(=NR^e)NR^{cC}R^{dC}$, $NR^{cC}C(=NR^e)NR^{cC}R^{dC}$, $NHOR^{aC}$, $NR^{cC}S(=O)R^{bC}$, $NR^{cC}S(=O)NR^{cC}R^{dC}$, $S(=O)R^{bC}$, $S(=O)NR^{cC}R^{dC}$, $NR^{cC}S(=O)_2R^{bC}$, $NR^{cC}S(=O)_2NR^{cC}R^{dC}$, $S(=O)_2R^{bC}$, and $S(=O)_2NR^{cC}R^{dC}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{C1}$ substituents;

each $R^{aC}$, $R^{cC}$, and $R^{dC}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{C1}$ substituents;

each $R^{bC}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{C1}$ substituents;

each $R^{C1}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aC1}$, $SR^{aC1}$, $C(=O)R^{bC1}$, $C(=O)NR^{cC1}R^{dC1}$, $C(=O)OR^{aC1}$, $OC(=O)R^{bC1}$, $OC(=O)NR^{cC1}R^{dC1}$, $NR^{cC1}R^{dC1}$, $NR^{cC1}C(=O)R^{bC1}$, $NR^{cC1}C(=O)OR^{bC1}$, $NR^{cC1}C(=O)NR^{cC1}R^{dC1}$, $C(=NR^e)R^{bC1}$, $C(=NR^e)NR^{cC1}R^{dC1}$, $NR^{cC1}C(=NR^e)NR^{cC1}R^{dC1}$, $NHOR^{aC1}$, $NR^{cC1}S(=O)R^{bC1}$, $NR^{cC1}S(=O)NR^{cC1}R^{dC1}$, $S(=O)R^{bC1}$, $S(=O)NR^{cC1}R^{dC1}$, $NR^{cC1}S(=O)_2R^{bC1}$, $NR^{cC1}S(=O)_2NR^{cC1}R^{dC1}$, $S(=O)_2R^{bC1}$, and $S(=O)_2NR^{cC1}R^{dC1}$, wherein said $C_{1-6}$ alkyl, $C_{2-6}$ alkenyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C2}$ substituents;

each $R^{aC1}$, $R^{cC1}$, and $R^{dC1}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C2}$ substituents;

each $R^{bC1}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{C2}$ substituents;

each $R^{C2}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{aC2}$, $SR^{aC2}$, $C(=O)R^{bC2}$, $C(=O)NR^{cC2}R^{dC2}$, $C(=O)OR^{aC2}$, $OC(=O)R^{bC2}$, $OC(=O)NR^{cC2}R^{dC2}$, $NR^{cC2}R^{dC2}$, $NR^{cC2}C(=O)R^{bC2}$, $NR^{cC2}C(=O)OR^{bC2}$, $NR^{cC2}C(=O)NR^{cC2}R^{dC2}$, $C(=NR^e)R^{bC2}$, $C(=NR^e)NR^{cC2}R^{dC2}$, $NR^{cC2}C(=NR^e)NR^{cC2}R^{dC2}$, $NHOR^{aC2}$, $NR^{cC2}S(=O)R^{bC2}$, $NR^{cC2}S(=O)NR^{cC2}R^{dC2}$, $S(=O)R^{bC2}$, $S(=O)NR^{cC2}R^{dC2}$, $NR^{cC2}S(=O)_2R^{bC2}$, $NR^{cC2}S(=O)_2NR^{cC2}R^{dC2}$, $S(=O)_2R^{bC2}$, and $S(=O)_2NR^{cC2}R^{dC2}$, wherein said $C_{1-6}$ alkyl, $C_{2-6}$ alkenyl, $C_{2-6}$ alkynyl, $C_{1-6}$ haloalkyl $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{aC2}$, $R^{cC2}$, and $R^{dC2}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

each $R^{bC2}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^S$ substituents;

$R^5$, $R^6$, $R^7$, and $R^8$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^e)R^{b5}$, $C(=NR^e)NR^{c5}R^{d5}$, $NR^{c5}C(=NR^e)NR^{c5}R^{d5}$, $NHOR^{a5}$, $NR^{c5}S(=O)R^{b5}$, $NR^{c5}S(=O)NR^{c5}R^{d5}$, $S(=O)R^{b5}$, $S(=O)NR^{c5}R^{d5}$, $NR^{c5}S(=O)_2R^{b5}$, $NR^{c5}S(=O)_2NR^{c5}R^{d5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

each $R^{a5}$, $R^{c5}$, and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

each $R^{b5}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{5A}$ substituents;

each $R^{5A}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a51}$, $SR^{a51}$, $C(=O)R^{b51}$, $C(=O)NR^{c51}R^{d51}$, $C(=O)OR^{a51}$, $OC(=O)R^{b51}$, $OC(=O)NR^{c51}R^{d51}$, $NR^{c51}R^{d51}$, $NR^{c51}C(=O)R^{b51}$, $NR^{c51}C(=O)OR^{b51}$, $NR^{c51}C(=O)NR^{c51}R^{d51}$, $C(=NR^e)R^{b51}$, $C(=NR^e)NR^{c51}R^{d51}$, $NR^{c51}C(=NR^e)NR^{c51}R^{d51}$, $NHOR^{a51}$, $NR^{c51}S(=O)R^{b51}$, $NR^{c51}S(=O)NR^{c51}R^{d51}$, $S(=O)R^{b51}$, $S(=O)NR^{c51}R^{d51}$, $NR^{c51}S(=O)_2R^{b51}$, $NR^{c51}S(=O)_2NR^{c51}R^{d51}$, $S(=O)_2R^{b51}$, and $S(=O)_2NR^{c51}R^{d51}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, are each optionally substituted with 1, 2, 3, or 4 independently selected $R^{5B}$ substituents;

each $R^{a51}$, $R^{c51}$ and $R^{d51}$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{b51}$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{5B}$ substituents;

each $R^{5B}$ is independently selected from H, halo, CN, OH, $NO_2$, COOH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, and $C_{1-6}$ alkoxycarbonyl;

Ring moiety A is selected from $C_{3-10}$ cycloalkyl, $C_{6-10}$ aryl, 4-10 membered heterocycloalkyl, and 5-10 membered heteroaryl, each of which is optionally substituted with 1, 2, 3, 4, or 5 independently selected $R^A$ substituents;

Ring moiety B is selected from $C_{3-10}$ cycloalkyl, $C_{6-10}$ aryl, 4-10 membered heterocycloalkyl, and 5-10 membered heteroaryl, each of which is optionally substituted with 1, 2, 3, 4, or 5 independently selected $R^B$ substituents;

each $R^A$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aA}$, $SR^{aA}$, $C(=O)R^{bA}$, $C(=O)NR^{cA}R^{dA}$, $C(=O)OR^{aA}$, $OC(=O)R^{bA}$, $OC(=O)NR^{cA}R^{dA}$, $NR^{cA}R^{dA}$, $NR^{cA}C(=O)R^{bA}$, $NR^{cA}C(=O)OR^{bA}$, $NR^{cA}C(=O)NR^{cA}R^{dA}$, $C(=NR^e)R^{bA}$, $C(=NR^e)NR^{cA}R^{dA}$, $NR^{cA}C(=NR^e)NR^{cA}R^{dA}$, $NHOR^{aA}$, $NR^{cA}S(=O)R^{bA}$, $NR^{cA}S(=O)NR^{cA}R^{dA}$, $S(=O)R^{bA}$, $S(=O)NR^{cA}R^{dA}$, $NR^{cA}S(=O)_2R^{bA}$, $NR^{cA}S(=O)_2NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9A}$ substituents;

each $R^B$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $OR^{aB}$, $SR^{aB}$, $C(=O)R^{bB}$, $C(=O)NR^{cB}R^{dB}$, $C(=O)OR^{aB}$, $OC(=O)R^{bB}$, $OC(=O)NR^{cB}R^{dB}$, $NR^{cB}R^{dB}$, $NR^{cB}C(=O)R^{bB}$, $NR^{cB}C(=O)OR^{bB}$, $NR^{cB}C(=O)NR^{cB}R^{dB}$, $C(=NR^e)R^{bB}$, $C(=NR^e)NR^{cB}R^{dB}$, $NR^{cB}C(=NR^e)NR^{cB}R^{dB}$, $NHOR^{aB}$, $NR^{cB}S(=O)R^{bB}$, $NR^{cB}S(=O)NR^{cB}R^{dB}$, $S(=O)R^{bB}$, $S(=O)NR^{cB}R^{dB}$, $NR^{cB}S(=O)_2R^{bB}$, $NR^{cB}S(=O)_2NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9B}$ substituents;

provided that when $R^A$ is attached to a nitrogen atom of the ring moiety A, then $R^A$ is selected from H, CN, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $C(=O)R^{bA}$, $C(=O)NR^{cA}R^{dA}$, $C(=O)OR^{aA}$, $C(=NR^e)R^{bA}$, $C(=NR^e)NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9A}$ substituents;

provided that when $R^B$ is attached to a nitrogen atom of the ring moiety B, then $R^B$ is selected from H, CN, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, 5-10 membered heteroaryl-$C_{1-4}$ alkyl, $C(=O)R^{bB}$, $C(=O)NR^{cB}R^{dB}$, $C(=O)OR^{aB}$, $C(=NR^e)R^{bB}$, $C(=NR^e)NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, 4, or 5 independently selected $R^{9B}$ substituents;

each $R^{aA}$, $R^{cA}$, and $R^{dA}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

each $R^{bA}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9A}$ substituents;

each $R^{aB}$, $R^{cB}$, and $R^{dB}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9B}$ substituents;

each $R^{bB}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, $C_{3-10}$ cycloalkyl-$C_{1-4}$ alkyl, $C_{6-10}$ aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{9B}$ substituents;

each $R^{9A}$ and $R^{9B}$ is independently selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a9}$, $SR^{a9}$, $C(=O)R^{b9}$, $C(=O)NR^{c9}R^{d9}$, $C(=O)OR^{a9}$, $OC(=O)R^{b9}$, $OC(=O)NR^{c9}R^{d9}$, $NR^{c9}R^{d9}$, $NR^{c9}C(=O)R^{b9}$, $NR^{c9}C(=O)OR^{b9}$, $NR^{c9}C$ (=O)NR$^{c9}$R$^{d9}$, C(=NR$^e$)R$^{b9}$, C(=NR$^e$)NR$^{c9}$R$^{d9}$, NR$^{c9}$C(=NR$^e$)NR$^{c9}$R$^{d9}$, NHOR$^{a9}$, NR$^{c9}$S(=O)R$^{b9}$, NR$^{c9}$S(=O)NR$^{c9}$R$^{d9}$, S(=O)R$^{b9}$, S(=O)NR$^{c9}$R$^{d9}$, NR$^{c9}$S(=O)$_2$R$^{b9}$, NR$^{c9}$S(=O)$_2$NR$^{c9}$R$^{d9}$, S(=O)$_2$R$^{b9}$, and S(=O)$_2$NR$^{c9}$R$^{d9}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^S$ substituents;

each R$^{a9}$, R$^{c9}$, and R$^{d9}$ is independently selected from H, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^S$ substituents;

each R$^{b9}$ is independently selected from C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^S$ substituents;

L$^1$ is selected from —R—R—, —R—R—R—, -Cy-, —R-Cy-, -Cy-R—, —R-Cy-R—, —R—R-Cy-, -Cy-R—R—, and -Cy-R-Cy-;

each R is independently selected from M, C$_{1-6}$ alkylene, C$_{2-6}$ alkenylene, C$_{2-6}$ alkynylene, C$_{1-6}$ alkylene-M, M-C$_{1-6}$ alkylene, C$_{1-6}$ alkylene-M-C$_{1-6}$ alkylene, M-C$_{1-6}$ alkylene-M, C$_{2-6}$ alkenylene-M, M-C$_{2-6}$ alkenylene, C$_{2-6}$ alkenylene-M-C$_{2-6}$ alkenylene, M-C$_{2-6}$ alkenylene-M, C$_{2-6}$ alkynylene-M, M-C$_{2-6}$ alkynylene, C$_{2-6}$ alkynylene-M-C$_{2-6}$ alkynylene, and M-C$_{2-6}$ alkynylene-M, wherein each of said C$_{1-6}$ alkylene, C$_{2-6}$ alkenylene, and C$_{2-6}$ alkynylene is optionally substituted with 1, 2, 3, or 4 substituents independently selected R$^S$ substituents;

each Cy is independently selected from C$_{3-14}$ cycloalkyl, phenyl, 4-14 membered heterocycloalkyl, and 5-6 membered heteroaryl, each of which is optionally substituted with 1, 2, 3, or 4 independently selected R$^S$ substituents;

each M is independently selected from —O—, —S—, —C(O)—, —C(O)NR$^L$—, —C(O)O—, —OC(O)—, —OC(O)NR$^L$—, —NR$^L$—, —NR$^L$C(O)—, —NR$^L$C(O)O—, —NR$^L$C(O)NR$^L$—, —NR$^L$S(O)$_2$—, —S(O)$_2$—, —S(O)$_2$NR$^L$—, and —NR$^L$S(O)$_2$NR$^L$—; provided that when M is attached to a nitrogen atom, then M is selected from —C(O)—, —C(O)NR$^L$—, —C(O)O—, —S(O)$_2$—, and —S(O)$_2$NR$^L$—;

each R$^L$ is independently selected from H, C$_{1-3}$ alkyl, C$_{2-3}$ alkenyl, C$_{2-3}$ alkynyl, and C$_{1-3}$ haloalkyl; and each R$^S$ is independently selected from OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-3}$ alkoxycarbonyl, C$_{1-3}$ alkylcarbonyloxy, C$_{1-3}$ alkylcarbonylamino, C$_{1-3}$ alkoxycarbonylamino, C$_{1-3}$ alkylaminocarbonyloxy, C$_{1-3}$ alkylsulfonylamino, aminosulfonyl, C$_{1-3}$ alkylaminosulfonyl, alkyl)aminosulfonyl, aminosulfonylamino, C$_{1-3}$ alkylaminosulfonylamino, alkyl)aminosulfonylamino, aminocarbonylamino, C$_{1-3}$ alkylaminocarbonylamino, and di(C$_{1-3}$ alkyl)aminocarbonylamino.

2. The method of claim 1, wherein R$^2$ is H.

3. The method of claim 1, wherein R$^{2''}$ is H.

4. The method of claim 1, wherein R$^3$ and R$^4$ are each independently selected from H, D, halo, CN, NO$_2$, C$_{1-6}$ alkyl, C$_{2-6}$ alkenyl, C$_{2-6}$ alkynyl, C$_{1-6}$ haloalkyl, OR$^{a3}$, C(=O)R$^{b3}$, C(=O)NR$^{c3}$R$^{d3}$, C(=O)OR$^{a3}$, NR$^{c3}$R$^{d3}$, NR$^{c3}$C(=O)R$^{b3}$, NR$^{c3}$C(=O)OR$^{b3}$, S(=O)$_2$R$^{b3}$, and S(=O)$_2$NR$^{c3}$R$^{d3}$, wherein said C$_{1-6}$ alkyl, C$_{2-6}$ alkenyl, C$_{2-6}$ alkynyl, and C$_{1-6}$ haloalkyl are each optionally substituted with 1, 2, 3, or 4 independently selected R$^{3A}$ substituents.

5. The method of claim 1, wherein each R$^{a3}$, R$^{c3}$, and R$^{d3}$ is independently selected from H, C$_{1-6}$ alkyl, and C$_{1-6}$ haloalkyl, wherein said C$_{1-6}$ alkyl and C$_{1-6}$ haloalkyl are each optionally substituted with 1, 2, 3, or 4 independently selected R$^{3A}$ substituents;

each R$^{b3}$ is independently selected from C$_{1-6}$ alkyl and C$_{1-6}$ haloalkyl, each of which are optionally substituted with 1, 2, 3, or 4 independently selected R$^{3A}$ substituents; and each R$^{3A}$ is independently selected from H, halo, CN, OH, NO$_2$, C$_{1-6}$ alkyl, C$_{2-6}$ alkenyl, C$_{2-6}$ alkynyl, haloalkyl, cyano-C$_{1-6}$ alkyl, HO—C$_{1-6}$ alkyl, C$_{1-6}$ alkoxy-C$_{1-6}$ alkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonyloxy, C$_{1-6}$ alkylcarbonylamino, C$_{1-6}$ alkoxycarbonylamino, C$_{1-6}$ alkylaminocarbonyloxy, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

6. The method of claim 1, wherein Ring C is a moiety selected from:

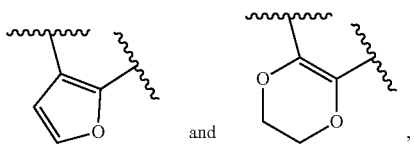 [SMILES: *c1ccoc1* ; *C1=C(*)OCCO1]

each which is optionally substituted with 1 or 2 independently selected R$^C$ substituents.

7. The method of claim 1, wherein Ring C is

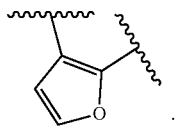 [SMILES: *c1ccoc1*]

8. The method of claim 1, wherein Ring C is

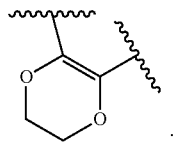 [SMILES: *C1=C(*)OCCO1]

9. The method of claim 1, wherein Ring moiety A is a pyrazole ring, which is optionally substituted with 1, 2, or 3 independently selected $R^A$ substituents.

10. The method of claim 1, wherein each $R^A$ is independently selected from H and $C_{1-6}$ alkyl.

11. The method of claim 1, wherein Ring moiety B is a pyrazole ring, which is optionally substituted with 1, 2, or 3 independently selected $R^B$ substituents.

12. The method of claim 1, wherein each $R^B$ is independently selected from H and $C_{1-6}$ alkyl.

13. The method of claim 1, wherein $L^1$ is —$CH_2$—CH=CH—$CH_2$—.

14. The method of claim 1, wherein:
$R^2$ is H;
$R^{2''}$ is H;
$R^3$ and $R^4$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a3}$, $SR^{a3}$, $C(=O)R^{b3}$, $C(=O)NR^{c3}R^{d3}$, $C(=O)OR^{a3}$, $OC(=O)R^{b3}$, $OC(=O)NR^{c3}R^{d3}$, $NR^{c3}R^{d3}$, $NR^{c3}C(=O)R^{b3}$, $NR^{c3}C(=O)OR^{b3}$, $NR^{c3}C(=O)NR^{c3}R^{d3}$, $C(=NR^e)R^{b3}$, $C(=NR^e)NR^{c3}R^{d3}$, $NR^{c3}C(=NR^e)NR^{c3}R^{d3}$, $NR^{c3}S(=O)_2R^{b3}$, $NR^{c3}S(=O)_2NR^{c3}R^{d3}$, $S(=O)_2R^{b3}$, and $S(=O)_2NR^{c3}R^{d3}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{3A}$ substituents;
each $R^{a3}$, $R^{c3}$, and $R^{d3}$ is independently selected from H, $C_{1-6}$ alkyl and $C_{1-6}$ haloalkyl, wherein said $C_{1-6}$ alkyl and $C_{1-6}$ haloalkyl are each optionally substituted with 1, 2, 3, or 4 independently selected $R^{3A}$ substituents;
each $R^{b3}$ is independently selected from H, $C_{1-6}$ alkyl and $C_{1-6}$ haloalkyl, each of which is optionally substituted with 1, 2, 3, or 4 independently selected $R^{3A}$ substituents;
each $R^e$ is independently selected from H, CN, OH, $C_{1-4}$ alkyl, and $C_{1-4}$ alkoxy;
each $R^{3A}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylamino sulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring C is a 5-membered heteroaryl ring or a 6-membered heterocycloalkyl ring, each of which is optionally substituted with 1, 2, 3, or 4 independently selected $R^C$ substituents;
each $R^C$ is independently selected from H, D, halo, CN, $C_{1-6}$ alkyl, $C_{2-6}$ alkenyl, $C_{2-6}$ alkynyl, $C_{1-6}$ haloalkyl, $OR^{aC}$, $SR^{aC}$, $C(=O)R^{bC}$, $C(=O)NR^{cC}R^{dC}$, $C(=O)OR^{aC}$, $OC(=O)R^{bC}$, $OC(=O)NR^{cC}R^{dC}$, $NR^{cC}R^{dC}$, $NR^{cC}C(=O)R^{bC}$, $NR^{cC}C(=O)OR^{bC}$, $NR^{cC}C(=O)NR^{cC}R^{dC}$, $C(=NR^e)R^{bC}$, $C(=NR^e)NR^{cC}R^{dC}$, $NR^{cC}C(=NR^e)NR^{cC}R^{dC}$, $NR^{cC}S(=O)_2R^{bC}$, $NR^{cC}S(=O)_2NR^{cC}R^{dC}$, $S(=O)_2R^{bC}$, and $S(=O)_2NR^{cC}R^{dC}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{C1}$ substituents;
each $R^{aC}$, $R^{cC}$, and $R^{dC}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{C1}$ substituents;
each $R^{bC}$ is independently selected from $C_{1-6}$ alkyl and $C_{1-6}$ haloalkyl, wherein said $C_{1-6}$ alkyl and $C_{1-6}$ haloalkyl are each optionally substituted with 1, 2, or 3 independently selected $R^{C1}$ substituents;
each $R^{C1}$ is independently selected from H, D, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;
$R^5$, $R^6$, $R^7$, and $R^8$ are each independently selected from $R^5$ and $R^6$ are each independently selected from H, D, halo, CN, $NO_2$, $C_{1-6}$ alkyl, $C_{2-6}$ alkenyl, $C_{2-6}$ alkynyl, $C_{1-6}$ haloalkyl, $OR^{a5}$, $SR^{a5}$, $C(=O)R^{b5}$, $C(=O)NR^{c5}R^{d5}$, $C(=O)OR^{a5}$, $OC(=O)R^{b5}$, $OC(=O)NR^{c5}R^{d5}$, $NR^{c5}R^{d5}$, $NR^{c5}C(=O)R^{b5}$, $NR^{c5}C(=O)OR^{b5}$, $NR^{c5}C(=O)NR^{c5}R^{d5}$, $C(=NR^e)R^{b5}$, $C(=NR^e)NR^{c5}R^{d5}$, $NR^{c5}C(=NR^e)NR^{c5}R^{d5}$, $NR^{c5}S(=O)_2R^{b5}$, $NR^{c5}S(=O)_2NR^{c5}R^{d5}$, $S(=O)_2R^{b5}$, and $S(=O)_2NR^{c5}R^{d5}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{5A}$ substituents;
each $R^{a5}$, $R^{c5}$, and $R^{d5}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{5A}$ substituents;
each $R^{b5}$ is independently selected from $C_{1-6}$ alkyl and $C_{1-6}$ haloalkyl, each of which is optionally substituted with 1, 2, 3, or 4 independently selected $R^{5A}$ substituents;
each $R^{5A}$ is independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring moiety A is a 5-6 membered heteroaryl ring, which is optionally substituted with 1, 2, 3, 4, or 5 independently selected $R^A$ substituents;

Ring moiety B is a 5-6 membered heteroaryl ring, which is optionally substituted with 1, 2, 3, 4, or 5 independently selected $R^B$ substituents;

each $R^A$ is independently selected from halo, CN, $NO_2$, $C_{1-6}$ alkyl, $C_{2-6}$ alkenyl, $C_{2-6}$ alkynyl, $C_{1-6}$ haloalkyl, $OR^{aA}$ $C(=O)R^{bA}$, $C(=O)NR^{cA}R^{dA}$, $C(=O)OR^{aA}$, $OC(=O)R^{bA}$, $OC(=O)NR^{cA}R^{dA}$, $NR^{cA}R^{dA}$, $NR^{cA}C(=O)R^{bA}$, $NR^{cA}C(=O)OR^{bA}$, $NR^{cA}C(=O)NR^{cA}R^{dA}$, $NR^{cA}S(=O)_2R^{bA}$, $NR^{cA}S(=O)_2NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, and $C_{1-6}$ haloalkyl are each optionally substituted with 1, 2, or 4 independently selected $R^{9A}$ substituents;

provided that when $R^A$ is attached to a nitrogen atom of ring moiety A, then each $R^A$ is independently selected from H, CN, $C_{1-6}$ alkyl, $C_{2-6}$ alkenyl, $C_{2-6}$ alkynyl, $C_{1-6}$ haloalkyl, $C(=O)R^{bA}$, $C(=O)NR^{cA}R^{dA}$, $C(=O)OR^{aA}$, $C(=NR^e)R^{bA}$, $C(=NR^e)NR^{cA}R^{dA}$, $S(=O)_2R^{bA}$, and $S(=O)_2NR^{cA}R^{dA}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9A}$ substituents;

$R^{aA}$, $R^{cA}$, and $R^{dA}$ is independently selected from H, $C_{1-6}$ alkyl, and $C_{1-6}$ haloalkyl; wherein said $C_{1-6}$ alkyl and $C_{1-6}$ haloalkyl are each optionally substituted with 1, 2, 3, or 4 independently selected $R^{9A}$ substituents;

each $R^{bA}$ is independently selected from $C_{1-6}$ alkyl and $C_{1-6}$ haloalkyl; wherein said $C_{1-6}$ alkyl and $C_{1-6}$ haloalkyl are each optionally substituted with 1, 2, 3, or 4 independently selected $R^{9A}$ substituents;

each $R^{9A}$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;

each $R^B$ is independently selected from H, halo, CN, $NO_2$, $C_{1-6}$ alkyl, $C_{2-6}$ alkenyl, $C_{2-6}$ alkynyl, $C_{1-6}$ haloalkyl, $OR^{aB}$, $C(=O)R^{bB}$, $C(=O)NR^{cB}R^{dB}$, $C(=O)OR^{aB}$, $OC(=O)R^{bB}$, $OC(=O)NR^{cB}R^{dB}$, $NR^{cB}R^{dB}$, $NR^{cB}C(=O)R^{bB}$, $NR^{cB}C(=O)OR^{bB}$, $NR^{cB}C(=O)NR^{cB}R^{dB}$, $NR^{cB}S(=O)_2R^{bB}$, $NR^{cB}S(=O)_2NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9B}$ substituents;

provided that when $R^B$ is attached to a nitrogen atom of ring moiety B, then each $R^B$ is independently selected from H, CN, $C_{1-6}$ alkyl, $C_{2-6}$ alkenyl, $C_{2-6}$ alkynyl, $C_{1-6}$ haloalkyl, $C(=O)R^{bB}$, $C(=O)NR^{cB}R^{dB}$, $C(=O)OR^{aB}$, $C(=NR^e)R^{bB}$, $C(=NR^e)NR^{cB}R^{dB}$, $S(=O)_2R^{bB}$, and $S(=O)_2NR^{cB}R^{dB}$, wherein said $C_{1-6}$ alkyl, $C_{2-6}$ alkenyl, $C_{2-6}$ alkynyl, and $C_{1-6}$ haloalkyl are each optionally substituted with 1, 2, 3, or 4 independently selected $R^{9B}$ substituents;

each $R^{aB}$, $R^{cB}$, and $R^{dB}$ is independently selected from H, $C_{1-6}$ alkyl, and $C_{1-6}$ haloalkyl; wherein said $C_{1-6}$ alkyl and $C_{1-6}$ haloalkyl are each optionally substituted with 1, 2, 3, or 4 independently selected $R^{9B}$ substituents;

each $R^{bB}$ is independently selected from $C_{1-6}$ alkyl and $C_{1-6}$ haloalkyl; wherein said $C_{1-6}$ alkyl and $C_{1-6}$ haloalkyl are each optionally substituted with 1, 2, 3, or 4 independently selected $R^{9B}$ substituents;

each $R^{9B}$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;

$L^1$ is selected from —R—R— and —R—R—R—;

each R is independently selected from M, $C_{1-6}$ alkylene, $C_{2-6}$ alkenylene, and $C_{2-6}$ alkynylene;

each M is independently selected from —O—, —C(O)—, —C(O)$NR^L$—, —OC(O)$NR^L$—, —$NR^L$—, —$NR^L$C(O)—, —$NR^L$C(O)O—, —$NR^L$S(O)$_2$—, —S(O)$_2$—, and —S(O)$_2NR^L$—, provided that when M is attached to a nitrogen atom, then M is selected from —C(O)—, —C(O)$NR^L$—, —C(O)O—, —S(O)$_2$—, and —S(O)$_2NR^L$—; and each $R^L$ is independently selected from H and $C_{1-3}$ alkyl.

15. The method of claim 1, wherein:

$R^2$ is H;

$R^{2''}$ is H;

$R^3$ and $R^4$ are each independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring C is a 5-membered heteroaryl ring or a 6-membered heterocycloalkyl ring, wherein the heteroaryl ring or heterocycloalkyl ring contains 1 or 2 oxygen ring members, wherein said 5-membered heteroaryl ring or a 6-membered heterocycloalkyl ring are each optionally substituted with 1 or 2 independently selected $R^C$ substituents;

each $R^C$ is independently selected from H, D, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^5$, $R^6$, $R^7$, and $R^8$ are each independently selected H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)

amino, thio, $C_{1-6}$ alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring moiety A is a 5-membered heteroaryl ring, which is optionally substituted with 1, 2, or 3 independently selected $R^A$ substituents;

Ring moiety B is a 5-membered heteroaryl ring, which is optionally substituted with 1, 2, or 3 independently selected $R^B$ substituents;

each $R^A$ is independently selected from H, $C_{1-6}$ alkyl, $C_{2-6}$ alkenyl, $C_{2-6}$ alkynyl, CN, and $C_{1-6}$ haloalkyl;

each $R^B$ is independently selected from H, $C_{1-6}$ alkyl, $C_{2-6}$ alkenyl, $C_{2-6}$ alkynyl, CN, and $C_{1-6}$ haloalkyl;

$L^1$ is selected from —R—R— and —R—R—R—; and each R is independently selected from $C_{1-6}$ alkylene, $C_{2-6}$ alkenylene, and $C_{2-6}$ alkynylene.

16. The method of claim 1, wherein:

$R^2$ is H;

$R^{2''}$ is H;

$R^3$ and $R^4$ are each independently selected from H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring C is a 5-membered heteroaryl ring or a 6-membered heterocycloalkyl ring, wherein the heteroaryl ring or heterocycloalkyl ring contains 1 or 2 oxygen ring members, wherein said 5-membered heteroaryl ring or a 6-membered heterocycloalkyl ring are each optionally substituted with 1 or 2 independently selected $R^C$ substituents;

each $R^C$ is independently selected from H, D, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^5$, $R^6$, $R^7$, and $R^8$ are each independently selected H, halo, CN, OH, $NO_2$, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkoxycarbonylamino, $C_{1-6}$ alkylaminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

Ring moiety A is a pyrazole ring, which is optionally substituted with 1, 2, or 3 independently selected $R^A$ substituents;

Ring moiety B is a pyrazole ring, which is optionally substituted with 1, 2, or 3 independently selected $R^B$ substituents;

each $R^A$ is independently selected from H, $C_{1-6}$ alkyl, $C_{2-6}$ alkenyl, $C_{2-6}$ alkynyl, CN, and $C_{1-6}$ haloalkyl;

each $R^B$ is independently selected from H, $C_{1-6}$ alkyl, $C_{2-6}$ alkenyl, $C_{2-6}$ alkynyl, CN, and $C_{1-6}$ haloalkyl;

$L^1$ is selected from —R—R— and —R—R—R—; and each R is independently selected from $C_{1-6}$ alkylene, $C_{2-6}$ alkenylene, and $C_{2-6}$ alkynylene.

17. The method of claim 1, wherein:

$R^1$ and R'' are each a bond;

$R^2$ is H;

$R^{2''}$ is H;

$R^3$ and $R^4$ are each independently selected from H, halo, CN, OH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;

Ring C is a moiety selected from:

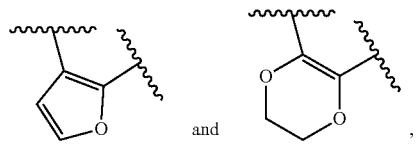 [SMILES: *c1ccoc1* ; *C1=C(*)OCCO1]

and each of which are optionally substituted with 1 or 2 independently selected $R^C$ substituents;

each $R^C$ is independently selected from H and $C_{1-6}$ alkyl;

$R^5$, $R^6$, $R^7$, and $R^8$ are each independently selected H, halo, CN, OH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, carbamyl, $C_{1-6}$ alkylcarbamyl, and di($C_{1-6}$ alkyl)carbamyl;

Ring moiety A is a pyrazole ring, which is optionally substituted with 1, 2, or 3 independently selected $R^A$ substituents;

Ring moiety B is a pyrazole ring, which is optionally substituted with 1, 2, or 3 independently selected $R^B$ substituents;

each $R^A$ is independently selected from H and $C_{1-6}$ alkyl;

each $R^B$ is independently selected from H and $C_{1-6}$ alkyl;

$L^1$ is selected from —R—R— and —R—R—R—; and each R is independently selected from $C_{1-3}$ alkylene, $C_{2-3}$ alkenylene, and $C_{2-3}$ alkynylene.

18. The method of claim 1, wherein the compound of Formula (III) is a compound having Formula (V) or (VI):

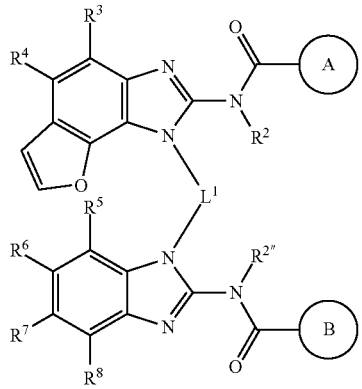
(V)

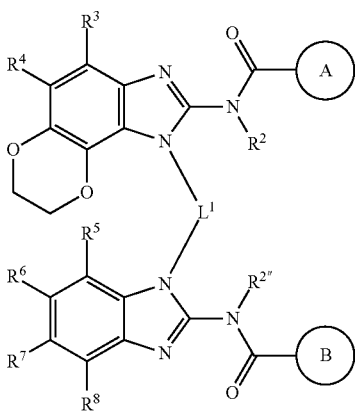
(VI)

or a pharmaceutically acceptable salt thereof.

19. The method of claim 1, wherein the compound of Formula (III) is a compound having Formula (IX) or (X):

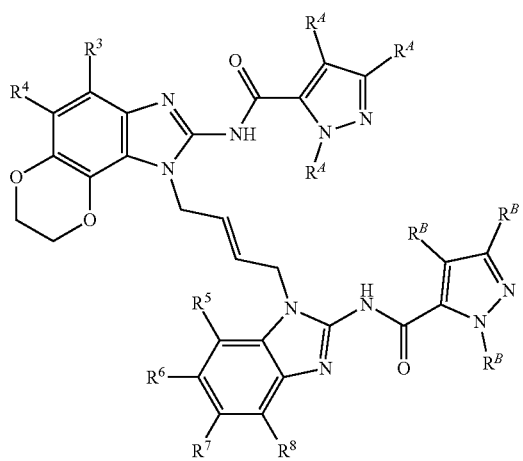
(IX)

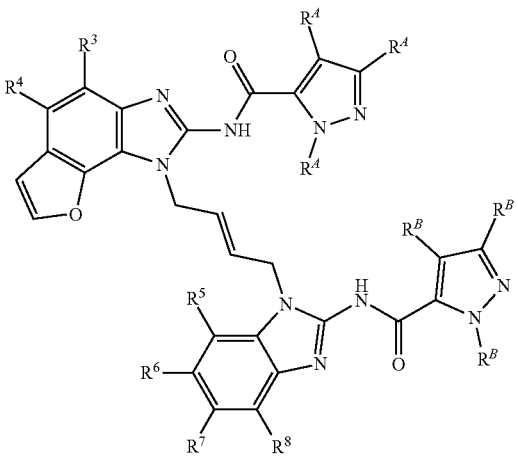
(X)

or a pharmaceutically acceptable salt thereof.

20. The method of claim 1, wherein the compound of Formula (III) is selected from:

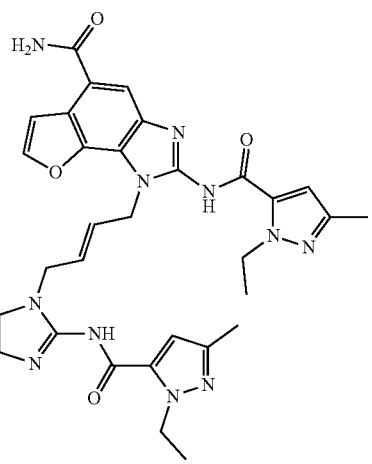
and

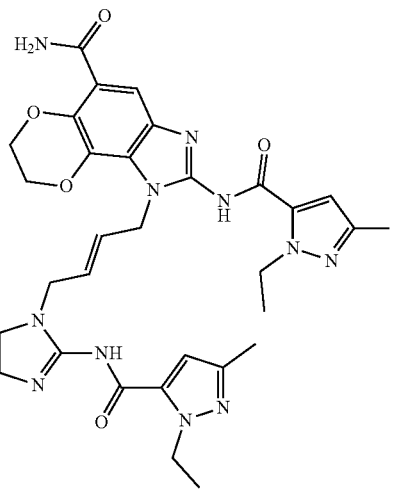
;

or a pharmaceutically acceptable salt thereof.

21. The method of claim 1, wherein the compound of Formula (III) is:

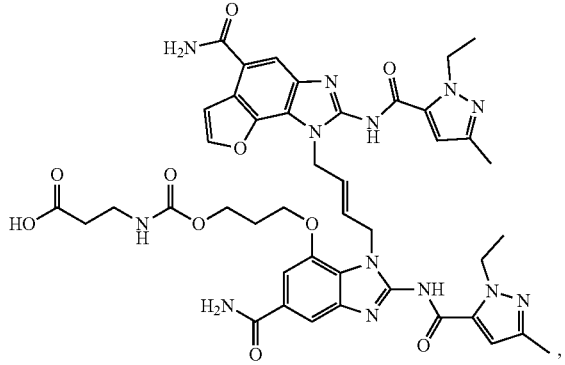 [SMILES: CCn1nc(C)cc1C(=O)Nc1nc2cc(C(N)=O)cc(OCCCOC(=O)NCCC(=O)O)c2n1C/C=C/Cn1c(NC(=O)c2cc(C)nn2CC)nc2cc(C(N)=O)c3ccoc3c21]

or a pharmaceutically acceptable salt thereof.

22. The method of claim 1, wherein the compound of Formula (III) is:

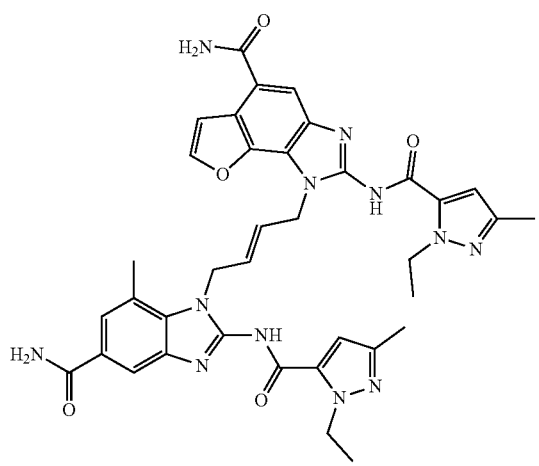

or a pharmaceutically acceptable salt thereof.

23. The method of claim 1, wherein the compound of Formula (III) is:

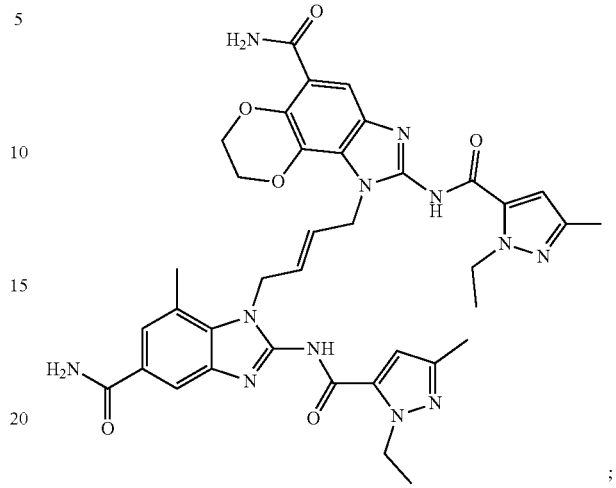

or a pharmaceutically acceptable salt thereof.

24. The method of claim 1, wherein the STING-mediated disease or disorder is bladder cancer.

25. The method of claim 1, wherein the STING-mediated disease or disorder is head and neck cancer.

26. The method of claim 25, wherein the head and neck cancer is head and neck squamous cell carcinoma (HNSCC).

27. The method of claim 1, wherein the STING-mediated disease or disorder is uterine cancer (UC).

28. The method of claim 1, wherein the STING-mediated disease or disorder is prostate cancer.

29. The method of claim 1, wherein the STING-mediated disease or disorder is lung cancer.

30. The method of claim 29, wherein the lung cancer is small cell lung carcinoma (SCLC).

31. The method of claim 1, wherein the STING-mediated disease or disorder is melanoma.

32. The method of claim 1, wherein the STING-mediated disease or disorder is colorectal cancer.

33. The method of claim 1, wherein the STING-mediated disease or disorder is salivary gland cancer.

34. The method of claim 1, wherein the STING-mediated disease or disorder is skin cancer.

35. The method of claim 1, wherein the STING-mediated disease or disorder is breast cancer.

36. The method of claim 35, wherein the breast cancer is triple-negative breast cancer.

37. The method of claim 1, wherein the STING-mediated disease or disorder is ovarian cancer.

38. The method of claim 1, wherein the STING-mediated disease or disorder is lymphoma.

39. The method of claim 38, wherein the lymphoma is T-cell lymphoma.

40. The method of claim 1, wherein the STING-mediated disease or disorder is pancreatic cancer.

41. The method of claim 1, wherein the STING-mediated disease or disorder is oral cancer.

* * * * *

UNITED STATES PATENT AND TRADEMARK OFFICE
CERTIFICATE OF CORRECTION

PATENT NO. : 11,427,597 B2
APPLICATION NO. : 17/079094
DATED : August 30, 2022
INVENTOR(S) : Liangxing Wu, Neil Lajkiewicz and Wenqing Yao Page 1 of 1

It is certified that error appears in the above-identified patent and that said Letters Patent is hereby corrected as shown below:

In the Claims

Column 119, Line 64, Claim 1, after "$C_{2-6}$ alkenyl," insert -- $C_{2-6}$ alkynyl, --;

Column 120, Line 45, Claim 1, delete "haloalkyl" and insert -- haloalkyl, --;

Column 122, Line 16, Claim 1, delete "$R^{c51}$" and insert -- $R^{c51}$, --;

Column 126, Line 12, Claim 1, delete "alkyl)" and insert -- di($C_{1-3}$ alkyl) --;

Column 126, Line 14, Claim 1, delete "alkyl)" and insert -- di($C_{1-3}$ alkyl) --;

Column 126, Line 25, Claim 4, delete "$NR^{c3}C(=O)OR^{b3}$," and insert -- $NR^{c3}S(=O)_2R^{b3}$, --;

Column 129, Line 21, Claim 14, delete "$OR^{aA}C(=O)R^{bA}$," and insert -- $OR^{aA}$, $C(=O)R^{bA}$, --;

Column 129, Lines 25-26, Claim 14, delete "alkyl, alkyl," and insert -- alkyl, --;

Column 129, Line 38, Claim 14, before "$R^{aA}$," insert -- each --; and

Column 132, Line 29, Claim 17, delete "R"" and insert -- $R^{1}$ --.

Signed and Sealed this
Eighteenth Day of October, 2022

*Katherine Kelly Vidal*

Katherine Kelly Vidal
*Director of the United States Patent and Trademark Office*